(12) United States Patent
Kim et al.

(10) Patent No.: US 7,572,921 B2
(45) Date of Patent: Aug. 11, 2009

(54) SUBSTITUTED BENZYLIMIDAZOLES USEFUL FOR THE TREATMENT OF INFLAMMATORY DISEASES

(75) Inventors: Jin Mi Kim, Sandy Hook, CT (US); Rene' Marc Lemieux, Plantsville, CT (US); Bryan McKibben, New Milford, CT (US); Matt Aaron Tschantz, Newtown, CT (US); Hui Yu, New Milford, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/278,558

(22) Filed: Apr. 4, 2006

(65) Prior Publication Data

US 2006/0252811 A1    Nov. 9, 2006

Related U.S. Application Data

(60) Provisional application No. 60/668,368, filed on Apr. 5, 2005.

(51) Int. Cl.
| | |
|---|---|
| *A61K 31/4178* | (2006.01) |
| *A61K 31/4164* | (2006.01) |
| *C07D 233/64* | (2006.01) |
| *C07D 401/12* | (2006.01) |
| *C07D 401/14* | (2006.01) |
| *C07D 403/12* | (2006.01) |
| *C07D 413/12* | (2006.01) |

(52) U.S. Cl. .................... 548/335.5; 544/139; 544/370; 546/210; 546/272.7; 546/275.1; 514/235.8; 514/254.05; 514/326; 514/341; 514/399

(58) Field of Classification Search ............... 548/335.5
See application file for complete search history.

(56) References Cited

U.S. PATENT DOCUMENTS

| | | | |
|---|---|---|---|
| 4,532,331 A * | 7/1985 | Frazee et al. | 548/335.5 |
| 6,063,628 A | 5/2000 | Loeb et al. | |
| 6,355,664 B1 | 3/2002 | Kelly et al. | |
| 6,492,408 B1 | 12/2002 | Wu et al. | |
| 2004/0006011 A1 | 1/2004 | Gour et al. | |

FOREIGN PATENT DOCUMENTS

JP          63270665       11/1988

OTHER PUBLICATIONS

Toyofuku et al., CA 111:7403 (1989).*
An English translation of JP 63-270667, 1988.*
Patent Abstract of Japan; Publication No. 63270665; Publication Date: Aug. 11, 1998; Applicant: Wakamoto Pharmacuet Co. Ltd.
International Search Report for PCT/US2006/012431, Jul. 26, 2006.

* cited by examiner

*Primary Examiner*—Laura L. Stockton
(74) *Attorney, Agent, or Firm*—Michael P. Morris; Mary-Ellen M. Devlin; Philip I. Datlow

(57) ABSTRACT

The invention comprises a class of derivatives of substituted benzylimidazoles of the formula (I) and methods for making the same. These compounds are useful for the treatment of inflammatory conditions.

(I)

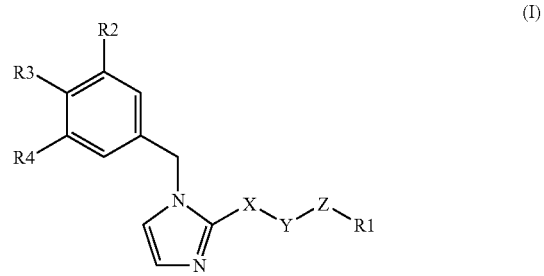

6 Claims, No Drawings

SUBSTITUTED BENZYLIMIDAZOLES USEFUL FOR THE TREATMENT OF INFLAMMATORY DISEASES

CROSS-REFERENCE TO RELATED APPLICATIONS

This application claims benefit to U.S. Provisional Application No. 60/668,368, filed Apr. 5, 2005.

BACKGROUND OF THE INVENTION

1. Technical Field

The present invention relates generally to a series of novel benzylimidazole derivatives, the synthesis of these compounds and their use in the treatment of inflammatory disease.

2. Background Information

Research spanning the last decade has helped to elucidate the molecular events attending cell-cell interactions in the body, especially those events involved in the movement and activation of cells in the immune system. See generally, Springer, T. *Nature,* 1990, 346, 425-434. Cell surface proteins, and especially the Cellular Adhesion Molecules ("CAMs") and "Leukointegrins", including LFA-1, MAC-1 and gp150.95 (referred to in WHO nomenclature as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently believed that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2, ICAM-3 or ICAM-4 which are expressed on blood vessel endothelial cell surfaces and on other leukocytes. The interaction of the CAMs with the Leukointegrins is a vital step in the normal functioning of the immune system. Immune processes such as antigen presentation, T-cell mediated cytotoxicity and leukocyte extravasation all require cellular adhesion mediated by ICAMs interacting with the Leukointegrins. See generally Kishimoto, T. K.; Rothlein; R. R. *Adv. Pharmacol.* 1994, 25, 117-138 and Diamond, M.; Springer, T. *Current Biology,* 1994, 4, 506-532.

A group of individuals has been identified which lack the appropriate expression of Leukointegrins, a condition termed "Leukocyte Adhesion Deficiency" (Anderson, D. C.; et al., *Fed. Proc.* 1985, 44, 2671-2677 and Anderson, D. C.; et al., *J. Infect. Dis.* 1985, 152, 668-689). These individuals are unable to mount a normal inflammatory and/or immune response(s) due to an inability of their cells to adhere to cellular substrates. These data show that immune reactions are mitigated when lymphocytes are unable to adhere in a normal fashion due to the lack of functional adhesion molecules of the CD18 family. By virtue of the fact that LAD patients who lack CD18 cannot mount an inflammatory response, it is believed that antagonism of CD18, CD11/ICAM interactions will also inhibit an inflammatory response.

It has been demonstrated that the antagonism of the interaction between the CAMs and the Leukointegrins can be realized by agents directed against either component. Specifically, blocking of the CAMs, such as for example ICAM-1, or the Leukointegrins, such as for example LFA-1, by antibodies directed against either or both of these molecules effectively inhibits inflammatory responses. In vitro models of inflammation and immune response inhibited by antibodies to CAMs or Leukointegrins include antigen or mitogen-induced lymphocyte proliferation, homotypic aggregation of lymphocytes, T-cell mediated cytolysis and antigen-specific induced tolerance. The relevance of the in vitro studies are supported by in vivo studies with antibodies directed against ICAM-1 or LFA-1. For example, antibodies directed against LFA-1 can prevent thyroid graft rejection and prolong heart allograft survival in mice (Gorski, A.; *Immunology Today,* 1994, 15, 251-255). Of greater significance, antibodies directed against ICAM-1 have shown efficacy in vivo as anti-inflammatory agents in human diseases such as renal allograft rejection and rheumatoid arthritis (Rothlein, R. R.; Scharschmidt, L., in: *Adhesion Molecules*; Wegner, C. D., Ed.; 1994, 1-38, Cosimi, C. B.; et al., *J. Immunol.* 1990, 144, 4604-4612 and Kavanaugh, A.; et al., *Arthritis Rheum.* 1994, 37, 992-1004) and antibodies directed against LFA-1 have demonstrated immunosuppressive effects in bone marrow transplantation and in the prevention of early rejection of renal allografts (Fischer, A.; et al., *Lancet,* 1989, 2, 1058-1060 and Le Mauff, B.; et al., *Transplantation,* 1991, 52, 291-295).

It has also been demonstrated that a recombinant soluble form of ICAM-1 can act as an inhibitor of the ICAM-1 interaction with LFA-1. Soluble ICAM-1 acts as a direct antagonist of CD18, CD11/ICAM-1 interactions on cells and shows inhibitory activity in in vitro models of immune response such as the human mixed lymphocyte response, cytotoxic T cell responses and T cell proliferation from diabetic patients in response to islet cells (Becker, J. C.; et al., *J. Immunol.* 1993, 151, 7224 and Roep, B. O.; et al., *Lancet,* 1994, 343, 1590).

Thus, the prior art has demonstrated that large protein molecules which antagonize the binding of the CAMs to the Leukointegrins have therapeutic potential in mitigating inflammatory and immunological responses often associated with the pathogenesis of many autoimmune or inflammatory diseases. However proteins have significant deficiencies as therapeutic agents, including the inability to be delivered orally and potential immunoreactivity which limits the utility of theses molecules for chronic administration. Furthermore, protein-based therapeutics are generally expensive to produce.

It follows that small molecules, having the similar ability as large protein molecules to directly and selectively antagonize the binding of the CAMs to the Leukointegrins would make preferable therapeutic agents.

Several small molecules have been described in the literature that affect the interaction of CAMs and Leukointegrins. For example, U.S. Pat. No. 6,355,664 and the corresponding WO 98/39303 disclose a class of small molecules having a hydantoin core, that are inhibitors of the interaction of LFA-1 and ICAM-1. U.S. Pat. No. 6,492,408 and the corresponding WO 01/07440 A1 discloses compounds having this same activity that instead have a 6,7-dihydro-5H-imidazo[1,2-α]

imidazole-3-sulfonyl core. While the compounds that are described by U.S. Pat. No. 6,492,408 and the corresponding WO 01/07440 A1 have a more potent inhibitory affect upon the interaction of CAMs and Leukointegrins than do the hydantoins of U.S. Pat. No. 6,355,664 and the corresponding WO9839303, they nevertheless are not ideal therapeutic agents because the rate at which they are metabolized is undesirably high.

Thus, the problem to be solved by the present invention is to find small molecules that have not only good inhibitory effect upon the interaction of CAMs and Leukointegrins but that also are metabolized at a rate that is not overly rapid.

BRIEF SUMMARY OF THE INVENTION

The invention comprises a class of derivatives of substituted benzylimidazoles and methods for making the same. These compounds are useful for the treatment of inflammatory conditions in that they exhibit good inhibitory effect upon the interaction of CAMs and Leukointegrins and are metabolized fairly slowly. Thus, the invention further comprises the use of these compounds for the treatment or prophylaxis of inflammatory conditions and pharmaceutical compositions comprising the same as active ingredients. Thus, particular embodiments of the invention include: the compounds of formula (I) and the pharmaceutically acceptable salts and esters thereof, pharmaceutical compositions comprising a compound of the formula (I), or a pharmaceutically acceptable salt or ester thereof, and one or more pharmaceutically acceptable carriers or adjuvants; and methods for the treatment or prophylaxis of an inflammatory condition as described herein comprising administering to a patient in need thereof a therapeutically or prophylactically effective amount of a compound of the formula (I), or a pharmaceutically acceptable salt or ester thereof.

DETAILED DESCRIPTION OF THE INVENTION

Definition of Terms and Conventions Used

Terms not specifically defined herein should be given the meanings that would be given to them by one of skill in the art in light of the disclosure and the context. As used in the present specification and claims, however, unless specified to the contrary, the following terms have the meaning indicated and the following conventions are adhered to.

In general, for groups comprising two or more subgroups, the last named group is the radical attachment point, for example, "alkylaryl" means a monovalent radical of the formula Alk-Ar—, while "arylalkyl" means a monovalent radical of the formula Ar-Alk-(where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

All alkyl groups shall be understood as being branched or unbranched unless otherwise specified. Other more specific definitions are as follows:

The term "carbocycle" refers to a 4-10 membered, monocyclic or bicyclic, saturated or partially or fully unsaturated (including aromatic), carbocyclic ring systems. Examples of "carbocyle" groups include cycloalkyl groups, such as cyclobutyl, cyclopentyl and cyclohexyl, aryl groups such as phenyl and naphthyl, and partially saturated carbocyclic ring groups such as indanyl and tetrahydronapththyl.

The term "aryl" refers to a 6-10 membered monocyclic or bicyclic aromatic carbocycle, and includes, for example, phenyl and naphthyl; other terms comprising "aryl" will have the same definition for the aryl component, and examples of these moieties include: arylalkyl, aryloxy or arylthio.

The term "heteroaryl" refers to a 5 or 6 membered monocyclic, aromatic heterocyclic ring having ring system having ring carbon atoms and from 1 to 2 ring heteroatoms selected from nitrogen, oxygen and sulfur. Examples "heteroaryl" radicals include, pyridyl, pyrimidinyl, pyrazinyl, pyridazinyl, pyrrolyl, imidazolyl, pyrazolyl, thienyl, furyl, isoxazolyl, isothiazolyl, oxazolyl, thiazolyl, oxadiazolyl, and thiadiazolyl.

Specific compounds of the present invention may be identified in the present specification by chemical name and/or chemical structure. In the event of any conflict between the chemical name and chemical structure, the chemical structure will control.

EMBODIMENTS OF THE INVENTION

In a generic embodiment, there is provided compounds of the formula (I)

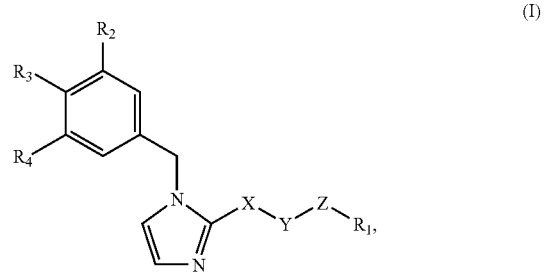

wherein:

X is:
- (A) a group of the formula —NR— wherein R is a hydrogen atom or a $C_{1-4}$alkyl group with the proviso that Y is a methylene or
- (B) a methylene group optionally substituted with:
  - (i) oxo with the proviso that Y is a methylene group and Z is a bond, or
  - (ii) a $C_{1-3}$alkyl group, y is:
- (A) a methylene group optionally substituted with a group of the formula —$COR_5$, wherein $R_5$ is selected from:
  - (i) a phenyl or a phenyl$C_{1-3}$alkyl group, and each is optionally substituted with one to three groups independently selected from:
    - (A) halogen,
    - (B) a group of the formula —$OR_{11}$, wherein $R_{11}$ is a hydrogen atom or a $C_{1-3}$alkyl group,
  - (ii) a group of the formula —$NR_{6a}R_{6b}$, wherein $R_{6a}$ and $R_{6b}$ are each independently:
    - (a) a hydrogen atom,
    - (b) a $C_{1-3}$alkyl group, (iii) a group of the formula —$OR_6$, wherein $R_6$ is a hydrogen atom or a $C_{1-3}$alkyl group,
(B) an oxygen atom,
(C) a sulfur atom, or
(D) a group of the formula —$NR_7$— wherein $R_7$ is a hydrogen atom or a $C_{1-5}$alkyl group optionally substituted with one to three groups independently selected from:
  (i) oxo,
  (ii) a group of the formula —$OR_8$, wherein $R_8$ is a hydrogen atom or a $C_{1-5}$alkyl group,
  (iii) a group of the formula —$NR_9R_{10}$, wherein $R_9$ and $R_{10}$ are each independently:
    (a) a hydrogen atom,
    (b) a $C_{1-5}$alkyl group,
    (c) a $C_{1-5}$alkylcarbonyl group,
    (d) an arylcarbonyl group,
    (e) a $C_{1-5}$alkylaminocarbonyl group, or
    (f) a $C_{1-5}$alkyloxycarbonyl group,
    or wherein $R_9$ and $R_{10}$ together constitute a saturated bridge of 4 to 6 methylene groups which together with the nitrogen atom between them form a heterocyclic ring, wherein one methylene group is optionally replaced with O or N(R), wherein R is a hydrogen atom or a $C_{1-5}$alkyl group, and wherein said heterocyclic ring is optionally substituted with a $C_{1-5}$alkyl group optionally substituted with one to two groups independently selected from oxo or $NH_2$, and
  (iv) a $C_{4-7}$cycloalkyl group,
Z is:
  (A) a methylene group or,
  (B) a bond
$R_1$ is a $C_{4-10}$carbocycle or a 5 to 6 membered heteroaryl, and each is optionally substituted with one to three groups independently selected from:
  (A) halogen,
  (B) a group of the formula —$OR_{11}$, wherein $R_{11}$ is a hydrogen atom or a $C_{1-6}$alkyl group, and
  (C) a group of the formula —$NR_{12}R_{13}$, wherein $R_{12}$ and $R_{13}$ are each independently selected from:
    (i) a hydrogen atom,
    (ii) a $C_{1-6}$alkyl group, optionally substituted with one to three groups selected from:
      (a) oxo,
      (b) a group of the formula —$OR_{14}$, wherein $R_{14}$ is a hydrogen atom or a $C_{1-6}$alkyl group,
      (c) a group selected from phenyl, pyridyl and imidazolyl,
      (d) a group of the formula —$NR_{15}R_{16}$, wherein $R_{15}$ and $R_{16}$ are each independently:
        (i) a hydrogen atom,
        (ii) a $C_{1-6}$alkyl group, optionally substituted with oxo,
        or wherein $R_{15}$ and $R_{16}$ together constitute a saturated hydrocarbon bridge of 4 or 5 carbon atoms which together with the nitrogen atom between them form a heterocyclic ring, and wherein one atom in said hydrocarbon bridge is optionally replaced with O or $NR_{17}$, wherein $R_{17}$ is a hydrogen atom or a $C_{1-6}$alkyl group,
      (e) a pyrrolidine ring, wherein the nitrogen of said pyrrolidine ring is optionally substituted with a $C_{1-6}$alkyl group,
      (f) an imidazole ring optionally substituted with $C_{1-6}$alkyl,
      (g) a morpholine ring,
      (h) heteroaryl optionally substituted with $C_{1-6}$alkyl, or
      (i) arylamino,
    (iii) a cyclohexyl group, optionally substituted with one to three groups independently selected from:
      (a) —$OR_{14}$, wherein $R_{14}$ is a hydrogen atom or a $C_{1-6}$alkyl group, and
      (b) —$NR_{15}R_{16}$, wherein $R_{15}$ and $R_{16}$ are each independently a hydrogen atom or a $C_{1-6}$alkyl group, and
    (iv) —$SO_2R_{17}$, where $R_{17}$ is $C_{1-6}$alkyl,
    or wherein $R_{12}$ and $R_{13}$ together constitute a saturated hydrocarbon bridge of 4 to 7 methylene groups which together with the nitrogen atom between them form a heterocyclic ring, wherein one methylene group is optionally replaced with O or N(R), wherein R is a hydrogen atom or a $C_{1-6}$alkyl group, and wherein said heterocyclic ring is optionally substituted with:
      (i) oxo
      (ii) a group of the formula —$OR_{18}$, wherein $R_{18}$ is a hydrogen atom or a $C_{1-6}$alkyl group,
      (iii) a group of the formula —$NR_{19}R_{20}$, wherein $R_{19}$ and $R_{20}$ are each independently a hydrogen atom or a $C_{1-6}$alkyl group optionally substituted with oxo,
      (iv) a piperidine ring, wherein the nitrogen of said piperidine ring is optionally substituted with a $C_{1-6}$alkyl group, or
      (v) a $C_{1-6}$alkyl group, optionally substituted with 1 to 3 groups independently selected from:
        (a) oxo,
        (b) —$NR_{21}R_{22}$, where $R_{21}$ and $R_{22}$ are are each independently a hydrogen atom or $C_{1-6}$alkyl optionally substituted with oxo, or
        (c) a group of the formula —$OR_{18}$, wherein $R_{18}$ is a hydrogen atom or a $C_{1-6}$alkyl group,
  (D) a $C_{1-6}$alkyl group, optionally substituted with 1 to 3 groups independently selected from:
    (i) oxo,
    (ii) halogen, or
    (iii) a group of the formula —$NR_{23}R_{24}$, wherein $R_{23}$ and $R_{24}$ are each independently a hydrogen atom or an alkyl of 1 to 3 carbon atoms,
  (E) a nitro group, or
  (F) —$SO_2R_{25}$, where $R_{25}$ is a hydrogen atom or $C_{1-6}$alkyl,
$R_2$ is:
  (A) a halogen, or
  (B) a $CF_3$ group;
$R_3$ is a hydrogen atom;
$R_4$ is:
  (A) a halogen, or
  (B) a $CF_3$ group,
or $R_2$ is a hydrogen atom, $R_3$ is a halogen, and $R_4$ is a hydrogen atom;
or a pharmaceutically acceptable salt or ester thereof.

In another embodiment there are provided compounds of formula I as described above and wherein:

X is a methylene group which is optionally substituted with $C_{1-2}$alkyl,

Y is:
(A) an oxygen atom, or
(B) a group of the formula —$NR_7$— wherein $R_7$ is a hydrogen atom or a $C_{1-4}$alkyl group optionally substituted with one to two groups independently selected from:
  (i) oxo,
  (ii) a group of the formula —$NR_9R_{10}$, wherein $R_9$ and $R_{10}$ are each independently:
    (a) a hydrogen atom, or
    (b) a $C_{1-5}$alkylcarbonyl group,
    (c) an arylcarbonyl group,
    (d) $C_{1-5}$alkylaminocarbonyl, or
    (e) $C_{1-5}$alkyloxycarbonyl,
  (iii) a group of the formula —$OR_8$ where —$OR_8$ is selected from a hydrogen atom or a $C_{1-5}$alkyl, Z is a methylene group or a bond, $R_1$ is selected from phenyl, pyridyl, indanyl, naphthyl, tetrahydronaphthyl, or cyclohexyl, each optionally substituted with one to three groups independently selected from:
(A) halogen,
(B) a group of the formula —$OR_{11}$, wherein $R_{11}$ is a hydrogen atom or an alkyl of 1 to 3 carbon atoms,
(C) a group of the formula —$NR_{12}R_{13}$, wherein $R_{12}$ and $R_{13}$ are selected from:
  (i) a hydrogen atom
  (ii) $C_{1-5}$alkyl which is optionally substituted with:
    (a) oxo,
    (b) a group of the formula —$OR_{14}$, wherein —$OR_{14}$ is selected from a hydrogen atom or $C_{1-5}$alkyl,
    (c) —$NR_{15}R_{16}$, wherein $R_{15}$ and $R_{16}$ are selected from hydrogen or $C_{1-5}$alkyl which is optionally substituted with oxo,
    (d) morpholine, or
    (e) a heterocyclic ring selected from pyrrolidine, imidazole and pyridyl, each optionally substituted with $C_{1-5}$alkyl, or
  (iii) cyclohexyl optionally substituted with —$NH_2$;
  or wherein $R_{12}$ and $R_{13}$ together constitute a saturated hydrocarbon bridge of 4 to 7 methylene groups which together with the nitrogen atom between them form a heterocyclic ring, wherein said heterocyclic ring is optionally substituted with:
    (i) $C_{1-5}$alkyl optionally substituted with —OH,
    (ii) a group of the formula —$NR_{19}R_{20}$ where $R_{19}$ and $R_{20}$ are each selected from hydrogen, $C_{1-5}$alkyl or $C_{1-5}$alkylcarbonyl, or
    (iii) —$CONH_2$,
(D) a nitro group,
(E) $C_{1-2}$alkyl optionally substituted with one to three fluorine atoms, $R_2$ is:
(A) a chorine atom, or
(B) a $CF_3$ group, $R_3$ is a hydrogen atom, and $R_4$ is a chlorine atom or a $CF_3$ group, or a pharmaceutically acceptable salt or ester thereof.

In a further embodiment there are provided compounds of the formula I as described above and wherein:

X is —$CH_2$—,

Y is a group of the formula —$NR_7$—, wherein $R_7$ is selected from
(A) hydrogen atom
(B) $C_{1-3}$alkyl group optionally substituted with:
  (i) oxo,
  (ii) a group of the formula —$NR_9R_{10}$, wherein $R_9$ and $R_{10}$ are each independently:
    (a) a hydrogen atom,
    (b) a $C_{1-2}$alkylcarbonyl group,
    (c) a $C_{1-4}$alkyloxycarbonyl, Z is —$CH_2$—, $R_1$ is phenyl optionally substituted with one to two fluorine atoms, $R_2$ is a chlorine atom, $R_3$ is a hydrogen atom, and $R_4$ is a chlorine atom;

or a pharmaceutically acceptable salt or ester thereof.

In yet a further embodiment there are provided compounds of the formula I as described above and wherein:

X is —$CH_2$—,

Y is an oxygen atom,

Z is a bond, $R_1$ is phenyl or pyridyl, optionally substituted with one to two groups independently selected from:
(A) a fluorine or chlorine atom,
(B) —$OCH_3$,
(C) a group of the formula —$NR_{12}R_{13}$, wherein $R_{12}$ and $R_{13}$ are each independently selected from
  (i) hydrogen
  (ii) $C_{1-3}$alkyl optionally and independently substituted with
    (a) —$N(CH_3)_2$
    (b) —$NHCOCH_3$,
    (c) pyrrolidine, which is optionally substituted with $C_{1-2}$alkyl,
    (d) imidazole,
    (e) pyridine, and
  (iii) cyclohexyl optionally substituted with —$NH_2$
  or wherein $R_{12}$ and $R_{13}$ together constitute a saturated hydrocarbon bridge of 4 methylene groups which together with the nitrogen atom between them form a heterocyclic ring, wherein said heterocyclic ring is optionally substituted with —$CONH_2$ or —$N(CH_3)COCH_3$;

$R_2$ is a chlorine atom, $R_3$ is a hydrogen atom, and $R_4$ is a chlorine atom;

or a pharmaceutically acceptable salt or ester thereof.

In still another embodiment there are provided the following compounds:

| Structure | Name |
|---|---|
| 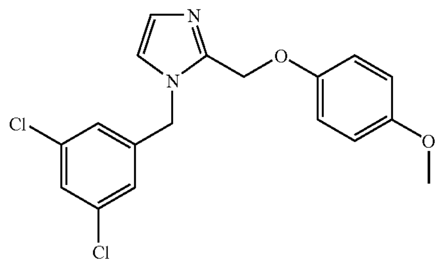 | 1-(3,5-Dichloro-benzyl)-2-(4-methoxy-phenoxymethyl)-1H-imidazole |
| 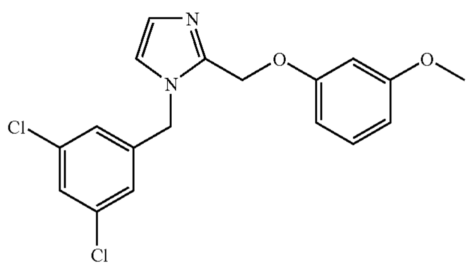 | 1-(3,5-Dichloro-benzyl)-2-(3-methoxy-phenoxymethyl)-1H-imidazole |
| 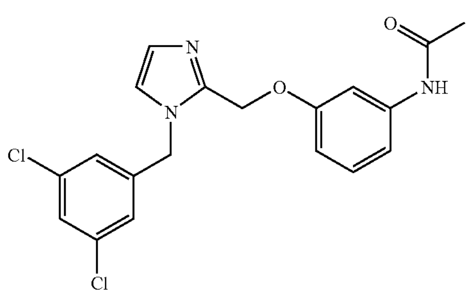 | N-{3-[1-(3,5-Dichloro-benzyl)-1H-imidazol-2-ylmethoxy]-phenyl}-acetamide |
| 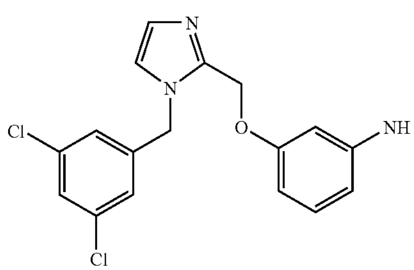 | 3-[1-(3,5-Dichloro-benzyl)-1H-imidazol-2-ylmethoxy]-phenylamine |
| 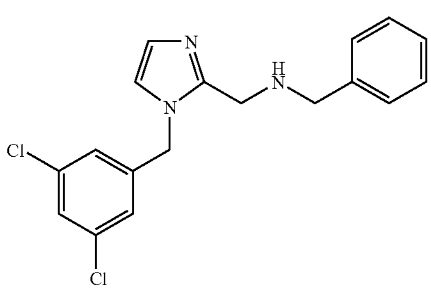 | Benzyl-[1-(3,5-dichloro-benzyl)-1H-imidazol-2-ylmethyl]-amine |

-continued

| Structure | Name |
|---|---|
| 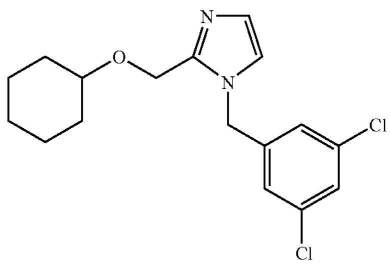 | 2-Cyclohexyloxymethyl-1-(3,5-dichloro-benzyl)-1H-imidazole |
| 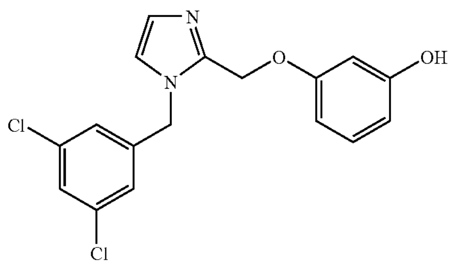 | 3-[1-(3,5-Dichloro-benzyl)-1H-imidazol-2-ylmethoxy]-phenol |
| 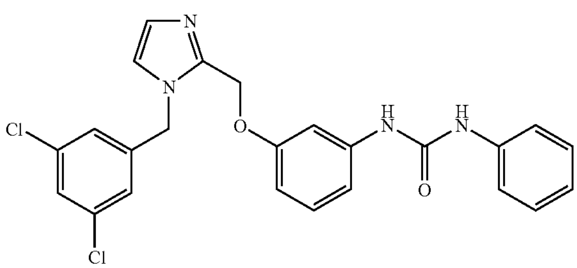 | 1-{3-[1-(3,5-Dichloro-benzyl)-1H-imidazol-2-ylmethoxy]-phenyl}-3-phenyl-urea |
| 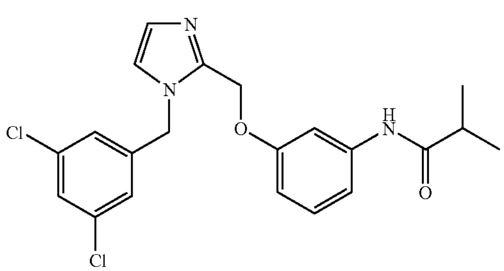 | N-{3-[1-(3,5-Dichloro-benzyl)-1H-imidazol-2-ylmethoxy]-phenyl}-isobutyramide |
| 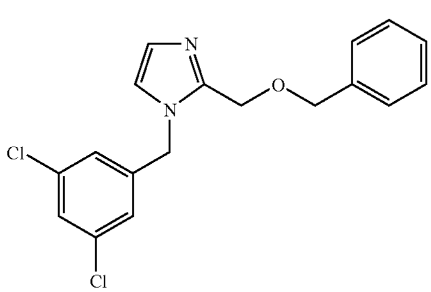 | 2-Benzyloxymethyl-1-(3,5-dichloro-benzyl)-1H-imidazole |

-continued

| Structure | Name |
|---|---|
| 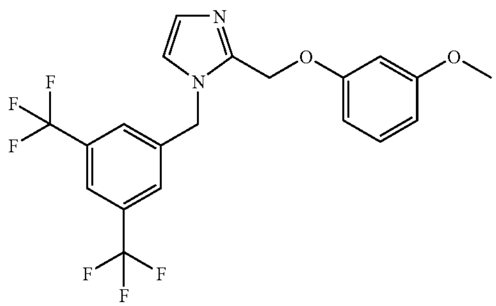 | 1-(3,5-Bis-trifluoromethyl-benzyl)-2-(3-methoxy-phenoxymethyl)-1H-imidazole |
| 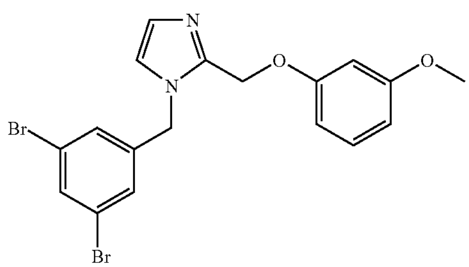 | 1-(3,5-Dibromo-benzyl)-2-(3-methoxy-phenoxymethyl)-1H-imidazole |
| 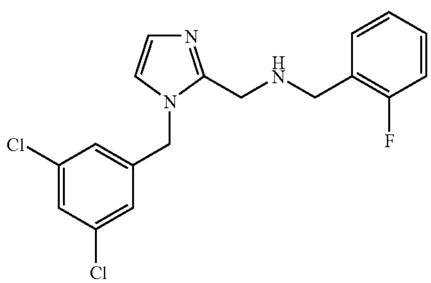 | [1-(3,5-Dichloro-benzyl)-1H-imidazol-2-ylmethyl]-(2-fluoro-benzyl)-amine |
| 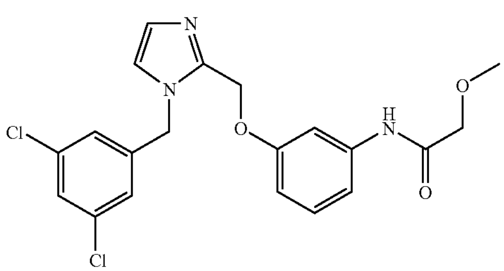 | N-{3-[1-(3,5-Dichloro-benzyl)-1H-imidazol-2-ylmethoxy]-phenyl}-2-methoxy-acetamide |
| 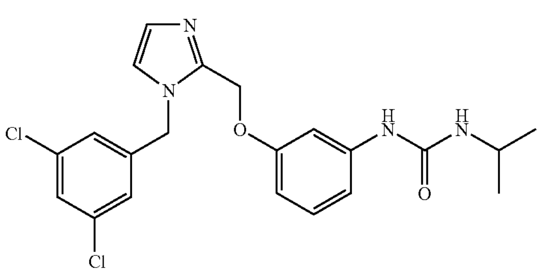 | 1-{3-[1-(3,5-Dichloro-benzyl)-1H-imidazol-2-ylmethoxy]-phenyl}-3-isopropyl-urea |

-continued

| Structure | Name |
|---|---|
| 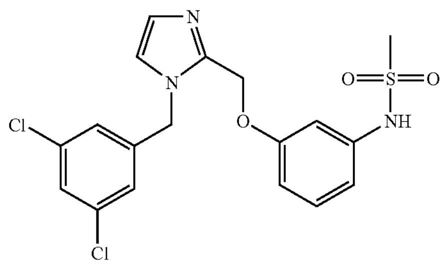 | N-{3-[1-(3,5-Dichloro-benzyl)-1H-imidazol-2-ylmethoxy]-phenyl}-methanesulfonamide |
| 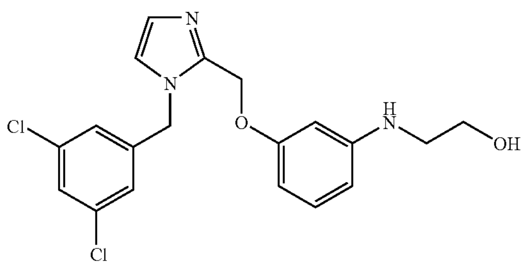 | 2-{6-[1-(3,5-Dichloro-benzyl)-1H-imidazol-2-ylmethoxy]-pyridin-2-ylamino}-ethanol |
| 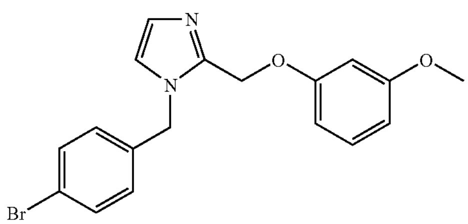 | 1-(4-Bromo-benzyl)-2-(3-methoxy-phenoxymethyl)-1H-imidazole |
| 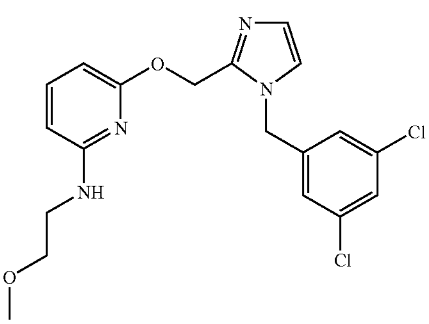 | {6-[1-(3,5-Dichloro-benzyl)-1H-imidazol-2-ylmethoxy]-pyridin-2-yl}-(2-methoxy-ethyl)-amine |
| 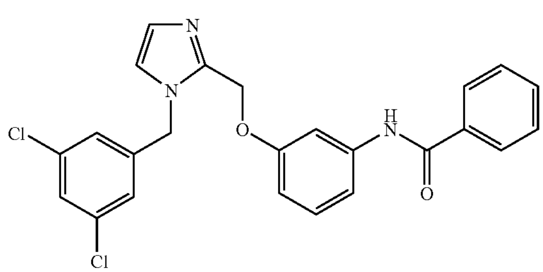 | N-{3-[1-(3,5-Dichloro-benzyl)-1H-imidazol-2-ylmethoxy]-phenyl}-benzamide |
| 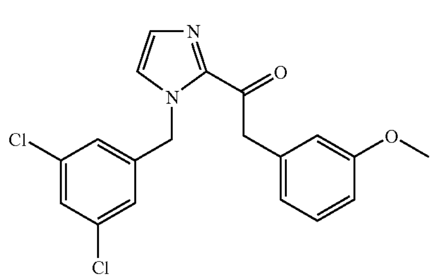 | 1-[1-(3,5-Dichloro-benzyl)-1H-imidazol-2-yl]-2-(3-methoxy-phenyl)-ethanone |

-continued

| Structure | Name |
|---|---|
| 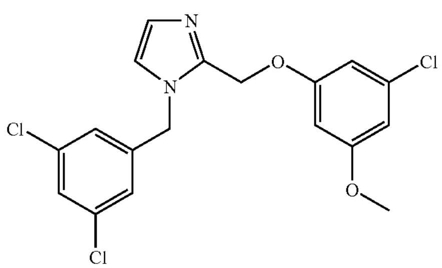 | 2-(3-Chloro-5-methoxy-phenoxymethyl)-1-(3,5-dichloro-benzyl)-1H-imidazole |
| 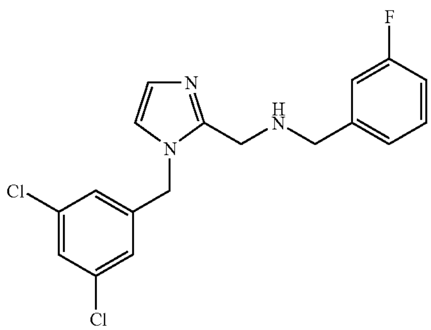 | [1-(3,5-Dichloro-benzyl)-1H-imidazol-2-ylmethyl]-(3-fluoro-benzyl)-amine |
| 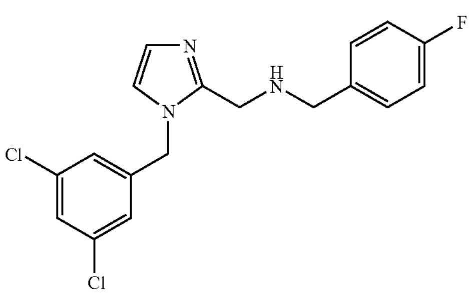 | [1-(3,5-Dichloro-benzyl)-1H-imidazol-2-ylmethyl]-(4-fluoro-benzyl)-amine |
| 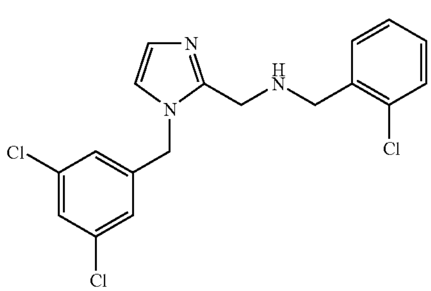 | (2-Chloro-benzyl)-[1-(3,5-dichloro-benzyl)-1H-imidazol-2-ylmethyl]-amine |
| 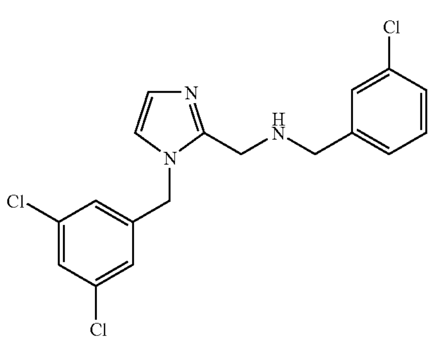 | (3-Chloro-benzyl)-[1-(3,5-dichloro-benzyl)-1H-imidazol-2-ylmethyl]-amine |

-continued

| Structure | Name |
|---|---|
| 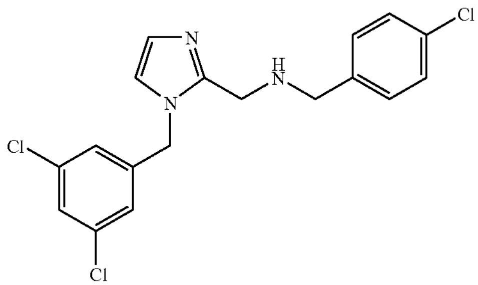 | (4-Chloro-benzyl)-[1-(3,5-dichloro-benzyl)-1H-imidazol-2-ylmethyl]-amine |
| 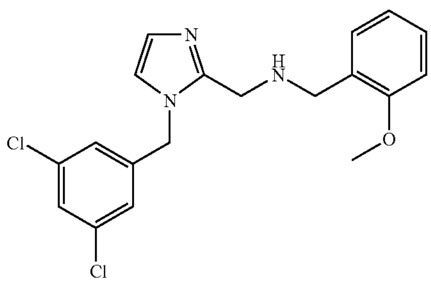 | [1-(3,5-Dichloro-benzyl)-1H-imidazol-2-ylmethyl]-(2-methoxy-benzyl)-amine |
| 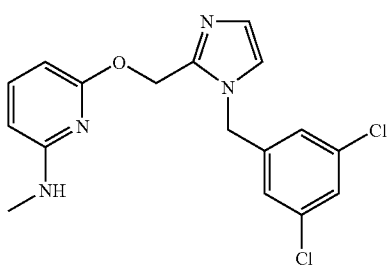 | {6-[1-(3,5-Dichloro-benzyl)-1H-imidazol-2-ylmethoxy]-pyridin-2-yl}-methyl-amine |
| 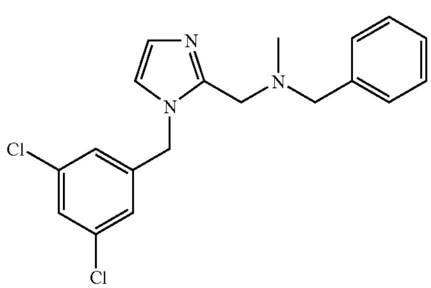 | Benzyl-[1-(3,5-dichloro-benzyl)-1H-imidazol-2-ylmethyl]-methyl-amine |
| 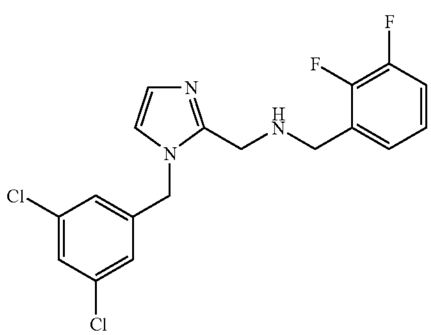 | [1-(3,5-Dichloro-benzyl)-1H-imidazol-2-ylmethyl]-(2,3-difluoro-benzyl)-amine |

| Structure | Name |
| --- | --- |
| 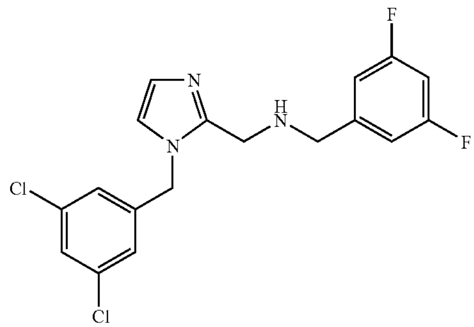 | [1-(3,5-Dichloro-benzyl)-1H-imidazol-2-ylmethyl]-(3,5-difluoro-benzyl)-amine |
| 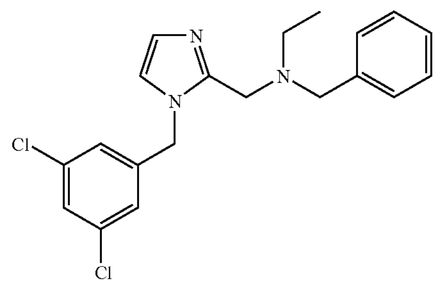 | Benzyl-[1-(3,5-dichloro-benzyl)-1H-imidazol-2-ylmethyl]-ethyl-amine |
| 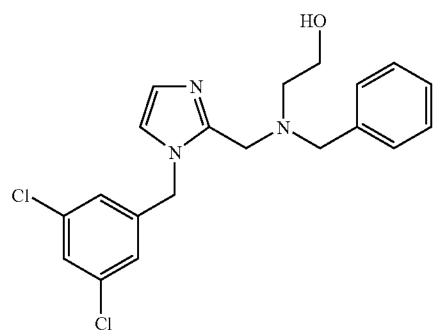 | 2-{Benzyl-[1-(3,5-dichloro-benzyl)-1H-imidazol-2-ylmethyl]-amino}-ethanol |
| 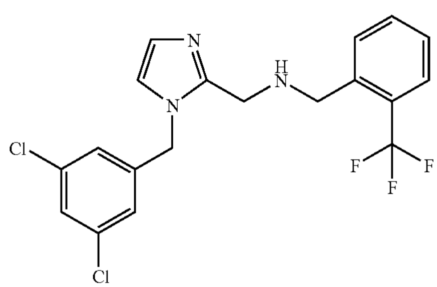 | [1-(3,5-Dichloro-benzyl)-1H-imidazol-2-ylmethyl]-(2-trifluoromethyl-benzyl)-amine |
| 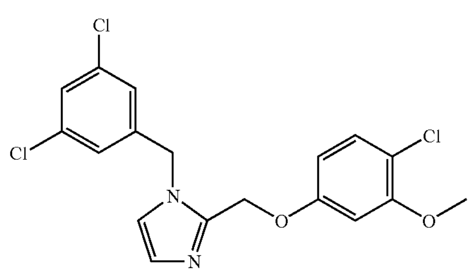 | 2-(4-Chloro-3-methoxy-phenoxymethyl)-1-(3,5-dichloro-benzyl)-1H-imidazole |

-continued

| Structure | Name |
|---|---|
| 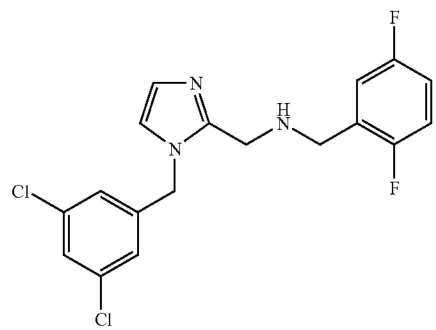 | [1-(3,5-Dichloro-benzyl)-1H-imidazol-2-ylmethyl]-(2,5-difluoro-benzyl)-amine |
| 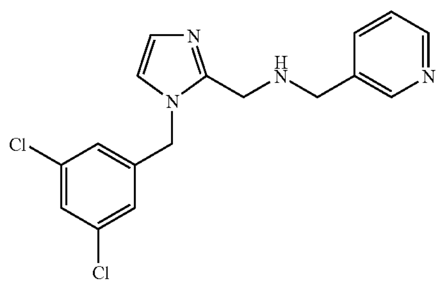 | [1-(3,5-Dichloro-benzyl)-1H-imidazol-2-ylmethyl]-pyridin-3-ylmethyl-amine |
| 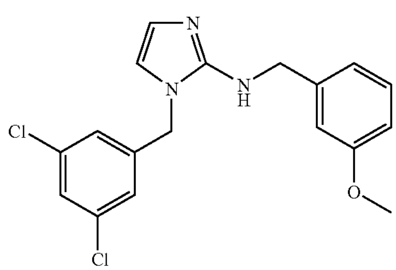 | [1-(3,5-Dichloro-benzyl)-1H-imidazol-2-yl]-(3-methoxy-benzyl)-amine |
| 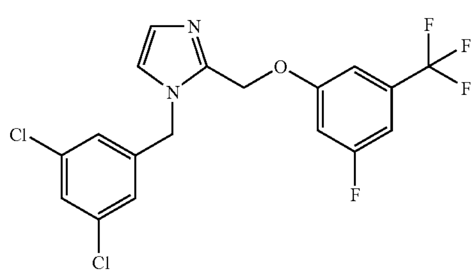 | 1-(3,5-Dichloro-benzyl)-2-(3-fluoro-5-trifluoromethyl-phenoxymethyl)-1H-imidazole |
| 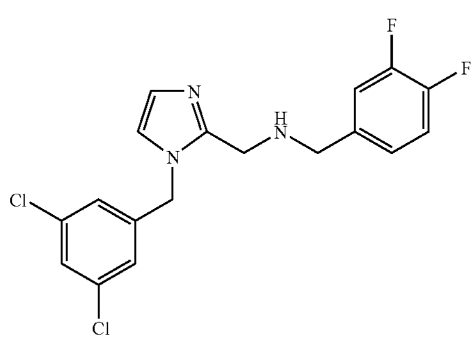 | [1-(3,5-Dichloro-benzyl)-1H-imidazol-2-ylmethyl]-(3,4-difluoro-benzyl)-amine |

| Structure | Name |
|---|---|
| 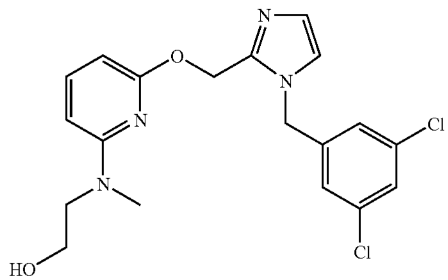 | 2-({6-[1-(3,5-Dichloro-benzyl)-1H-imidazol-2-ylmethoxy]-pyridin-2-yl}-methyl-amino)-ethanol |
| 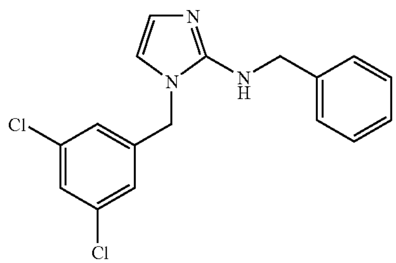 | Benzyl-[1-(3,5-dichloro-benzyl)-1H-imidazol-2-yl]-amine |
| 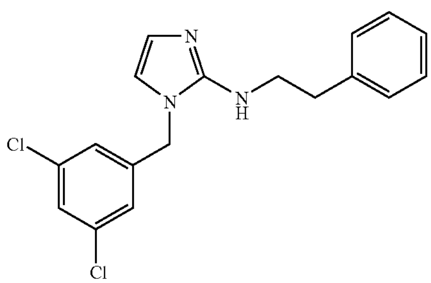 | [1-(3,5-Dichloro-benzyl)-1H-imidazol-2-yl]-phenethyl-amine |
| 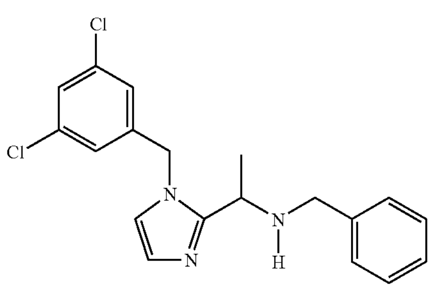 | Benzyl-{1-[1-(3,5-dichloro-benzyl)-1H-imidazol-2-yl]-ethyl}-amine |
| 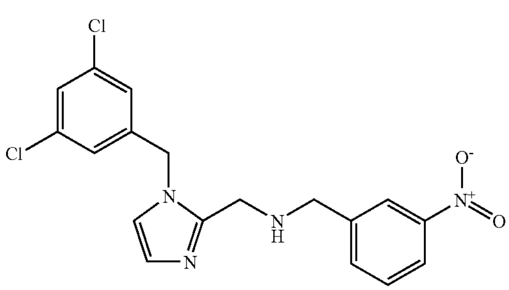 | [1-(3,5-Dichloro-benzyl)-1H-imidazol-2-ylmethyl]-(3-nitro-benzyl)-amine |

-continued

| Structure | Name |
|---|---|
| 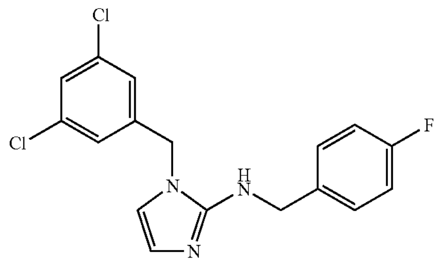 | [1-(3,5-Dichloro-benzyl)-1H-imidazol-2-yl]-(4-fluoro-benzyl)-amine |
| 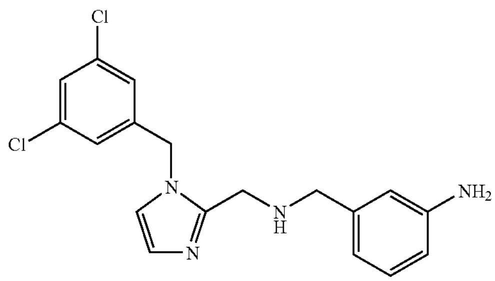 | 3-({[1-(3,5-Dichloro-benzyl)-1H-imidazol-2-ylmethyl]-amino}-methyl)-phenylamine |
| 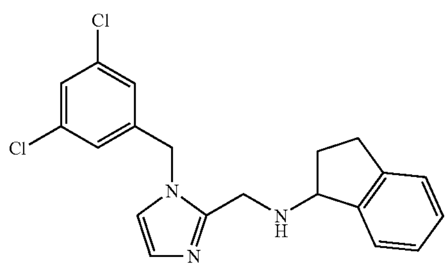 | [1-(3,5-Dichloro-benzyl)-1H-imidazol-2-ylmethyl]-indan-1-yl-amine |
| 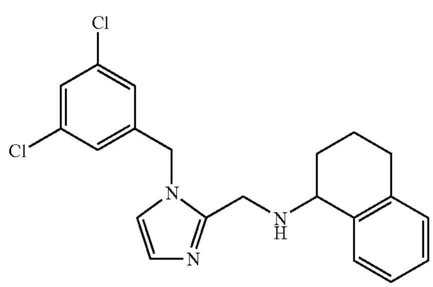 | [1-(3,5-Dichloro-benzyl)-1H-imidazol-2-ylmethyl]-(1,2,3,4-tetrahydro-naphthalen-1-yl)-amine |
| Chiral | (S)-1-{6-[1-(3,5-Dichloro-benzyl)-1H-imidazol-2-ylmethoxy]-pyridin-2-yl}-pyrrolidine-2-carboxylic acid amide |

-continued

| Structure | Name |
|---|---|
| 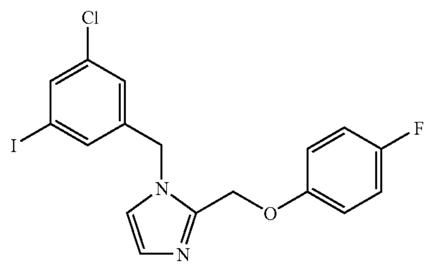 | 1-(3-Chloro-5-iodo-benzyl)-2-(4-fluoro-phenoxymethyl)-1H-imidazole |
| Chiral | ((S)-1-{6-[1-(3,5-Dichloro-benzyl)-1H-imidazol-2-ylmethoxy]-pyridin-2-yl}-pyrrolidin-2-yl)-methanol |
| Chiral | N-((R)-1-{6-[1-(3,5-Dichloro-benzyl)-1H-imidazol-2-ylmethoxy]-pyridin-2-yl}-pyrrolidin-3-yl)-acetamide |
| Chiral | N-((S)-1-{6-[1-(3,5-Dichloro-benzyl)-1H-imidazol-2-ylmethoxy]-pyridin-2-yl}-pyrrolidin-3-yl)-acetamide |

-continued

| Structure | Name |
|---|---|
| 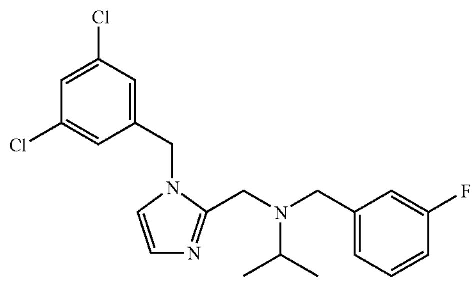 | [1-(3,5-Dichloro-benzyl)-1H-imidazol-2-ylmethyl]-(3-fluoro-benzyl)-isopropyl-amine |
| 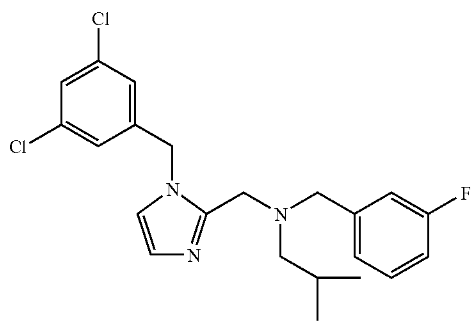 | [1-(3,5-Dichloro-benzyl)-1H-imidazol-2-ylmethyl]-(3-fluoro-benzyl)-isobutyl-amine |
| 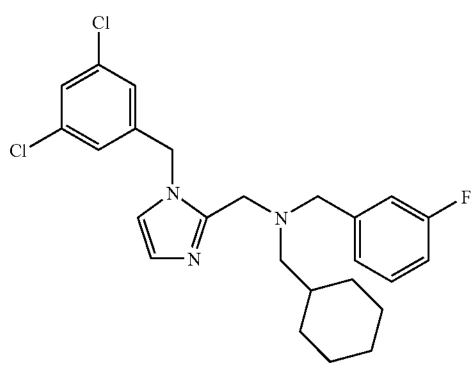 | Cyclohexylmethyl-[1-(3,5-dichloro-benzyl)-1H-imidazol-2-ylmethyl]-(3-fluoro-benzyl)-amine |
| 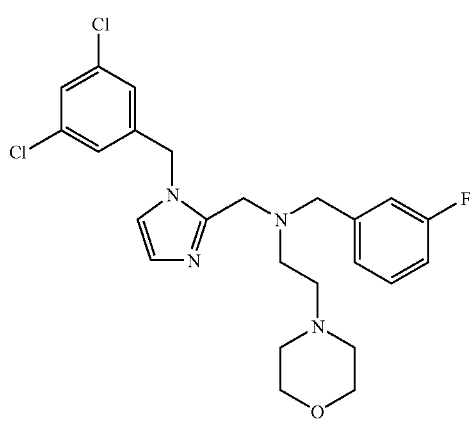 | [1-(3,5-Dichloro-benzyl)-1H-imidazol-2-ylmethyl]-(3-fluoro-benzyl)-(2-morpholin-4-yl-ethyl)-amine |

-continued

| Structure | Name |
|---|---|
| 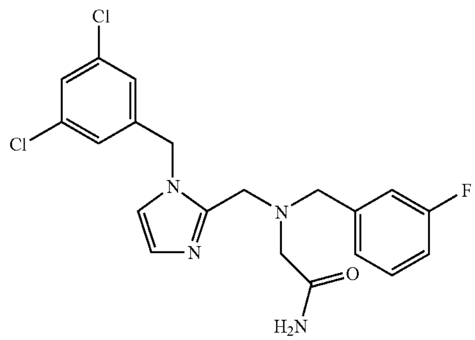 | 2-[[1-(3,5-Dichloro-benzyl)-1H-imidazol-2-ylmethyl]-(3-fluoro-benzyl)-amino]-acetamide |
| 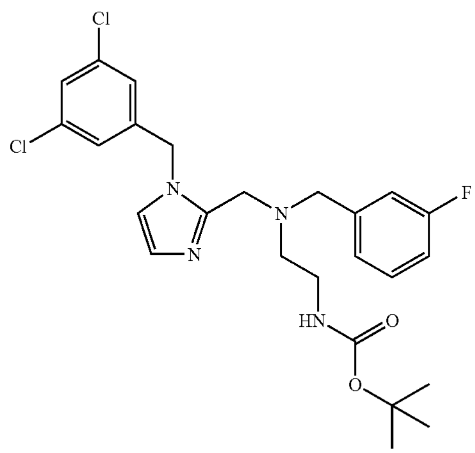 | {2-[[1-(3,5-Dichloro-benzyl)-1H-imidazol-2-ylmethyl]-(3-fluoro-benzyl)-amino]-ethyl}-carbamic acid tert-butyl ester |
| 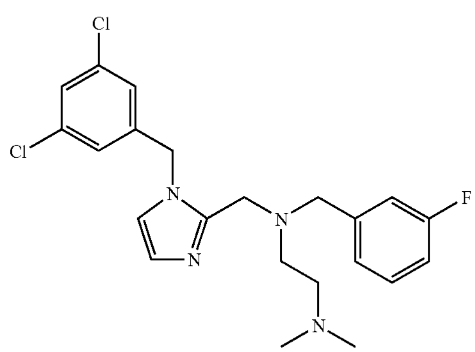 | N-[1-(3,5-Dichloro-benzyl)-1H-imidazol-2-ylmethyl]-N-(3-fluoro-benzyl)-N',N'-dimethyl-ethane-1,2-diamine |
| 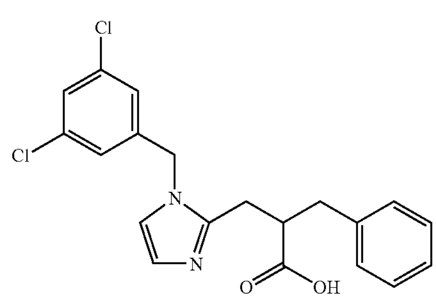 | 2-Benzyl-3-[1-(3,5-dichloro-benzyl)-1H-imidazol-2-yl]-propionic acid |

-continued

| Structure | Name |
|---|---|
| 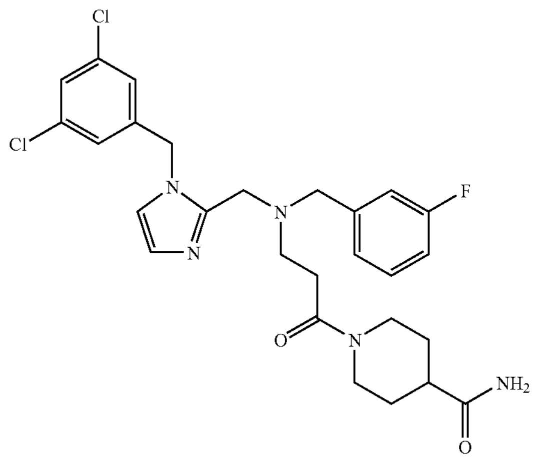 | 1-{3-[[1-(3,5-Dichloro-benzyl)-1H-imidazol-2-ylmethyl]-(3-fluoro-benzyl)-amino]-propionyl}-piperidine-4-carboxylic acid amide |
| 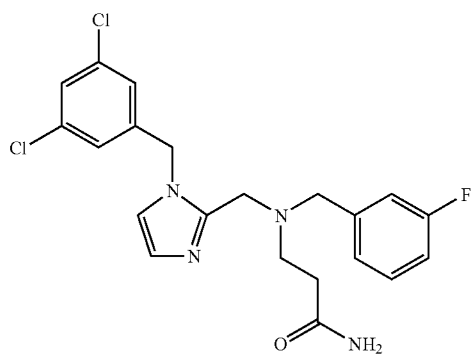 | 3-[[1-(3,5-Dichloro-benzyl)-1H-imidazol-2-ylmethyl]-(3-fluoro-benzyl)-amino]-propionamide |
| 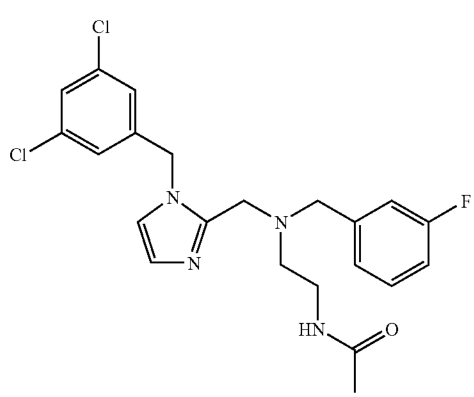 | N-{2-[[1-(3,5-Dichloro-benzyl)-1H-imidazol-2-ylmethyl]-(3-fluoro-benzyl)-amino]-ethyl}-acetamide |

| Structure | Name |
|---|---|
| 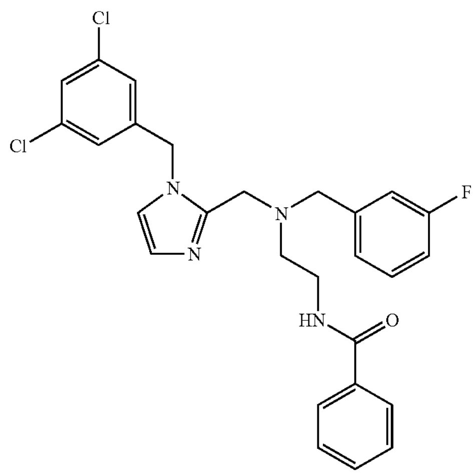 | N-{2-[[1-(3,5-Dichloro-benzyl)-1H-imidazol-2-ylmethyl]-(3-fluoro-benzyl)-amino]-ethyl}-benzamide |
| 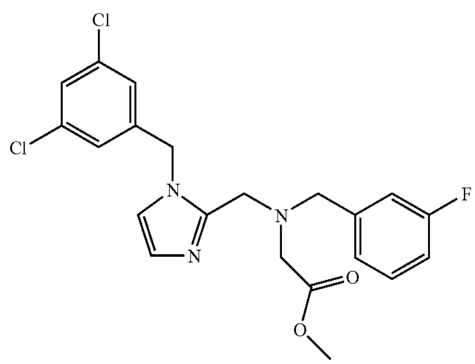 | [[1-(3,5-Dichloro-benzyl)-1H-imidazol-2-ylmethyl]-(3-fluoro-benzyl)-amino]-acetic acid methyl ester |
| 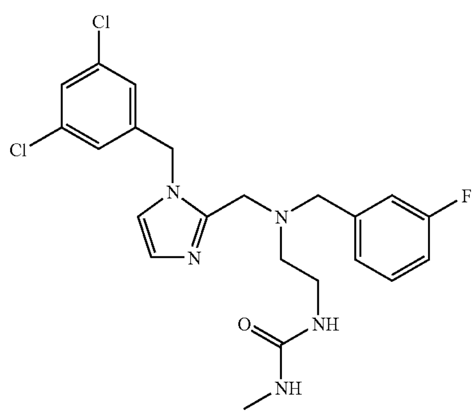 | 1-{2-[[1-(3,5-Dichloro-benzyl)-1H-imidazol-2-ylmethyl]-(3-fluoro-benzyl)-amino]-ethyl}-3-methyl-urea |
| 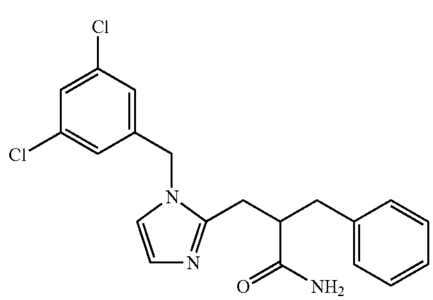 | 2-Benzyl-3-[1-(3,5-dichloro-benzyl)-1H-imidazol-2-yl]-propionamide |

| Structure | Name |
|---|---|
| 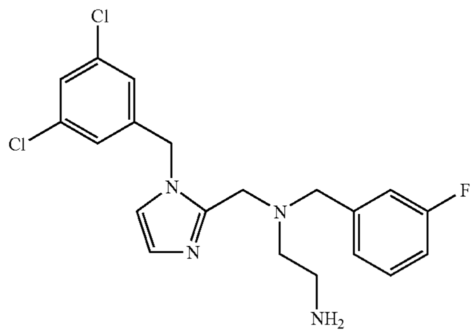 | N'-[1-(3,5-Dichloro-benzyl)-1H-imidazol-2-ylmethyl]-N'-(3-fluoro-benzyl)-ethane-1,2-diamine |
| 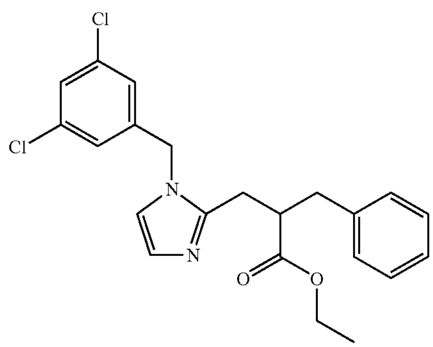 | 2-Benzyl-3-[1-(3,5-dichloro-benzyl)-1H-imidazol-2-yl]-propionic acid ethyl ester |
| 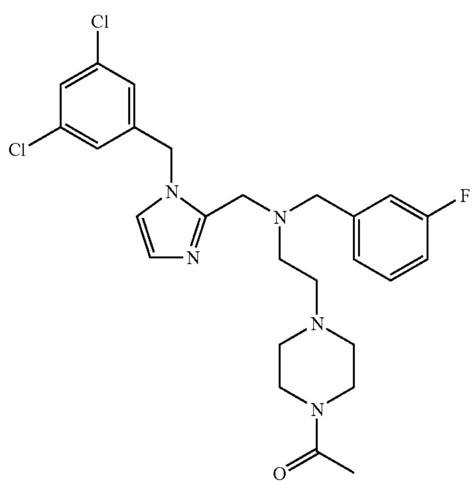 | 1-(4-{2-[[1-(3,5-Dichloro-benzyl)-1H-imidazol-2-ylmethyl]-(3-fluoro-benzyl)-amino]-ethyl}-piperazin-1-yl)-ethanone |
| 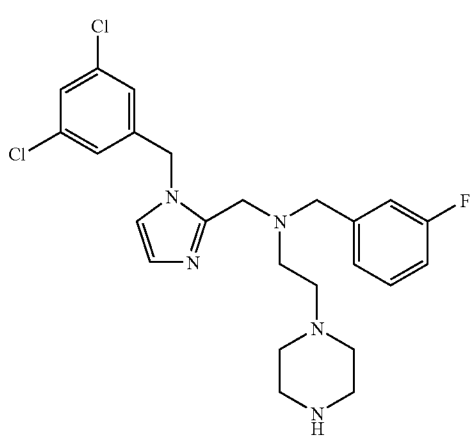 | [1-(3,5-Dichloro-benzyl)-1H-imidazol-2-ylmethyl]-(3-fluoro-benzyl)-(2-piperazin-1-yl-ethyl)-amine |

-continued

| Structure | Name |
| --- | --- |
| 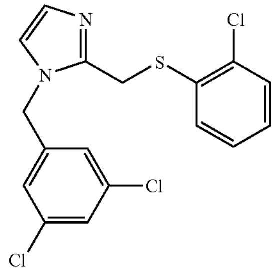 | 2-(2-Chloro-phenylsulfanylmethyl)-1-(3,5-dichloro-benzyl)-1H-imidazole |
|  | 2-(3-Chloro-phenylsulfanylmethyl)-1-(3,5-dichloro-benzyl)-1H-imidazole |
| 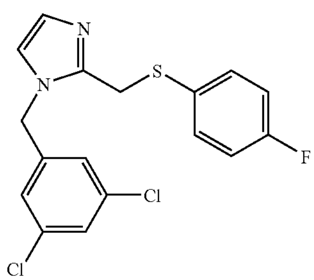 | 1-(3,5-Dichloro-benzyl)-2-(4-fluoro-phenoxymethyl)-1H-imidazole |
| 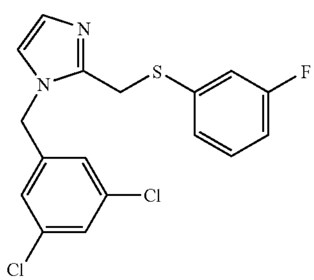 | 1-(3,5-Dichloro-benzyl)-2-(3-fluoro-phenylsulfanylmethyl)-1H-imidazole |
| 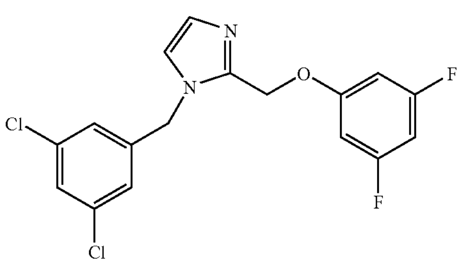 | 1-(3,5-Dichloro-benzyl)-2-(3,5-difluoro-phenoxymethyl)-1H-imidazole |

-continued
| Structure | Name |
|---|---|
| 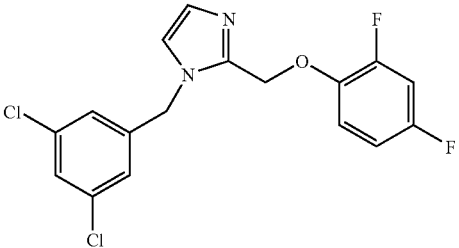 | 1-(3,5-Dichloro-benzyl)-2-(2,4-difluoro-phenoxymethyl)-1H-imidazole |
| 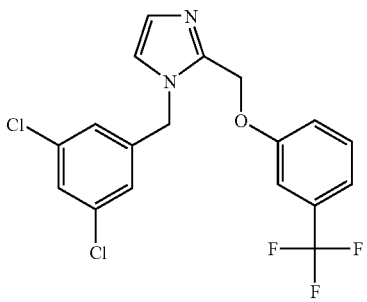 | 1-(3,5-Dichloro-benzyl)-2-(3-trifluoromethyl-phenoxymethyl)-1H-imidazole |
| 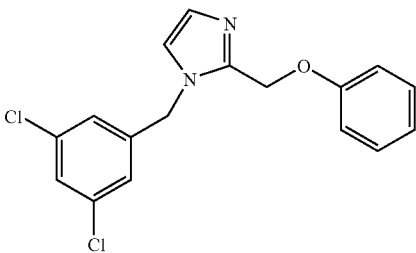 | 1-(3,5-Dichloro-benzyl)-2-phenoxymethyl-1H-imidazole |
| 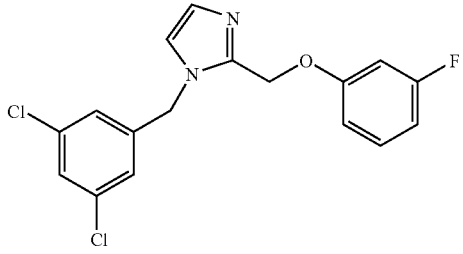 | 1-(3,5-Dichloro-benzyl)-2-(3-fluoro-phenoxymethyl)-1H-imidazole |
| 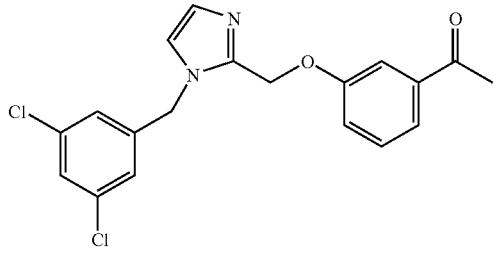 | 1-{3-[1-(3,5-Dichloro-benzyl)-1H-imidazol-2-ylmethoxy]-phenyl}-ethanone |
| 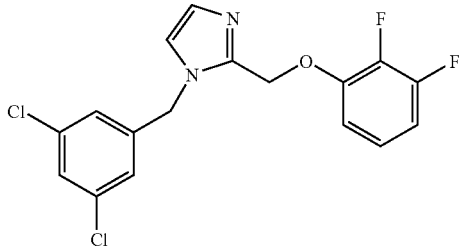 | 1-(3,5-Dichloro-benzyl)-2-(2,3-difluoro-phenoxymethyl)-1H-imidazole |

| Structure | Name |
|---|---|
| 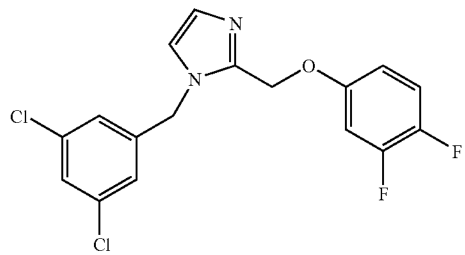 | 1-(3,5-Dichloro-benzyl)-2-(3,4-difluoro-phenoxymethyl)-1H-imidazole |
| 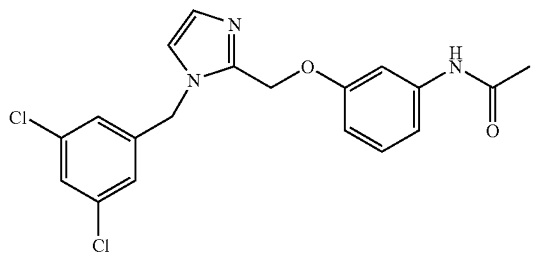 | N-{3-[1-(3,5-Dichloro-benzyl)-1H-imidazol-2-ylmethoxy]-phenyl}-acetamide |
| 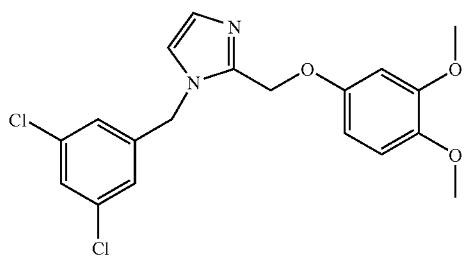 | 1-(3,5-Dichloro-benzyl)-2-(3,4-dimethoxy-phenoxymethyl)-1H-imidazole |
| 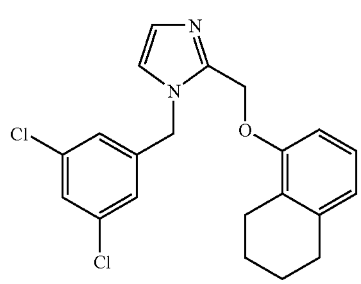 | 1-(3,5-Dichloro-benzyl)-2-(5,6,7,8-tetrahydro-naphthalen-1-yloxymethyl)-1H-imidazole |
| 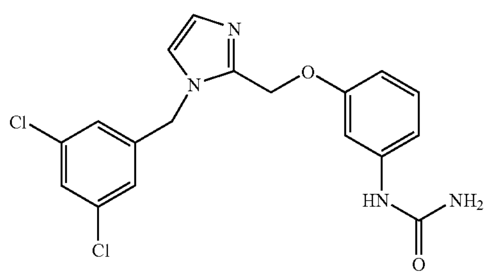 | {3-[1-(3,5-Dichloro-benzyl)-1H-imidazol-2-ylmethoxy]-phenyl}-urea |

| Structure | Name |
|---|---|
| 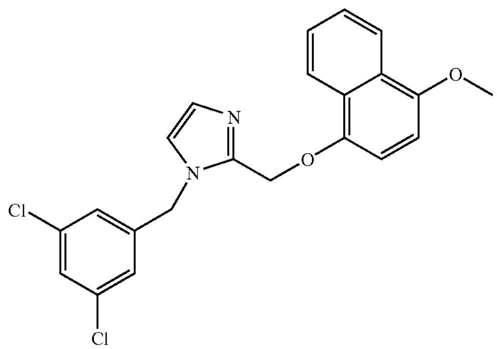 | 1-(3,5-Dichloro-benzyl)-2-[2-(4-methoxy-naphthalen-1-yloxy)-methyl]-1H-imidazole |
| 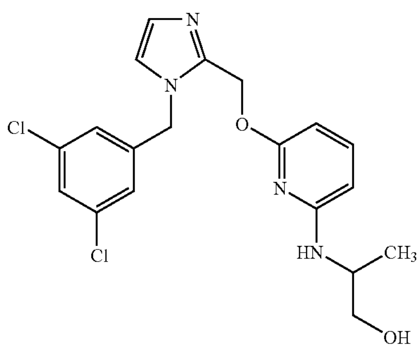 | 2-{6-[1-(3,5-Dichloro-benzyl)-1H-imidazol-2-ylmethoxy]-pyridin-2-ylamino}-propan-1-ol |
| Chiral | (S)-2-{6-[1-(3,5-Dichloro-benzyl)-1H-imidazol-2-ylmethoxy]-pyridin-2-ylamino}-4-methyl-pentan-1-ol |
| 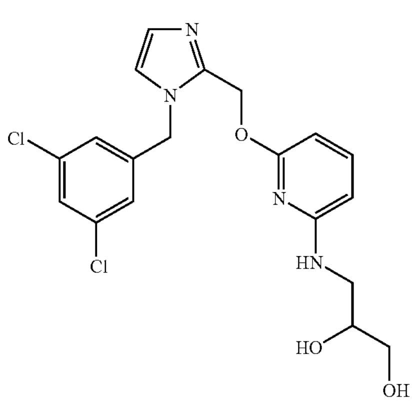 | 3-{6-[1-(3,5-Dichloro-benzyl)-1H-imidazol-2-ylmethoxy]-pyridin-2-ylamino}-propane-1,2-diol |

| Structure | Name |
|---|---|
| 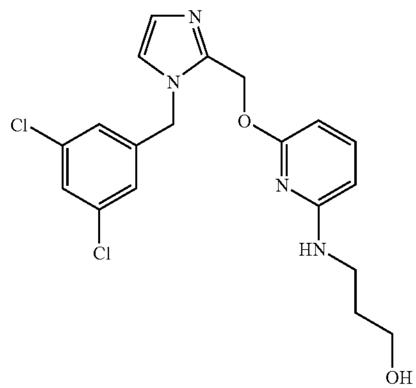 | 3-{6-[1-(3,5-Dichloro-benzyl)-1H-imidazol-2-ylmethoxy]-pyridin-2-ylamino}-propan-1-ol |
| 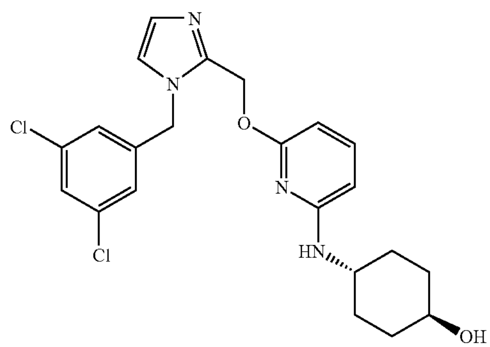 | trans-4-{6-[1-(3,5-Dichloro-benzyl)-1H-imidazol-2-ylmethoxy]-pyridin-2-ylamino}-cyclohexanol |
| 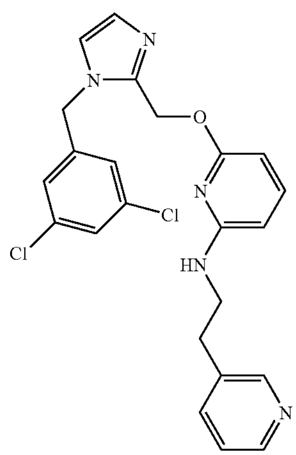 | {6-[1-(3,5-Dichloro-benzyl)-1H-imidazol-2-ylmethoxy]-pyridin-2-yl}-(2-pyridin-3-yl-ethyl)-amine |
| 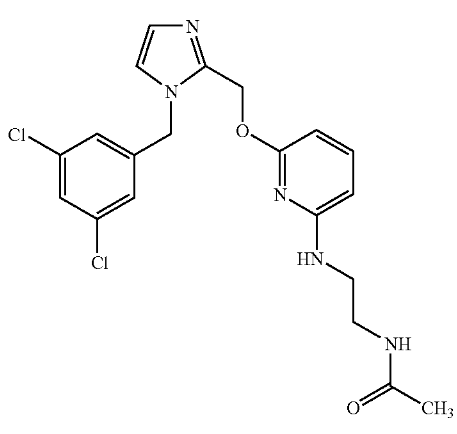 | N-(2-{6-[1-(3,5-Dichloro-benzyl)-1H-imidazol-2-ylmethoxy]-pyridin-2-ylamino}-ethyl)-acetamide |

-continued

| Structure | Name |
|---|---|
| | 6-[1-(3,5-Dichloro-benzyl)-1H-imidazol-2-ylmethoxy]-3',4',5',6',1",2",3",4",5",6"-decahydro-2'H-[2,1';4',4"]terpyridine |
| Chiral | {6-[1-(3,5-Dichloro-benzyl)-1H-imidazol-2-ylmethoxy]-pyridin-2-yl}-(S)-1-pyrrolidin-2-ylmethyl-amine |
| 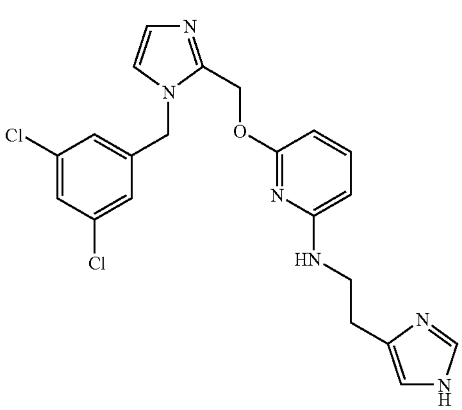 | {6-[1-(3,5-Dichloro-benzyl)-1H-imidazol-2-ylmethoxy]-pyridin-2-yl}-[2-(1H-imidazol-4-yl)-ethyl]-amine |

| Structure | Name |
|---|---|
| 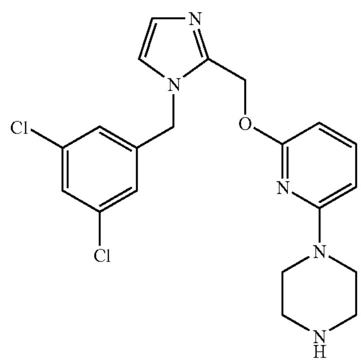 | 1-{6-[1-(3,5-Dichloro-benzyl)-1H-imidazol-2-ylmethoxy]-pyridin-2-yl}-piperazine |
| 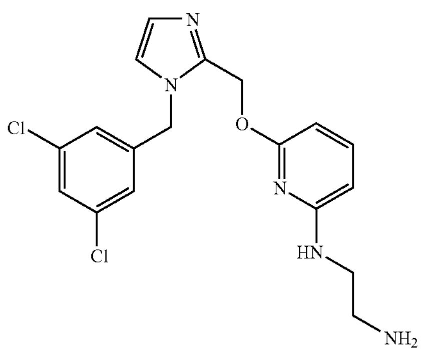 | N1-{6-[1-(3,5-Dichloro-benzyl)-1H-imidazol-2-ylmethoxy]-pyridin-2-yl}-ethane-1,2-diamine |
| 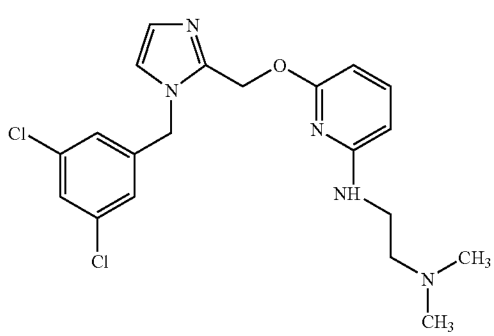 | N'-{6-[1-(3,5-Dichloro-benzyl)-1H-imidazol-2-ylmethoxy]-pyridin-2-yl}-N,N-dimethyl-ethane-1,2-diamine |
| 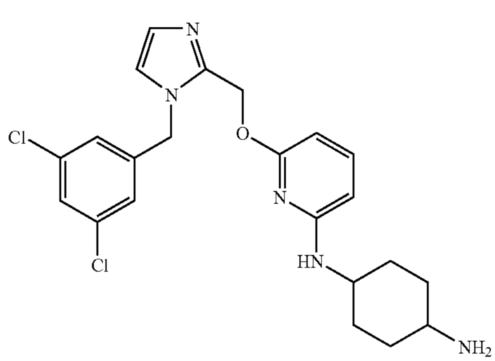 | N-{6-[1-(3,5-Dichloro-benzyl)-1H-imidazol-2-ylmethoxy]-pyridin-2-yl}-cyclohexane-1,4-diamine |

| Structure | Name |
|---|---|
| 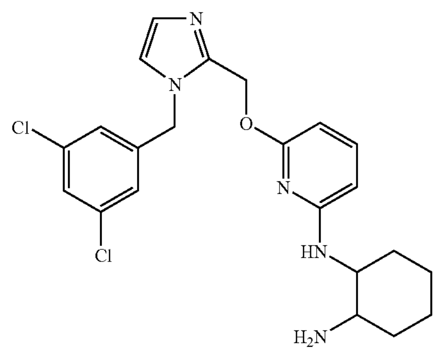 | N-{6-[1-(3,5-Dichloro-benzyl)-1H-imidazol-2-ylmethoxy]-pyridin-2-yl}-cyclohexane-1,2-diamine |
| 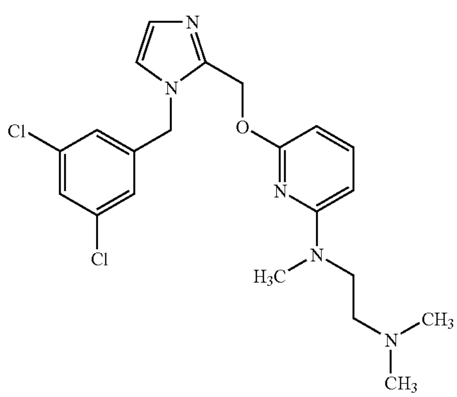 | N-{6-[1-(3,5-Dichloro-benzyl)-1H-imidazol-2-ylmethoxy]-pyridin-2-yl}-N',N',N'-trimethyl-ethane-1,2-diamine |
| 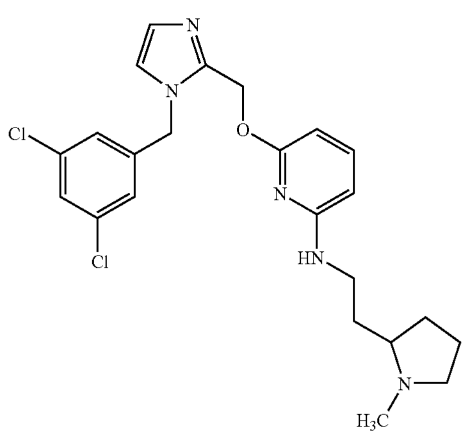 | {6-[1-(3,5-Dichloro-benzyl)-1H-imidazol-2-ylmethoxy]-pyridin-2-yl}-[2-(1-methyl-pyrrolidin-2-yl)-ethyl]-amine |
| 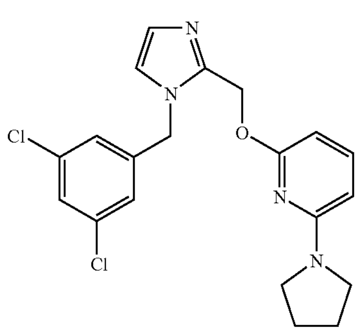 | 2-[1-(3,5-Dichloro-benzyl)-1H-imidazol-2-ylmethoxy]-6-pyrrolidin-1-yl-pyridine |

| Structure | Name |
|---|---|
| 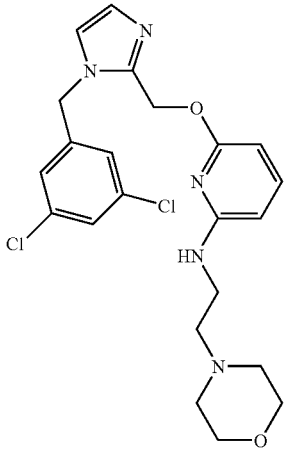 | {6-[1-(3,5-Dichloro-benzyl)-1H-imidazol-2-ylmethoxy]-pyridin-2-yl}-(2-morpholin-4-yl-ethyl)-amine |
| 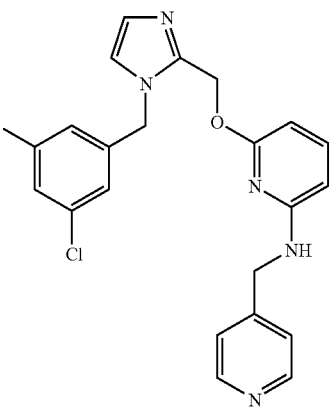 | {6-[1-(3,5-Dichloro-benzyl)-1H-imidazol-2-ylmethoxy]-pyridin-2-yl}-pyridin-4-ylmethyl-amine |
| 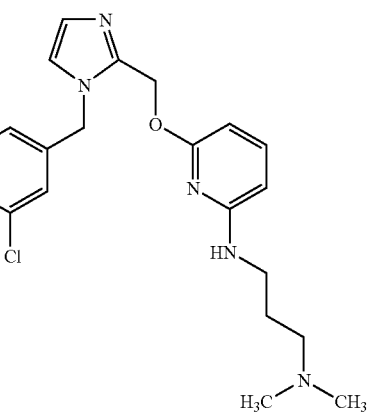 | N'-{6-[1-(3,5-Dichloro-benzyl)-1H-imidazol-2-ylmethoxy]-pyridin-2-yl}-N,N-dimethyl-propane-1,3-diamine |

| Structure | Name |
|---|---|
| 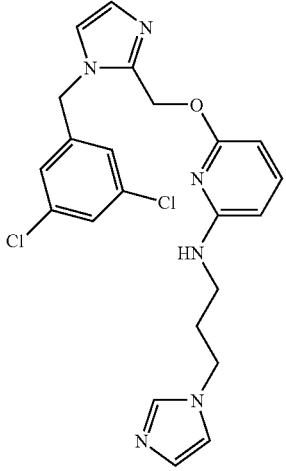 | {6-[1-(3,5-Dichloro-benzyl)-1H-imidazol-2-ylmethoxy]-pyridin-2-yl}-(3-imidazol-1-yl-propyl)-amine |
| 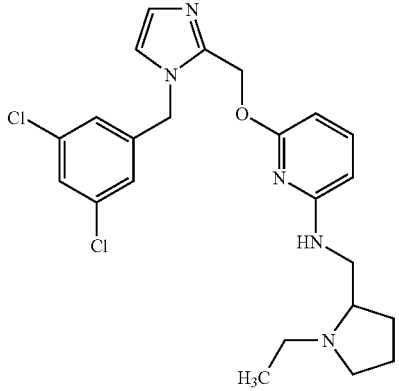 | {6-[1-(3,5-Dichloro-benzyl)-1H-imidazol-2-ylmethoxy]-pyridin-2-yl}-(1-ethyl-pyrrolidin-2-ylmethyl)-amine |
| 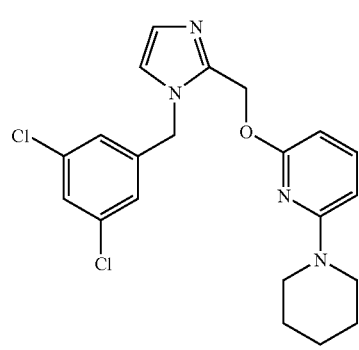 | 6'-[1-(3,5-Dichloro-benzyl)-1H-imidazol-2-ylmethoxy]-3,4,5,6-tetrahydro-2H-[1,2']bipyridinyl |

| Structure | Name |
|---|---|
| (structure shown) | N-(1-{6-[1-(3,5-Dichloro-benzyl)-1H-imidazol-2-ylmethoxy]-pyridin-2-yl}-pyrrolidin-3-yl)-N-methyl-acetamide |

In yet an even further embodiment there are provided the following compounds:
2-(3-Chloro-5-methoxy-phenoxymethyl)-1-(3,5-dichloro-benzyl)-1H-imidazole,
[1-(3,5-Dichloro-benzyl)-1H-imidazol-2-ylmethyl]-(3-fluoro-benzyl)-amine,
[1-(3,5-Dichloro-benzyl)-1H-imidazol-2-ylmethyl]-(3,5-difluoro-benzyl)-amine,
{2-[[1-(3,5-Dichloro-benzyl)-1H-imidazol-2-ylmethyl]-(3-fluoro-benzyl)-amino]-ethyl}-carbamic acid tert-butyl ester,
3-[[1-(3,5-Dichloro-benzyl)-1H-imidazol-2-ylmethyl]-(3-fluoro-benzyl)-amino]-propionamide,
N-{2-[[1-(3,5-Dichloro-benzyl)-1H-imidazol-2-ylmethyl]-(3-fluoro-benzyl)-amino]-ethyl}-acetamide,
$N^1$-[1-(3,5-Dichloro-benzyl)-1H-imidazol-2-ylmethyl]-$N^1$-(3-fluoro-benzyl)-ethane-1,2-diamine,
(S)-1-{6-[1-(3,5-Dichloro-benzyl)-1H-imidazol-2-ylmethoxy]-pyridin-2-yl}-pyrrolidine-2-carboxylic acid amide,
{6-[1-(3,5-Dichloro-benzyl)-1H-imidazol-2-ylmethoxy]-pyridin-2-yl}-pyridin-4-ylmethyl-amine,
N-(1-{6-[1-(3,5-Dichloro-benzyl)-1H-imidazol-2-ylmethoxy]-pyridin-2-yl}-pyrrolidin-3-yl)-N-methyl-acetamide,
N-(2-{6-[1-(3,5-Dichloro-benzyl)-1H-imidazol-2-ylmethoxy]-pyridin-2-ylamino}-ethyl)-acetamide,
N-{6-[1-(3,5-Dichloro-benzyl)-1H-imidazol-2-ylmethoxy]-pyridin-2-yl}-cyclohexane-1,2-diamine,
{6-[1-(3,5-Dichloro-benzyl)-1H-imidazol-2-ylmethoxy]-pyridin-2-yl}-[2-(1-methyl-pyrrolidin-2-yl)-ethyl]-amine,
{6-[1-(3,5-Dichloro-benzyl)-1H-imidazol-2-ylmethoxy]-pyridin-2-yl}-(1-ethyl-pyrrolidin-2-ylmethyl)-amine,
{6-[1-(3,5-Dichloro-benzyl)-1H-imidazol-2-ylmethoxy]-pyridin-2-yl}-(3-imidazol-1-yl-propyl)-amine, and
N-{6-[1-(3,5-Dichloro-benzyl)-1H-imidazol-2-ylmethoxy]-pyridin-2-yl}-N',N',N'-trimethyl-ethane-1,2-diamine.

The present invention also includes all the pharmaceutically acceptable salts and esters of the compounds of the formula I. The pharmaceutically acceptable salts include any pharmaceutically-acceptable acid addition salts and pharmaceutically-acceptable base addition salts as would be understood by one skilled in the art. The compounds of the present invention therefore include the free base or acid thereof, their pharmaceutically acceptable salts and esters and also may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the present invention.

Some of the compounds of the present invention can exist in more than one tautomeric form, and the present invention therefore includes all such tautomers.

In general, all tautomeric forms and isomeric forms and mixtures, whether individual geometric isomers or stereoisomers or racemic or non-racemic mixtures of isomers, of a chemical structure or compound is intended, unless the specific stereochemistry or isomeric form is specifically indicated in the compound name or structure.

General Synthetic Methods

Compounds of the invention may be prepared by the general methods described below. Typically, reaction progress may be monitored by thin layer chromatography (TLC) if desired. If desired, intermediates and products may be purified by chromatography on silica gel and/or recrystallization, and characterized by one or more of the following techniques: NMR, mass spectroscopy and melting point. Starting materials and reagents are either commercially available or may be prepared by one skilled in the art from commercially available materials using methods described in the chemical literature.

Compounds of formula I having X=$CH_2$, Y=O or S and Z=a bond may be prepared by the method described below and outlined in Scheme I.

Scheme I

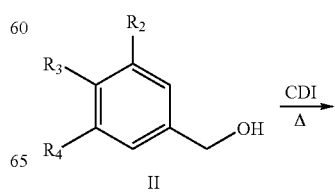

II

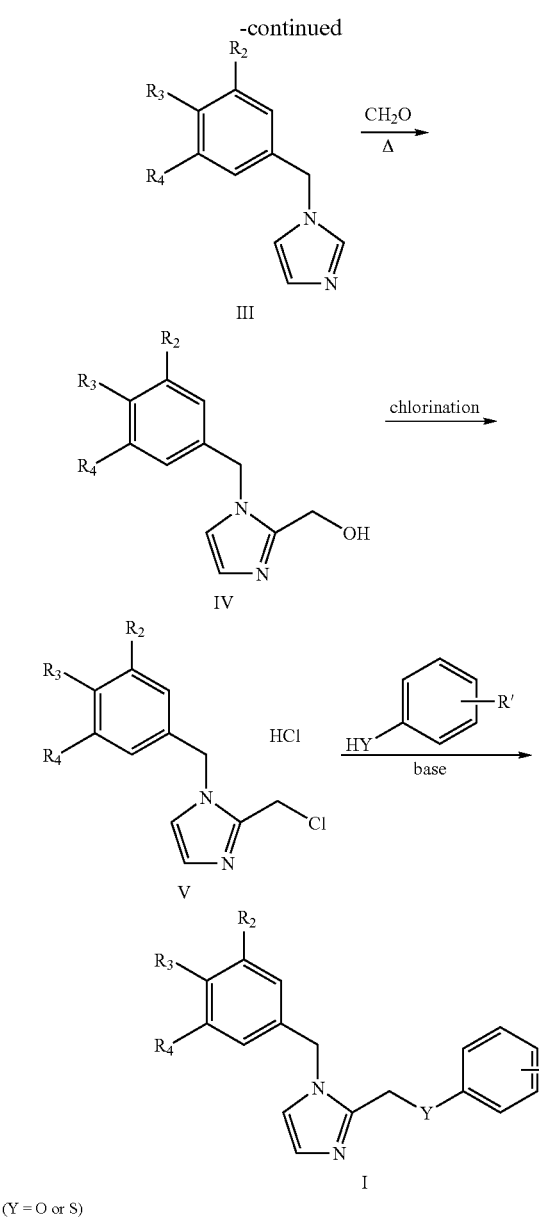

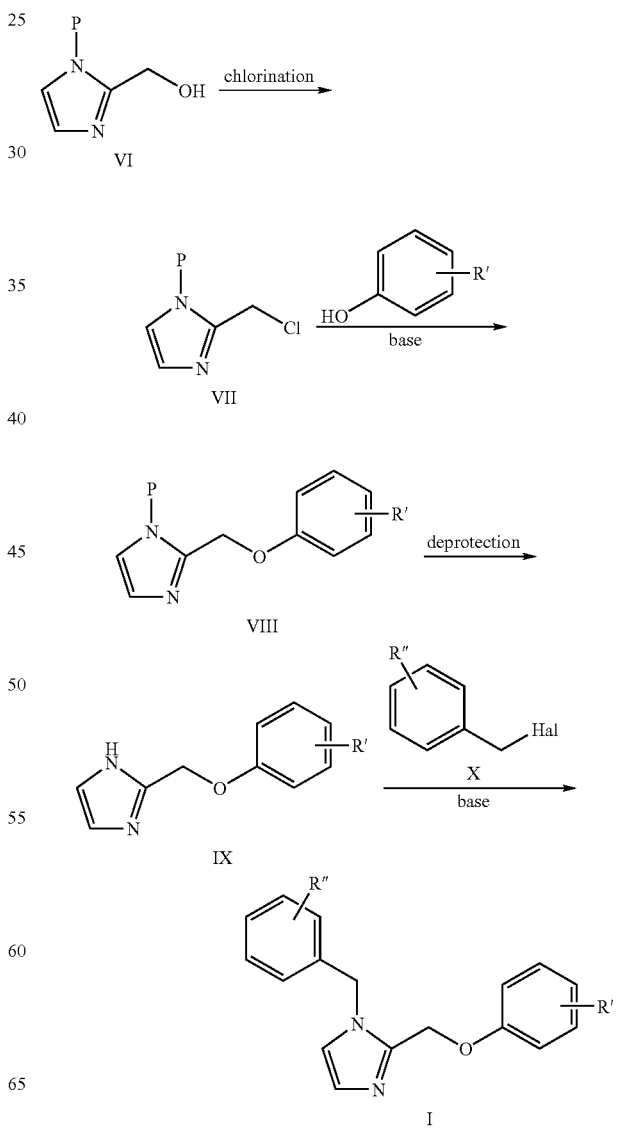

prepare the corresponding compound with Y=NH. The nitrogen may be further substituted by methods known in the art to obtain compounds with Y=NR₇.

An alternate procedure is illustrated in Scheme II. In this procedure a protected hydroxymethylimidazole VI is chlorinated analogous to the chlorination method of intermediate IV as described above to provide VII. An example of a suitable protecting group is a 2-tetrahydrofuranyl group. Intermediate VII is then reacted with the desired substituted phenol analogous to the reaction of Intermediate V with a substituted phenol as described above to provide VIII. The protecting group is then removed using conditions known in the art for the particular protecting group used, for example by treating with dilute HCl if the 2-tetrahydrofuranyl protecting group is used. The resulting substituted imidazole, IX, is then reacted with the desired substituted benzyl halide X, where Hal is Cl, Br or I, in the presence of a base such as potassium carbonate in a suitable solvent such as DMF or DMSO to provide the desired compound of formula I.

As illustrated above, a substituted benzyl alcohol (II) is heated with 1,1-carbonyldiimidazole in a suitable solvent such as DMSO to provide substituted imidazole III. This is reacted with aqueous formaldehyde, preferably while heating in a sealed tube, to provide the hydroxymethylimidazole IV. Intermediate IV is then reacted with a suitable chlorinating agent such as thionyl chloride, in a suitable solvent such as methylene chloride or chloroform to provide the chloromethyl intermediate V, which may be isolated as the HCl salt. This is then reacted with the desired substituted phenol in a suitable solvent such as DMSO or DMF, in the presence of a base such as potassium carbonate, to provide the desired compound of formula I. One may use a substituted thiophenol in place of a substituted phenol in the final step described above to obtain a compound of formula I having X=CH₂, Y=S and Z=a bond. A substituted aniline may be used to Compounds of formula I having X and Z=CH$_2$ and Y=O may be prepared as illustrated in Scheme III.

Scheme III

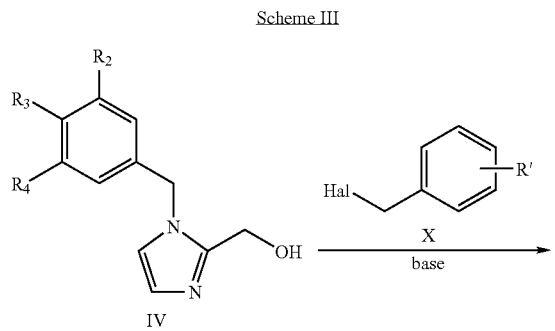

IV

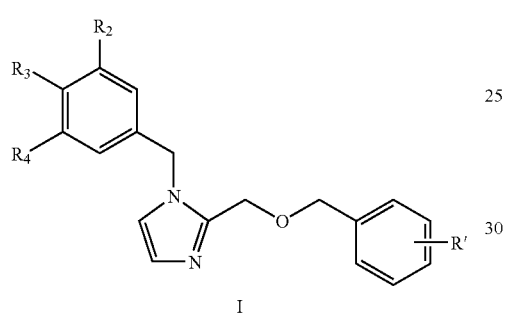

I

As illustrated above, intermediate IV (Scheme I) is reacted with a substituted benzyl halide X (Hal=Br, Cl or I) in the presence of a base such as sodium hydride in a suitable solvent such as DMF to provide the desired compound of formula I.

Compounds of formula I having X=CH$_2$, Y=an optionally substituted amine (NR') and Z=CH$_2$ may be prepared as illustrated in Scheme IV. Reaction of intermediate V (Scheme I) with the desired amine, XI, in a suitable solvent such as DMF and optionally in the presence of a base such as triethylamine provides the desired compound of formula I. The corresponding compounds where Y=S can be prepared by using an optionally substituted benzylmercapto compound as a reactant instead of the benzylamine compound XI in Scheme IV.

Scheme IV

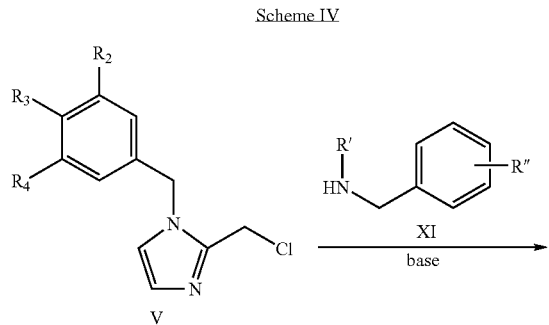

V

-continued

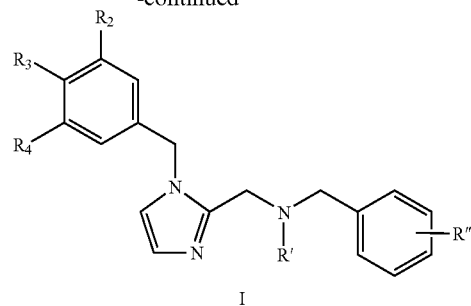

I

In an alternate procedure illustrated in Scheme V, one may prepare compounds having X=a substituted methylene group (CH(R''')), Y=NH and Z=CH$_2$—In this procedure, one reacts the aldehyde intermediate XII (prepared by oxidation of intermediate IV (from Scheme I) with a suitable oxidizing agent such as MnO$_2$) with the desired benzyl amine XI' in refluxing benzene with removal of water by the presence of molecular sieves or a Dean-Stark trap, to provide an intermediate imine, which is directly reacted with a Grignard reagent (R'" MgX, X=Br or I) in a suitable solvent to provide the desired compound of formula I.

Scheme V

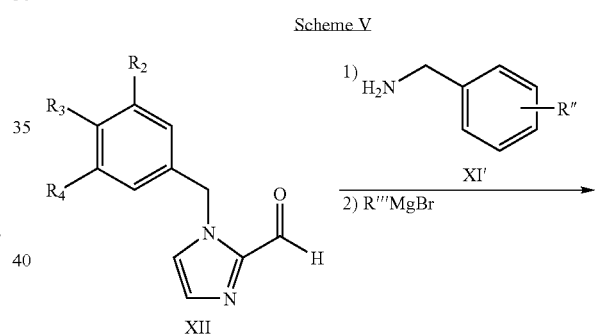

XII

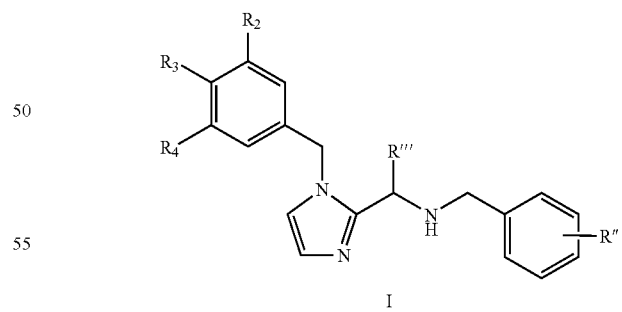

I

To obtain compounds of formula I with X=CH$_2$, Y=NR' and Z=CH$_2$, one may react intermediate XII (from Scheme V) with XI in a suitable solvent such as methylene chloride in the presence of a suitable reducing agent such as sodium triacetoxyborohydride or sodium cyanoborohydride to provide the desired compound of formula I as illustrated in Scheme VI.

Scheme VI

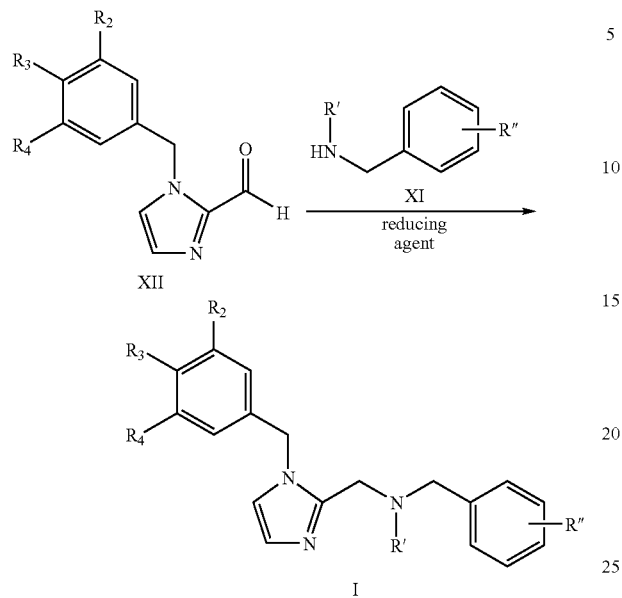

Compounds of formula I having X═NH and Y═CH$_2$ may be prepared as illustrated in Scheme VII. Using this method, a substituted benzyl halide XIII (Hal═Cl, Br or I) is reacted with 2-nitroimidazole in the presence of a base such as triethylamine, in a suitable solvent such as DMF to provide intermediate XIV. Intermediate XIV is treated with a suitable reducing agent such as Fe and acetic acid to provide XV. Intermediate XV is then treated with the acid chloride R$_1$ZC(O)Cl to provide the desired amide XVI (X═NH, Y═C(O). Reduction with a suitable reducing agent such as lithium aluminum hydride in a suitable solvent such as THF provides the desired compound of formula I with X═NH and Y═CH$_2$.

Scheme VII

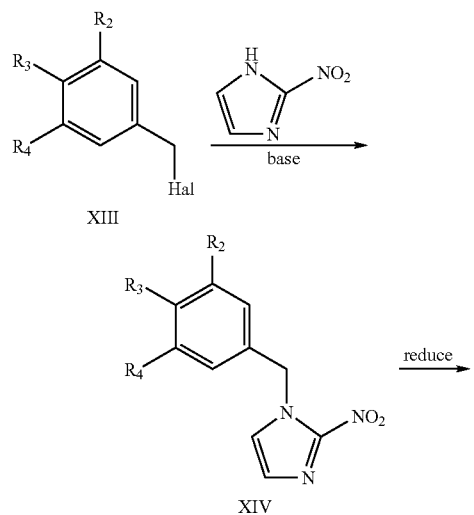

Compounds of formula I having Y═CH(R) where R is a carboxylic acid or carboxylic acid derivative may be prepared as illustrated in Scheme VIII.

Scheme VIII

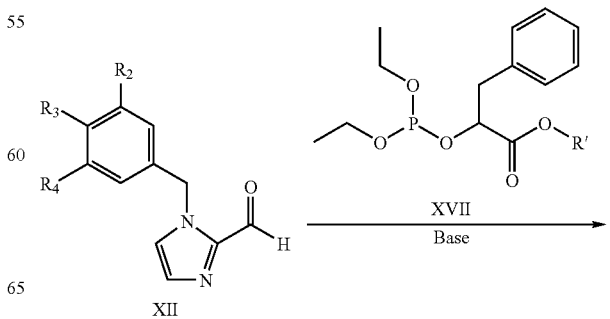

-continued

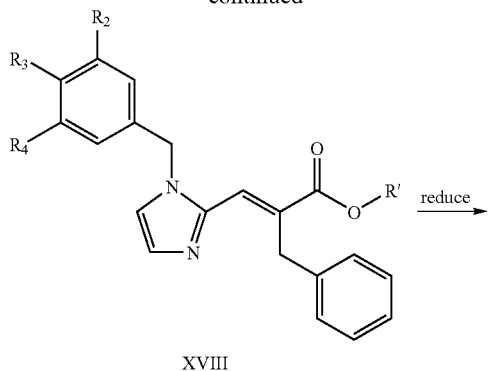

XVIII

Scheme IX

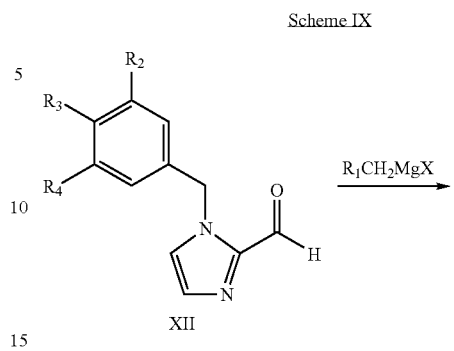

XII

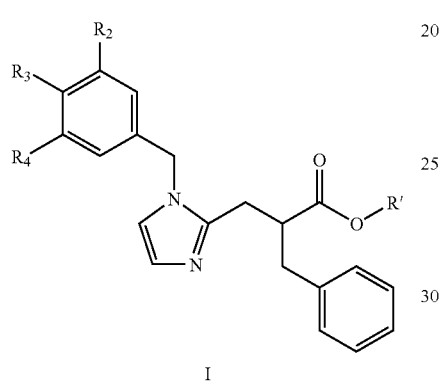

I

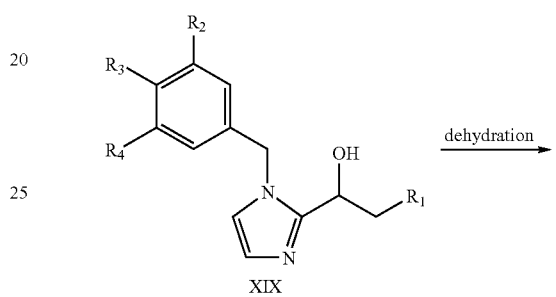

XIX

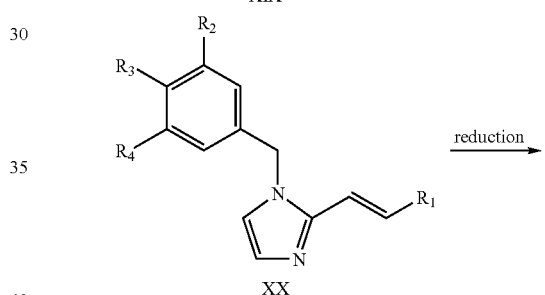

XX

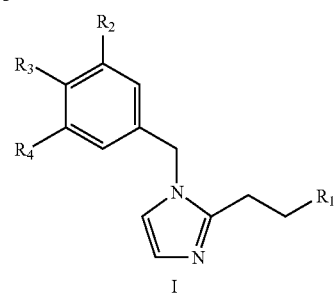

I (X = Y = CH₂, Z = bond)

As illustrated above, aldehyde XII is treated with the phosphonoacetate XVII in the presence of a base such as LiOH in a suitable solvent such as THF to provide the olefin ester XVIII. Intermediate XVIII is then treated with a reducing agent such as Raney nickel in a suitable solvent such as ethanol to provide the compound of formula I (Y=CH(R), R=CO₂R' where R' is an alkyl group such as methyl or ethyl). The ester may be modified by methods well known in the art to prepare the carboxylic acid. If one desires a compound of formula (I) having X=Y=Z=CH₂, one may hydrolyze the ester intermediate XVIII and decarboxylate the resulting carboxylic acid by methods known in the art such as by heating in quinoline in the presence of copper, followed by reduction of the resulting olefin, for example by treating with hydrogen in the presence of a catalyst such as palladium on carbon.

Additional compounds of the invention may be made by methods known in the art. For example, as illustrated in Scheme IX, compounds of formula I having X=CH₂, Y=CH₂ and Z=a bond may be prepared by reaction of intermediate XII with a Grignard reagent R₁CH₂MgX, where X is a halogen to provide alcohol XIX. Dehydration, for example by treatment with acid and reduction of the intermediate olefin XX, for example by treatment with hydrogen in the presence of palladium on carbon provides the compound of formula (I) having X=CH₂, Y=CH₂ and Z=a bond.

As illustrated in Scheme X, compounds of formula I having X=CH₂, Y=O, Z=a bond and R₁=a substituted pyridine may be prepared by reaction of intermediate IV with a 2,6-dihalopyridine, preferably a 2,6-difluoropyridine, in the presence of a base such as NaH, in a suitable solvent such as DMF, to provide XXI. This intermediate may be further modified by methods known in the art to prepare additional compounds of formula I. For example, treatment with a substituted amine HNR'R" in a suitable solvent provides the compound of formula I with X=CH₂, Y=O, Z=a bond and R₁=a pyridine substituted with an amine.

Scheme X

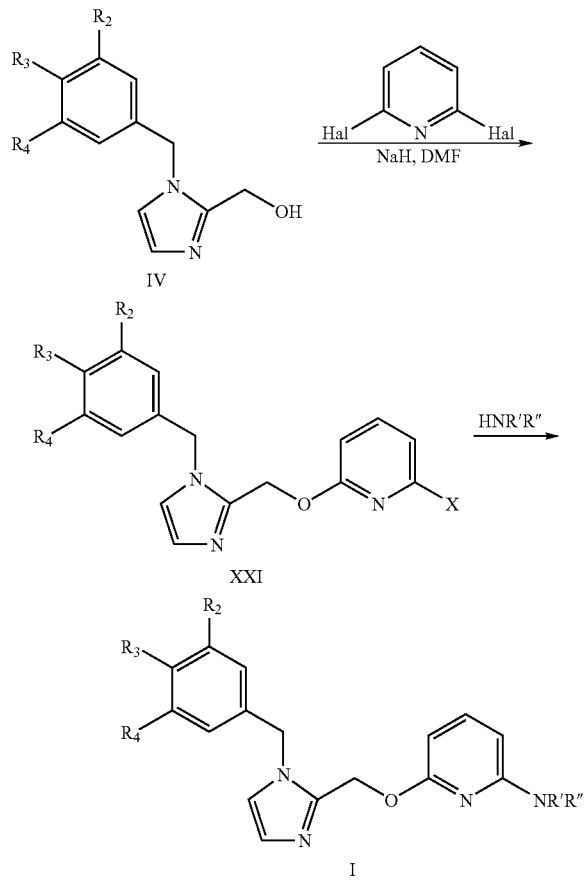

(X = CH₂, Y = O, Z = bond,
R₁ = substituted pyridine)

SYNTHETIC EXAMPLES

Example 1

3-[1-(3,5-Dichloro-benzyl)-1H-imidazol-2-yl-methoxy]-phenol

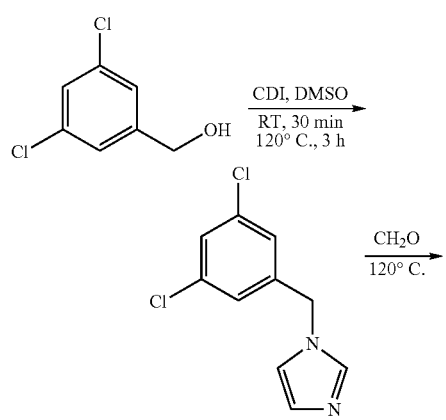

To a mixture of 1,1'-carbonyldiimidazole (25.2 g, 155.3 mmol) and DMSO (50 mL) was added 3,5-dichlorobenzyl alcohol (25.0 g, 141.2 mmol). The mixture was stirred at ambient temperature for 30 min and then heated at 120° C. for 3 h until $CO_2$ gas evolution ceased. After cooling, the mixture was poured into water (300 mL) while stirring whereupon a solid formed. The solid was filtered and washed with water. The crude 1-(3,5-dichloro-benzyl)-1H-imidazole (30.0 g, 93%) was obtained as an off-white solid: ESI MS m/z 227 $[C_{10}H_8Cl_2N_2+H]^+$.

A mixture of the above dichlorobenzylimidazole (30.0 g, 132.2 mmol) and 37% aqueous formaldehyde (50 mL) was heated with stirring in a sealed tube reaction vessel at 120° C. for 24 h. After cooling, the mixture was poured onto a solution of 0.4 N NaOH (400 mL) and stirred for 2 h. The resulting solid was filtered and washed with water. Crystallization of the crude material (MeOH/H₂O) provided [1-(3,5-dichloro-benzyl)-1H-imidazol-2-yl]-methanol (26 g, 77%) as an off-white solid: ESI MS m/z 257 $[C_{11}H_{10}Cl_2N_2O+H]^+$.

[1-(3,5-Dichloro-benzyl)-1H-imidazol-2-yl]-methanol (1.7 g, 6.63 mmol) was dissolved in chloroform (16 mL) and diluted with thionyl chloride (2.9 mL, 40 mmol). The reaction was warmed to reflux. After 4 h, the reaction was concentrated to yield 1.95 g of 2-chloromethyl-1-(3,5-dichlorobenzyl)-1H-imidazole hydrochloride as a pale yellow solid (95%).

To a mixture of 2-chloromethyl-1-(3,5-dichlorobenzyl)-1H-imidazole hydrochloride (156 mg, 0.5 mmol), resorcinol (330 mg, 3.0 mmol) and DMSO (1 mL) was added $K_2CO_3$ (691 mg, 5.0 mmol). The reaction was stirred at ambient temperature for 14 h before diluting with water (20 mL). A solution of 1N HCl was added until the mixture was made only slightly basic (pH 8) before extracting with EtOAc (30 mL). The EtOAc phase was washed with water (10 mL), dried (Na$_2$SO$_4$) and concentrated in vacuo. The residue was purified by column chromatography (silica gel, 1:2 to 1:3 hexane/EtOAc then 100% EtOAc) to provide the title compound (113 mg, 65%) as an off-white solid: ESI MS m/z 349 [C$_{17}$H$_{14}$Cl$_2$N$_2$O$_2$+H]$^+$.

Example 2

1-[1-(3,5-Dichloro-benzyl)-1H-imidazol-2-yl]-2-(3-methoxy-phenyl)-ethanone

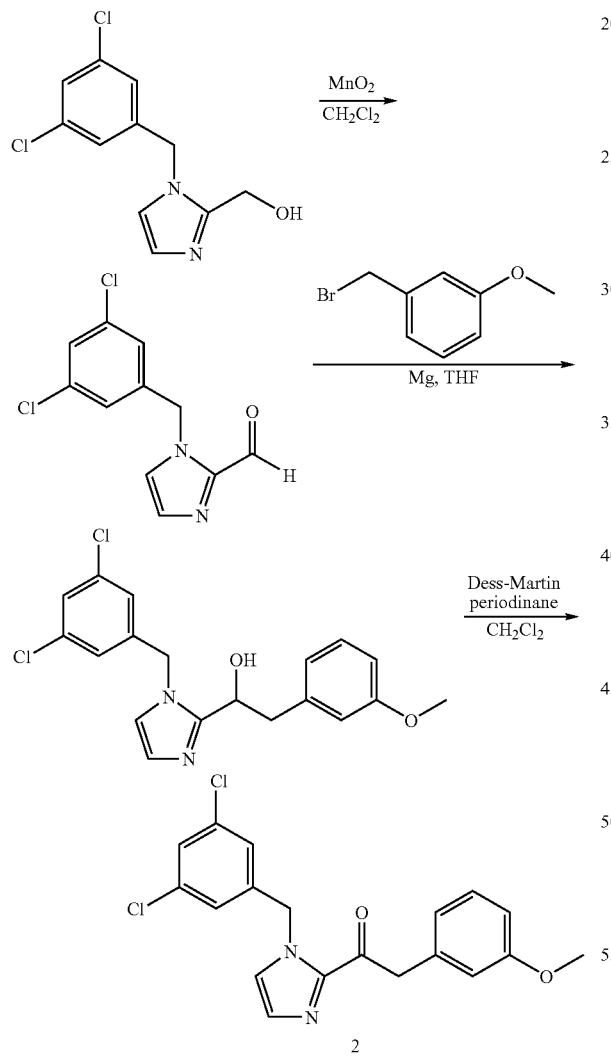

To a suspension of [1-(3,5-dichloro-benzyl)-1H-imidazol-2-yl]-methanol (see Example 1) (2.02 g, 7.88 mmol) in CH$_2$Cl$_2$ (10 mL) at ambient temperature was added MnO$_2$ (6.78 g, 78.0 mmol). The mixture was stirred for 5 h then filtered through a diatomaceous earth pad. Removal of the solvent in vacuo provided 1-(3,5-dichloro-benzyl)-1H-imidazole-2-carbaldehyde (1.80 g, 90%) as a white solid: ESI MS m/z 225 [C$_{11}$H$_8$Cl$_2$N$_2$O+H]$^+$.

A mixture of 3-methoxy-benzylbromide (40 mg, 0.2 mmol), magnesium turnings (172 mg, 7.1 mmol) and a small crystal of iodine in dry THF (0.6 mL) was heated at 40° C. until an exothermic reaction to initiated. A solution containing a mixture of 1-(3,5-dichloro-benzyl)-1H-imidazole-2-carbaldehyde (255 mg, 1.0 mmol) and 3-methoxy-benzylbromide (241 mg, 1.2 mmol) in THF (2.5 mL) was then added dropwise to the stirred reaction mixture. After the addition was complete, the mixture was poured into cold water (20 mL) and extracted with CH$_2$Cl$_2$ (2×30 mL). The combined CH$_2$Cl$_2$ extracts were dried over Na$_2$SO$_4$ and concentrated in vacuo. The residue was purified by column chromatography (silica gel, 20:1 CH$_2$Cl$_2$/iPrOH) to provide the desired 1-[1-(3,5-dichloro-benzyl)-1H-imidazol-2-yl]-2-(3-methoxy-phenyl)-ethanol (230 mg, 61%) as an off-white solid: ESI MS m/z 377 [C$_{19}$H$_{18}$Cl$_2$N$_2$O$_2$+H]$^+$.

To a solution of 1-[1-(3,5-Dichloro-benzyl)-1H-imidazol-2-yl]-2-(3-methoxy-phenyl)-ethanol (40 mg, 0.11 mmol) in CH$_2$Cl$_2$ (1 mL) at 0° C. was added Dess-Martin periodinane (54 mg, 0.13 mmol). The mixture was stirred at ambient temperature for 2 h and then purified directly by column chromatography (silica gel, 8:1 to 4:1 hexane/EtOAc) to provide the title compound (19 mg, 48%) as an off-white solid: ESI MS m/z 375 [C$_{19}$H$_{16}$Cl$_2$N$_2$O$_2$+H]$^+$.

Example 3

2-(4-Chloro-3-methoxy-phenoxymethyl)-1-(3,5-dichloro-benzyl)-1H-imidazole

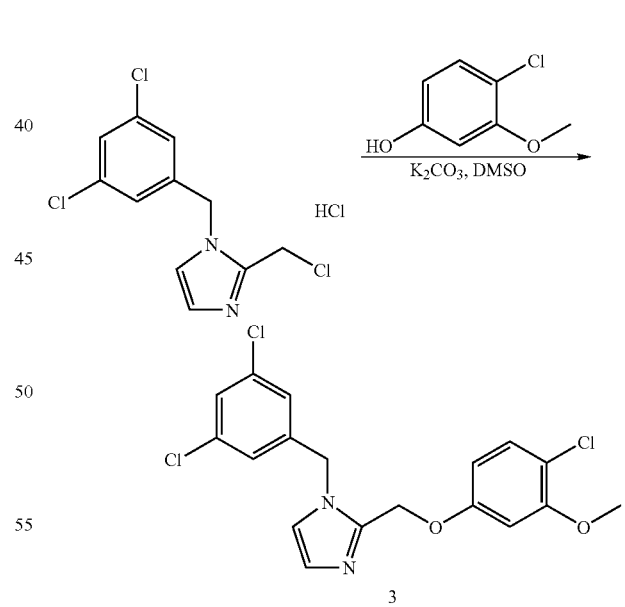

To a solution of 3-methoxyphenol (621 mg, 5.0 mmol) in dry acetonitrile (10 mL) at 0° C. was added N-chlorosuccinimide. The reaction was allowed to warm to ambient temperature then heated at reflux for 2 h. TLC analysis (4:1, hexanes/EtOAc) indicated two products (R$_f$: 0.22 and 0.30). After removal of solvent in vacuo and column chromatography (8:1 to 4:1 hexanes/EtOAc) the two products were isolated individually and characterized by $^1$H and NOESY NMR. The desired 4-chloro-3-methoxyphenol was identified as the lower $R_f$ product and isolated as a colorless oil (360 mg, 46%).

To a mixture of 2-chloromethyl-1-(3,5-dichlorobenzyl)-1H-imidazole hydrochloride (see Example 1) (150 mg, 0.5 mmol), 4-chloro-3-methoxyphenol (158 mg, 1 mmol) and DMSO (1 mL) was added $K_2CO_3$ (415 mg, 3 mmol). The reaction was stirred at ambient temperature for 8 h before diluting with water (10 mL). A solution of 1N HCl was added until the mixture was only slightly basic (pH 8) before extracting with EtOAc (30 mL). The EtOAc phase was washed with water (10 mL), dried ($Na_2SO_4$) and concentrated in vacuo. The residue was purified by column chromatography (silica gel, 1:2, hexanes/EtOAc) to afford the title compound (194 mg, 97%) as a white solid: ESI MS m/z 397 $[C_{18}H_{15}Cl_3N_2O_2+H]^+$.

Example 4

Benzyl-{1-[1-(3,5-dichloro-benzyl)-1H-imidazol-2-yl]-ethyl}-amine

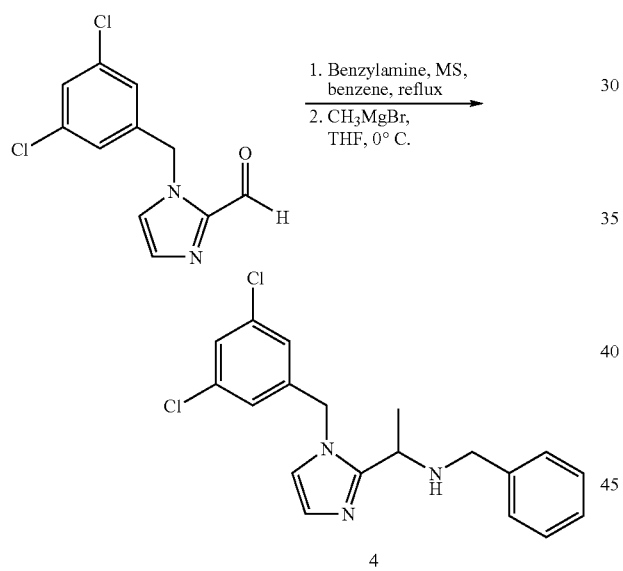

A mixture of 1-(3,5-dichloro-benzyl)-1H-imidazole-2-carbaldehyde (see Example 2) (128 mg, 0.50 mmol), benzylamine (64 mg, 0.60 mmol), 3A molecular sieves (100 mg) and benzene (5 mL) was refluxed under $N_2$ for 3 h. After cooling, the mixture was filtered and the filtrate concentrated in vacuo. The crude imine was dissolved in dry THF (3 mL) and the solution cooled to 0° C. before addition of MeMgBr (0.2 mL of a 3N solution in THF, 0.6 mmol). The resulting mixture was stirred at 0° C. for 1 h and then quenched with saturated $NH_4Cl$ (2 mL). After diluting with water (10 mL), the mixture was extracted with $CH_2Cl_2$ (2×40 mL). The combined $CH_2Cl_2$ extracts were dried over $Na_2SO_4$ and concentrated in vacuo. The residue was purified by column chromatography (silica gel, 40:1 to 20:1 $CH_2Cl_2$/MeOH) to provide the title compound (60 mg, 33%) as a colorless oil: ESI MS m/z 360 $[C_{19}H_{19}Cl_2N_2+H]^+$.

Example 5

3-[[1-(3,5-Dichloro-benzyl)-1H-imidazol-2-ylmethyl]-(3-fluoro-benzyl)-amino]-propionamide)

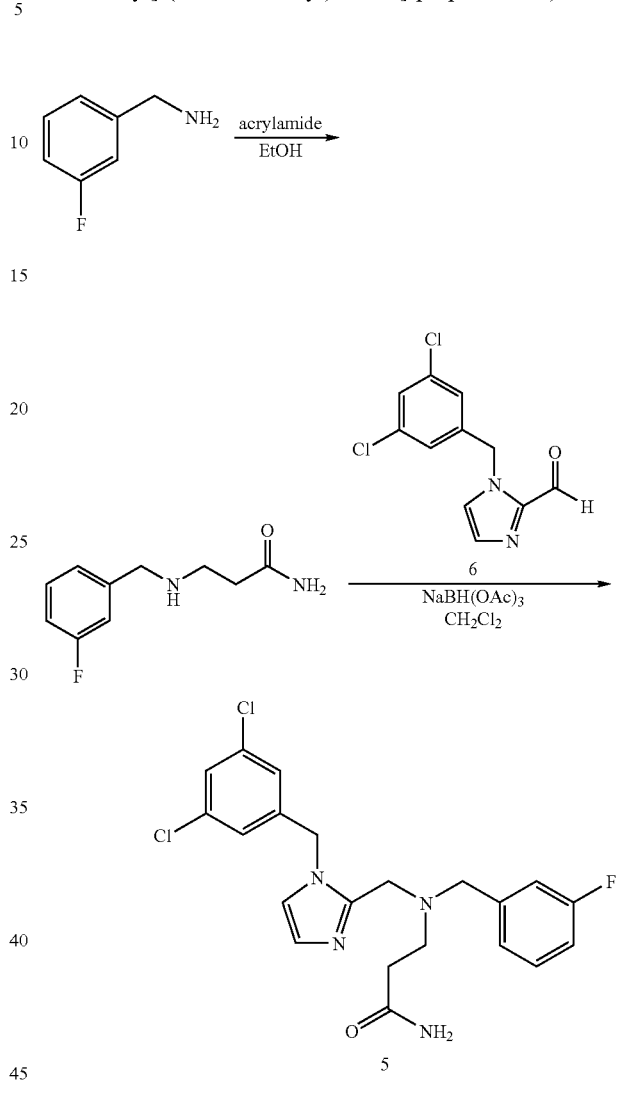

A mixture of 3-fluorobenzylamine (125 mg, 1.0 mmol), acrylamide (65 μL, 1.0 mmol) and EtOH (1 mL) was stirred at ambient temperature for 24 h. The solvent was evaporated in vacuo to afford the 3-(3-fluoro-benzylamino)-propionamide (196 mg, 100%): ESI MS m/z 197 $[C_{10}H_{13}FN_2O+H]^+$.

To a mixture of 3-(3-Fluoro-benzylamino)-propionamide (98 mg, 0.5 mmol), 1-(3,5-dichloro-benzyl)-1H-imidazole-2-carbaldehyde, (see Example 2) (102 mg, 0.4 mmol) and $CH_2Cl_2$ (2 mL) was added $NaBH(OAc)_3$ (119 mg, 0.56 mmol). The mixture was stirred at ambient temperature for 3 h before addition of saturated $NaHCO_3$ (8 mL). The mixture was extracted with $CH_2Cl_2$ (2×15 mL) and the combined $CH_2Cl_2$ extracts dried over $Na_2SO_4$. Volatiles were removed in vacuo and the residue purified by column chromatography (silica gel, 20:1 $CH_2Cl_2$/MeOH) to provide the title compound (71 mg, 40%) as colorless, viscous oil: ESI MS m/z 435 $[C_{21}H_{21}Cl_2FN_4O+H]^+$.

Example 6

[1-(3,5-Dichloro-benzyl)-1H-imidazol-2-ylmethyl]-(3-fluoro-benzyl)-isopropyl-amine (6a)

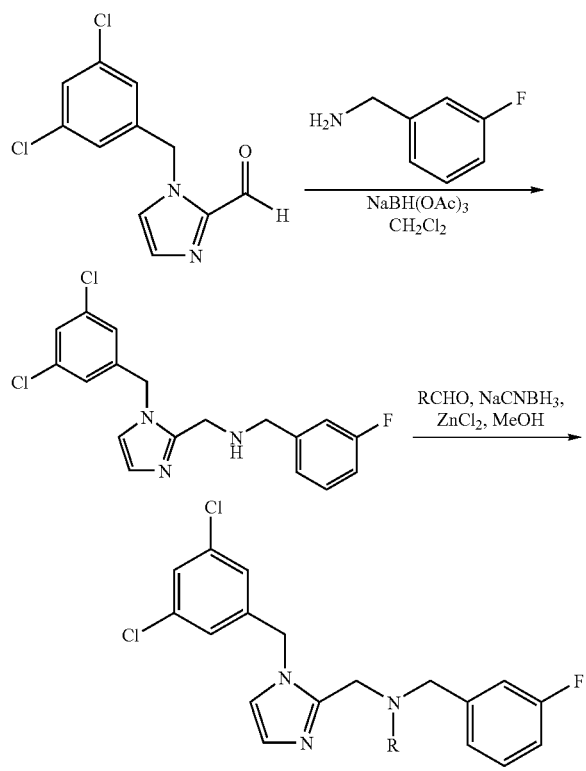

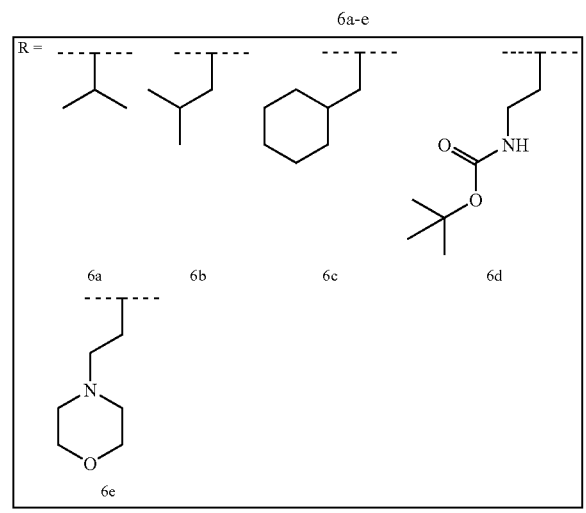

To a mixture of 1-(3,5-dichloro-benzyl)-1H-imidazole-2-carbaldehyde (see Example 2) (1.00 g, 3.90 mmol) and 2-fluorobenzylamine (0.67 mL, 5.88 mmol) in $CH_2Cl_2$ (10 mL) was added $NaBH(OAc)_3$ (1.16 g, 5.50 mmol) portionwise. The reaction was stirred at ambient temperature under $N_2$ for 18 h before quenching with 1N NaOH (30 mL) and extracting with $CH_2Cl_2$ (2×50 mL). The combined organic extracts were dried over $Na_2SO_4$ and concentrated in vacuo to give 1.83 g of crude product. The crude material was determined to contain the imine intermediate and was therefore dissolved in MeOH and treated with $NaBH_4$ (1.0 g). The reaction was worked up in an identical manner as above to give the desired [1-(3,5-dichloro-benzyl)-1H-imidazol-2-ylmethyl]-(3-fluoro-benzyl)-amine (1.43 g, 95%): ESI MS m/z 364 $[C_{18}H_{16}Cl_2FN_3+H]^+$.

A mixture of [1-(3,5-dichloro-benzyl)-1H-imidazol-2-ylmethyl]-(3-fluoro-benzyl)-amine, (200 mg, 0.55 mmol), acetone (81 uL, 1.10 mmol) and 3A molecular sieves (300 mg) in MeOH (3 mL) was stirred at ambient temperature under $N_2$. After 5 h, $NaBH_3CN$ was added and the mixture stirred for an additional 2 h. Water (2 mL) was added and the reaction mixture concentrated in vacuo. The residue was taken up in 1N NaOH (20 mL) and extracted with $CH_2Cl_2$ (3×30 mL). The combined extracts were dried over $Na_2SO_4$ and concentrated in vacuo. The crude material was purified by chromatography (silica gel, 100% EtOAc) and the isolated product converted to the di-hydrochloride salt by treatment with excess anhydrous HCl in methanol solution. The volatiles were removed in vacuo to afford the desired product 6a (58 mg, 26%) as an off-white solid: ESI MS m/z 406 $[C_{21}H_{22}Cl_2FN_3+H]^+$.

The following compounds were prepared by the same procedure described above for 6a, using the appropriate aldehyde in place of acetone:

[1-(3,5-Dichloro-benzyl)-1H-imidazol-2-ylmethyl]-(3-fluoro-benzyl)-isobutyl-amine (6b)

Prepared according to above procedure to afford (48 mg, 25%) as an off-white solid: ESI MS m/z 420 $[C_{22}H_{24}Cl_2FN_3+H]^+$.

Cyclohexylmethyl-[1-(3,5-dichloro-benzyl)-1H-imidazol-2-ylmethyl]-(3-fluoro-benzyl)-amine (6c)

Prepared according to above procedure to afford (103 mg, 35%) as an off-white solid: ESI MS m/z 460 $[C_{25}H_{28}Cl_2FN_3+H]^+$.

{2-[[1-(3,5-Dichloro-benzyl)-1H-imidazol-2-ylmethyl]-(3-fluoro-benzyl)-amino]-ethyl}-carbamic acid tert-butyl ester (6d)

Prepared according to above procedure to afford (445 mg, 66%) as an off-white solid: ESI MS m/z 507 $[C_{25}H_{29}Cl_2FN_4O_2+H]^+$.

[1-(3,5-Dichloro-benzyl)-1H-imidazol-2-ylmethyl]-(3-fluoro-benzyl)-(2-morpholin-4-yl-ethyl)-amine (6e)

Prepared according to above procedure to afford (12 mg, 5%) as an off-white solid: ESI MS m/z 477 $[C_{24}H_{27}Cl_2FN_4O+H]^+$.

Example 7
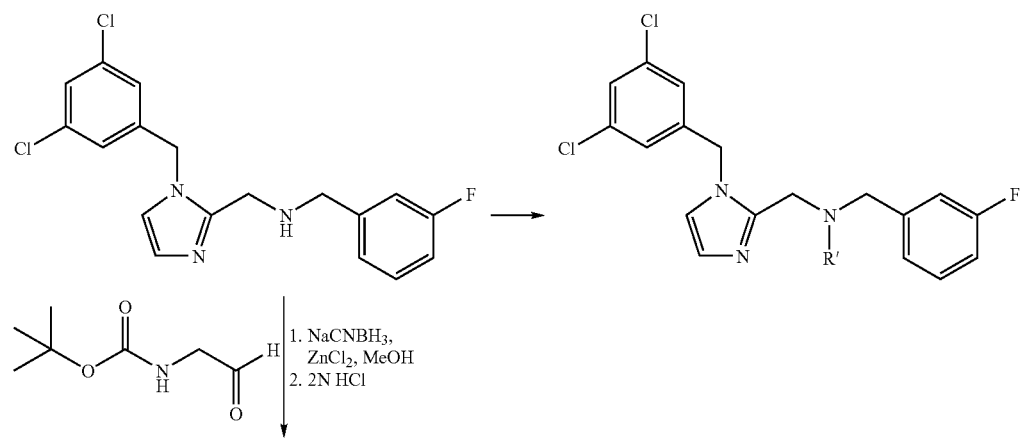
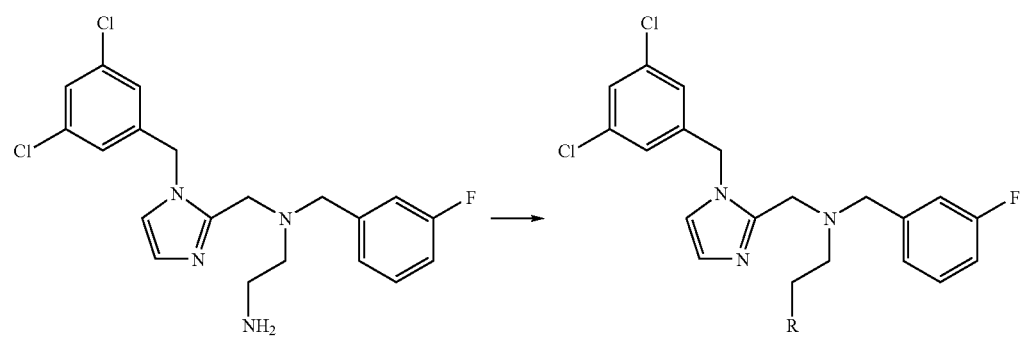
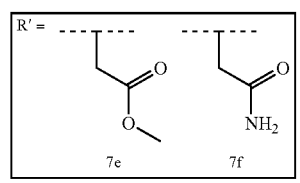
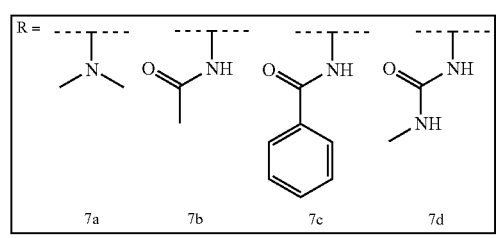

{2-[[1-(3,5-dichloro-benzyl)-1H-imidazol-2-ylmethyl]-(3-fluoro-benzyl)-amino]-ethyl}-carbamic acid tert-butyl ester, (see Example 6) (455 mg, 0.899 mmol) was dissolved in MeOH (7 mL) and treated with 4N HCl/ether (2 mL). The solution was stirred at ambient temperature for 4 h. then heated to 40° C. for 3 h. The solvent was evaporated in vacuo providing $N^1$-[1-(3,5-dichloro-benzyl)-1H-imidazol-2-ylmethyl]-$N^1$-(3-fluoro-benzyl)-ethane-1,2-diamine (341 mg, 93%). ESI MS m/z 407 $[C_{20}H_{21}Cl_2FN_4+H]^+$.

N-[1-(3,5-Dichloro-benzyl)-1H-imidazol-2-ylmethyl]-N'-(3-fluoro-benzyl)-N',N'-dimethyl-ethane-1, 2-diamine (7a)

A mixture of $N^1$-[1-(3,5-dichloro-benzyl)-1H-imidazol-2-ylmethyl]-$N^1$-(3-fluoro-benzyl)-ethane-1,2-diamine (54 mg, 0913 mmol), 37% aqueous formaldehyde solution (50 uL, 0.60 mmol) and $NaBH(OAc)_3$ (141 mg, 0.66 mmol) in $CH_2Cl_2$ (4 mL) was stirred at ambient temperature under $N_2$ for 24 h. The reaction was quenched with 1N NaOH (20 mL) and extracted with $CH_2Cl_2$ (3×30 mL). The combined extracts were dried over $Na_2SO_4$, concentrated in vacuo and the resulting residue purified by semi-preparative HPLC. The purified material was partitioned with 2N NaOH and $CH_2Cl_2$. The organic layer was concentrated in vacuo and the residue was treated with an excess of 2N HCl in $Et_2O$ solution to afford the di-hydrochloride salt of the desired product 7a (16 mg, 22%) after concentration in vacuo: ESI MS m/z 435 $[C_{22}H_{25}Cl_2FN_4+H]^+$.

N-{2-[[1-(3,5-Dichloro-benzyl)-1H-imidazol-2-ylmethyl]-(3-fluoro-benzyl)-amino]-ethyl}-acetamide (7b)

A mixture of $N^1$-[1-(3,5-dichloro-benzyl)-1H-imidazol-2-ylmethyl]-N-4-(3-fluoro-benzyl)-ethane-1,2-diamine (100 mg, 0.25 mmol), $Ac_2O$ (27.6 mg, 0.27 mmol) and diisopropylethylamine (64 uL, 0.37 mmol) in $CH_2Cl_2$ (3 mL) was stirred at ambient temperature for 1 h. The reaction was quenched with water (10 mL), extracted with $CH_2Cl_2$ (3×20 mL) and the combined extracts dried over $Na_2SO_4$. The solvent was removed in vacuo and the crude material purified by chromatography (silica gel, 5% MeOH in $CH_2Cl_2$). The purified material was converted directly to the hydrochloride salt by addition of excess 2N HCl in ether and concentrated in vacuo to provide the desired product 7b (57 mg, 44%) as an off-white solid: ESI MS m/z 449 $[C_{22}H_{23}Cl_2FN_4O+H]^+$.

N-{2-[[1-(3,5-Dichloro-benzyl)-1H-imidazol-2-ylmethyl]-(3-fluoro-benzyl)-amino]-ethyl}-benzamide (7c)

Prepared according to the procedure for 7b procedure to afford the desired product 7c (89 mg, 71%) off-white solid. ESI MS m/z 511 $[C_{27}H_{25}Cl_2FN_4O+H]^+$.

1-{2-[[1-(3,5-Dichloro-benzyl)-1H-imidazol-2-ylmethyl]-(3-fluoro-benzyl)-amino]-ethyl}-3-methyl-urea (7d)

To a solution of $N^1$-[1-(3,5-dichloro-benzyl)-1H-imidazol-2-ylmethyl]-NM-(3-fluoro-benzyl)-ethane-1,2-diamine (60 mg, 0.15 mmol) in $CH_2Cl_2$ (3 mL) was added methylisocyanate (0.3 mL). The mixture was stirred at ambient temperature for 2 h. The solution was then concentrated in vacuo and the resulting residue purified by semi-preparative HPLC. The purified material was partitioned with 2N NaOH and $CH_2Cl_2$ and the organic layer concentrated in vacuo. The residue was treated with an excess of 2N HCl in $Et_2O$ solution to afford the hydrochloride salt of the desired product 7d (14 mg, 18%): ESI MS m/z 464 $[C_{22}H_{24}Cl_2FN_5O+H]^+$.

[[1-(3,5-Dichloro-benzyl)-1H-imidazol-2-ylmethyl]-(3-fluoro-benzyl)-amino]-acetic acid methyl ester (7e)

To a solution of [1-(3,5-dichloro-benzyl)-1H-imidazol-2-ylmethyl]-(3-fluoro-benzyl)-amine (200 mg, 0.55 mmol) and triethylamine (0.18 mL, 1.37 mmol) in THF (2 mL) was added methylbromoacetate (78 uL, 0.82 mmol). The reaction was stirred at ambient temperature for 18 h before diluting with EtOAc (50 mL). The solution was washed with water (20 mL) and brine then dried over $Na_2SO_4$. The solvent was removed in vacuo and the residue purified by column chromatography (silica gel, 5% MeOH in $CH_2Cl_2$). The purified product was treated with excess 2N HCl in $Et_2O$ solution to afford the hydrochloride salt of the desired product 7e (74 mg, 26%): ESI MS m/z 436 $[C_{21}H_{20}Cl_2FN_3O+H]^+$.

2-[[1-(3,5-Dichloro-benzyl)-1H-imidazol-2-ylmethyl]-(3-fluoro-benzyl)-amino]-acetamide (7f)

[[1-(3,5-Dichloro-benzyl)-1H-imidazol-2-ylmethyl]-(3-fluoro-benzyl)-amino]-acetic acid methyl ester (7e) (81 mg, 0.19 mmol) was dissolved in a 7N solution of $NH_3$ in MeOH (10 mL). The solution was heated at 100° C. with stirring in a sealed tube reaction vessel for 18 h. The volatiles were removed in vacuo and the residue purified by column chromatography (silica gel, 5% MeOH in $CH_2Cl_2$) to provide the desired product 7f (40 mg, 51%): ESI MS m/z 421 $[C_{20}H_{19}Cl_2FN_4O+H]^+$.

Example 8

1-{3-[[1-(3,5-Dichloro-benzyl)-1H-imidazol-2-ylmethyl]-(3-fluoro-benzyl)-amino]-propionyl}-piperidine-4-carboxylic acid amide

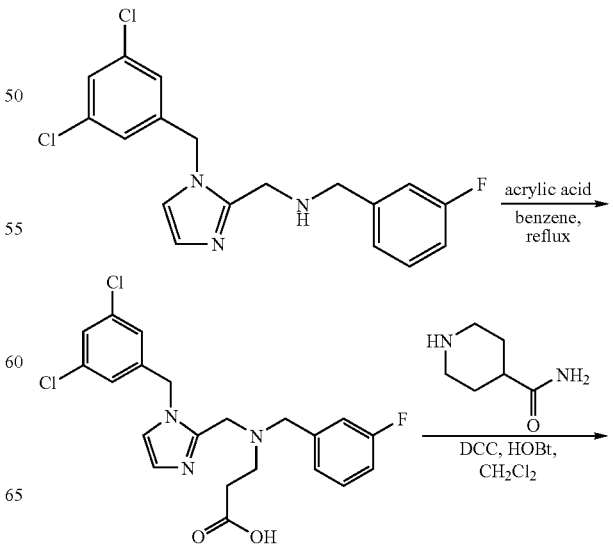

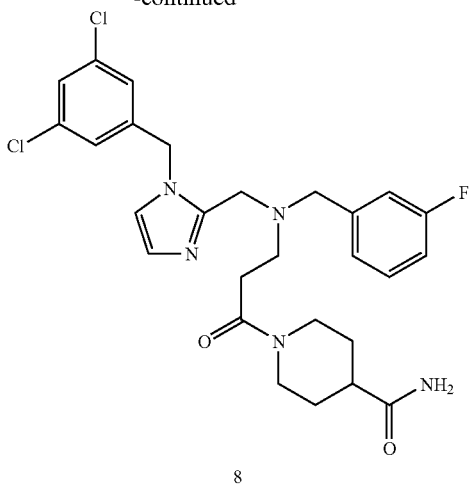

8

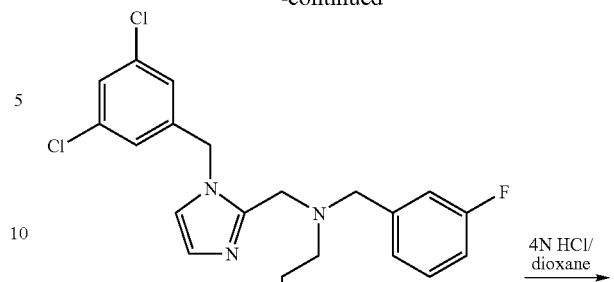

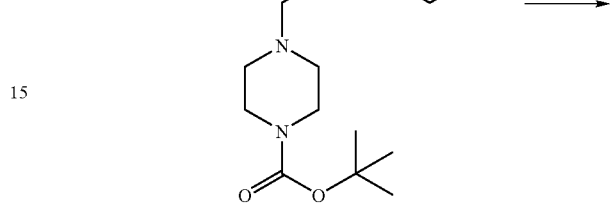

9

A mixture of [1-(3,5-dichloro-benzyl)-1H-imidazol-2-yl-methyl]-(3-fluoro-benzyl)-amine (see Example 6), (113 mg, 0.31 mmol), acrylic acid (23 mg, 0.33 mmol) and benzene (4 mL) was heated to reflux for 14 h. The solvent was evaporated in vacuo to afford crude 3-[[1-(3,5-dichloro-benzyl)-1H-imidazol-2-ylmethyl]-(3-fluoro-benzyl)-amino]-propionic acid. To a mixture of this acid (135 mg, 0.31 mmol), isonipecotamide (44 mg, 0.35 mmol), 1-hydroxybenzotriazole (45 mg, 0.33 mmol) and $CH_2Cl_2$ (1 mL) at 0° C. was added a solution of dicyclohexylcarbodiimide (68 mg, 0.33 mmol) in $CH_2Cl_2$ (0.5 mL). The mixture was stirred at ambient temperature for 14 h and then concentrated in vacuo. The residue was purified by column chromatography (silica gel, 20:1 to 10:1 $CH_2Cl_2$/MeOH) to provide the title compound (86 mg, 51%) as a white solid: ESI MS m/z 546 $[C_{27}H_{30}Cl_2FN_5O_2+H]^+$.

Example 9

1-(4-{2-[[1-(3,5-Dichloro-benzyl)-1H-imidazol-2-ylmethyl]-(3-fluoro-benzyl)-amino]-ethyl}-piperazin-1-yl)-ethanone

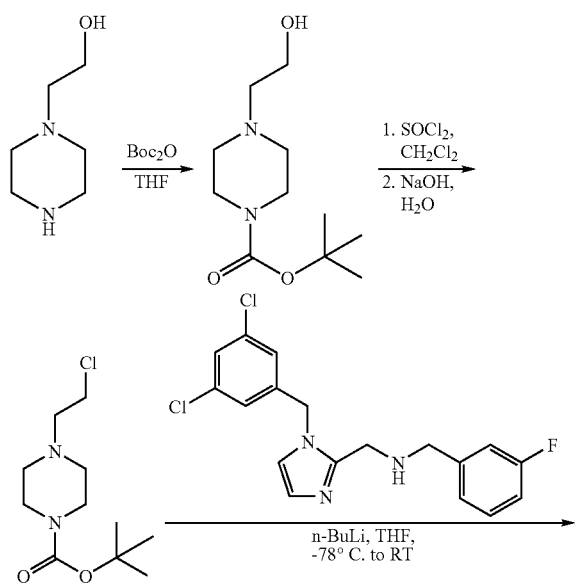

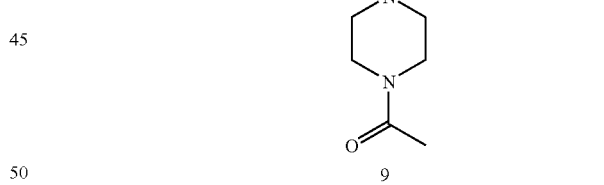

$(Boc)_2O$ (2.29 g, 10.5 mmol) was added to a solution 1-(2-hydroxyethyl)piperizine (1.30 g, 10 mmol) in THF (10 mL) at 0° C. The mixture was stirred at ambient temperature for 14 h. The volatiles were removed in vacuo to afford 4-(2-hydroxy-ethyl)-piperazine-1-carboxylic acid tert-butyl ester (2.30 g, 100%) as a colorless oil which solidified on standing: ESI MS m/z 231 $[C_{11}H_{22}N_2O_3+H]^+$.

To a solution of 4-(2-hydroxy-ethyl)-piperazine-1-carboxylic acid tert-butyl ester (231 mg, 1.0 mmol) in $CH_2Cl_2$ (2 mL) at 0° C. was added dropwise $SOCl_2$ (0.15 mL, 2.0 mmol). The mixture was allowed to warm up to ambient temperature and stirred for 14 h. Volatiles were removed in vacuo and the residue partitioned between $CH_2Cl_2$ (20 mL) and saturated $NaHCO_3$ (10 mL). The $CH_2Cl_2$ phase was dried over $Na_2SO_4$ and concentrated in vacuo to afford 4-(2-chloro-ethyl)-piperazine-1-carboxylic acid tert-butyl ester as a white solid (130 mg, 52%): ESI MS m/z 249 [$C_{11}H_{21}ClN_2O_2$+H]$^+$.

To a solution of [1-(3,5-dichloro-benzyl)-1H-imidazol-2-ylmethyl]-(3-fluoro-benzyl)-amine (146 mg, 0.4 mmol) in THF (1 mL) at −78° C. was added dropwise a solution of n-BuLi in hexane (0.19 mL, 0.44 mmol) and the mixture stirred at −78° C. for 30 min. A solution of 4-(2-Chloro-ethyl)-piperazine-1-carboxylic acid tert-butyl ester (116 mg, 0.46 mmol) in THF (1 mL) was then added dropwise and the mixture allowed to warm to ambient temperature before stirring for an additional 24 h. The reaction was quenched with water (10 mL) and extracted with $CH_2Cl_2$ (2×40 mL). The combined $CH_2Cl_2$ extracts were dried over $Na_2SO_4$ and concentrated in vacuo. The residue was purified by column chromatography (silica gel, 20:1 $CH_2Cl_2$/MeOH) to provide 4-{2-[[1-(3,5-dichloro-benzyl)-1H-imidazol-2-ylmethyl]-(3-fluoro-benzyl)-amino]-ethyl}-piperazine-1-carboxylic acid tert-butyl ester (102 mg, 44%) as a colorless viscous oil: ESI MS m/z 576 [$C_{29}H_{36}Cl_2FN_5O_2$+H]$^+$.

A mixture of 4-{2-[[1-(3,5-dichloro-benzyl)-1H-imidazol-2-ylmethyl]-(3-fluoro-benzyl)-amino]-ethyl}-piperazine-1-carboxylic acid tert-butyl ester (92 mg, 0.16 mmol) and 4N HCl/dioxane (5 mL) was stirred at ambient temperature for 2 h. The solvent was removed in vacuo and water (5 mL) added. The pH of the solution was adjusted to pH 9 by addition of 1N NaOH and the mixture extracted with $CH_2Cl_2$ (2×20 mL). The combined $CH_2Cl_2$ extracts were dried over $Na_2SO_4$ and concentrated in vacuo to afford [1-(3,5-dichloro-benzyl)-1H-imidazol-2-ylmethyl]-(3-fluoro-benzyl)-(2-piperazin-1-yl-ethyl)-amine (74 mg, 98%) as colorless a viscous oil: ESI MS m/z 476 [$C_{24}H_{28}Cl_2FN_5$+H]$^+$.

To a solution of [1-(3,5-dichloro-benzyl)-1H-imidazol-2-ylmethyl]-(3-fluoro-benzyl)-(2-piperazin-1-yl-ethyl)-amine (55 mg, 0.12 mmol) in $CH_2Cl_2$ at ambient temperature was added dropwise $Ac_2O$ (34 µL, 0.36 mmol). The mixture was stirred for 2 h before addition of saturated $NaHCO_3$ (6 mL). The mixture was extracted with $CH_2Cl_2$ (2×20 mL) and the combined extracts dried over $Na_2SO_4$ then concentrated in vacuo. The residue was purified by semi-preparative HPLC to provide the title compound (42 mg, 66%) as a viscous oil: ESI MS m/z 518 [$C_{26}H_{30}Cl_2FN_5O$+H]$^+$.

Example 10

2-Benzyl-3-[1-(3,5-dichloro-benzyl)-1H-imidazol-2-yl]-propionamide

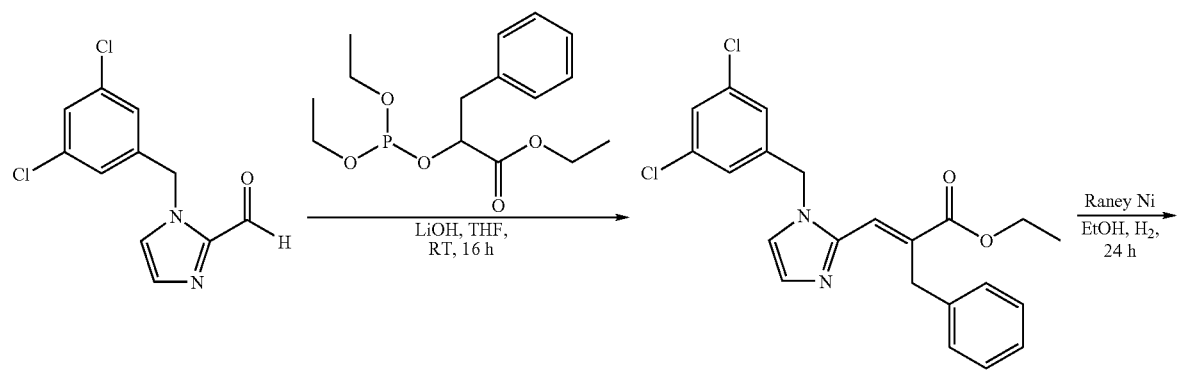

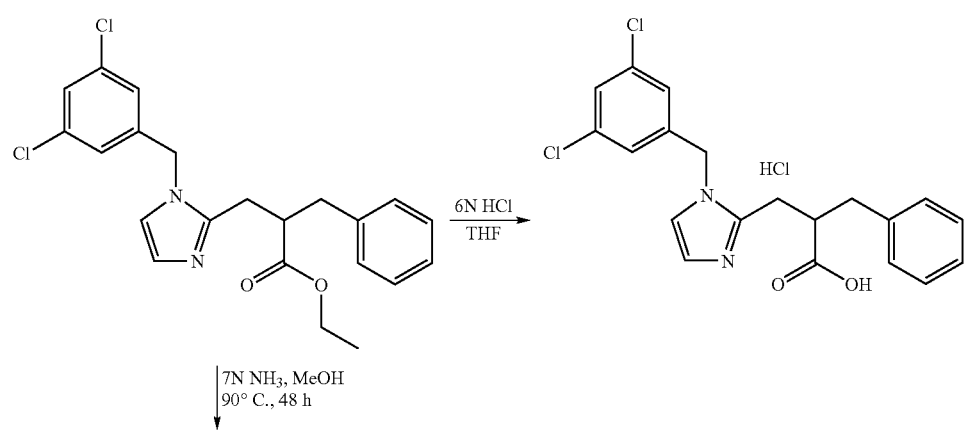

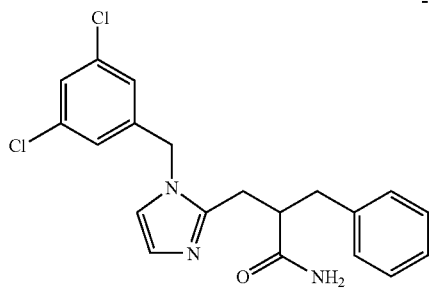

10

To a solution of 1-(3,5-dichloro-benzyl)-1H-imidazole-2-carbaldehyde (see Example 2) (0.59 g, 2.33 mmol) and triethyl-2-benzylphosponoacetate (0.81 g, 2.58 mmol) (prepared according to *J. Med. Chem.* 1993, 36, 87-94) in dry THF (3 mL) was added LiOH (62 mg, 2.58 mmol). The mixture was stirred for 14 h at ambient temperature then partitioned with water (20 mL) and EtOAc (40 mL). The organic layer was collected, washed with brine, dried over MgSO$_4$ and concentrated in vacuo. The material was purified by column chromatography (silica gel, 100% diethyl ether) to provide 2-benzyl-3-[1-(3,5-dichloro-benzyl)-1H-imidazol-2-yl]-acrylic acid ethyl ester (0.41 g, 42%) as a colorless oil: ESI MS m/z 415 [$C_{22}H_{20}Cl_2N_2O_2$+H]$^+$.

To a solution of 2-benzyl-3-[1-(3,5-dichloro-benzyl)-1H-imidazol-2-yl]-acrylic acid ethyl ester, (409 mg, 0.99 mmol) in absolute ethanol (30 mL) was added Raney nickel active catalyst (approximately 1 g of a 50% suspension in water). The reaction flask was flushed with N$_2$ prior to flushing with H$_2$ via a balloon. The reaction was stirred at ambient temperature for 14 h under a balloon atmosphere of H$_2$. After flushing with N$_2$, the reaction was filtered through a plug of celite and the filtrate concentrated in vacuo. The resulting residue was partitioned with CH$_2$Cl$_2$ (10 mL) and saturated NaHCO$_3$ (5 mL). The organic layer was washed with brine, dried over MgSO$_4$ and concentrated in vacuo to afford 2-benzyl-3-[1-(3,5-dichloro-benzyl)-1H-imidazol-2-yl]-propionic acid ethyl ester (385 mg, 94%) as a colorless oil: ESI MS m/z 417 [$C_{22}H_{22}Cl_2N_2O_2$+H]$^+$.

To a solution of 2-benzyl-3-[1-(3,5-dichloro-benzyl)-1H-imidazol-2-yl]-propionic acid ethyl ester (50 mg, 0.12 mmol) in THF (3 mL) was added 6 N HCl (3 mL). The mixture was heated at 75° C. for 14 h with vigorous stirring. The reaction was concentrated in vacuo and the residue washed with Et$_2$O then dried in vacuo to provide the hydrochloride salt of 2-benzyl-3-[1-(3,5-dichloro-benzyl)-1H-imidazol-2-yl]-propionic acid (26 mg, 84%) as a white solid: ESI MS m/z 389 [$C_{20}H_{18}Cl_2N_2O_2$+H]$^+$.

2-Benzyl-3-[1-(3,5-dichloro-benzyl)-1H-imidazol-2-yl]-propionic acid ethyl ester (82 mg, 0.20 mmol) was dissolved in a solution of 7 N ammonia in methanol (10 mL). The solution was heated in a sealed tube reaction vessel at 100° C. for 48 h. The solvent was evaporated in vacuo and the residue purified using semi-preparative HPLC to provide the trifluoroacetic acid salt of the title compound (15 mg, 20%) as a colorless oil: ESI MS m/z 388 [$C_{20}H_{19}Cl_2N_3O$+H]$^+$.

Example 11

2-(3-Chloro-5-methoxy-phenoxymethyl)-1-(3,5-dichloro-benzyl)-1H-imidazole

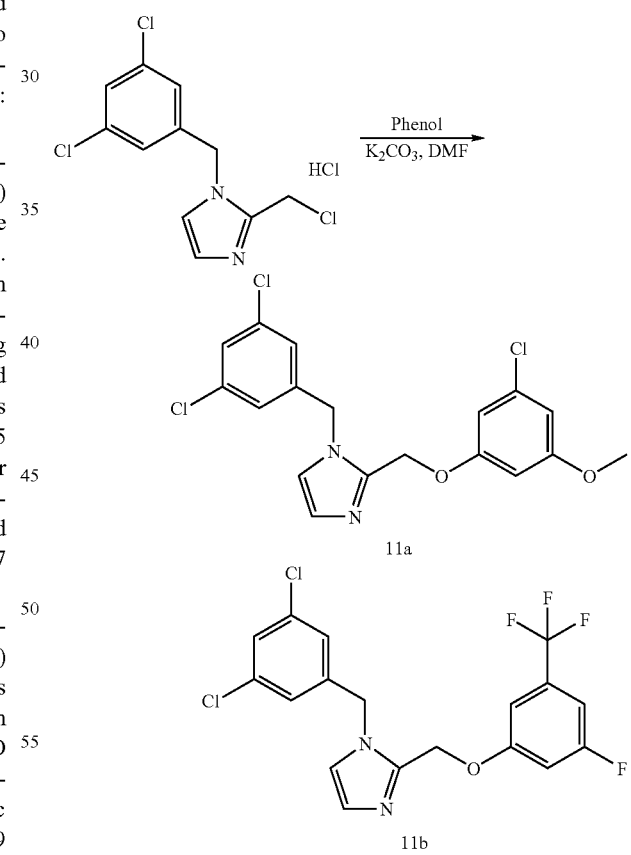

3,-Chloro-5-methoxy-1-phenol was dissolved in anhydrous DMF and K$_2$CO$_3$ was added. The reaction mixture was stirred at room temperature for 15 min and chloromethyl-1-(3,5-dichlorobenzyl)-1H-imidazole hydrochloride (see Example 1) was added to the reaction mixture. The resulting mixture was stirred at room temperature for 36 h. The mixture was diluted with EtOAc and washed with water (×2). The organic phase was dried over Na$_2$SO$_4$ and concentrated. The resulting residue was then purified by silica gel prep TLC using CH$_2$Cl$_2$:MeOH 98:2 as an eluent to afford the title compound (56 mg, 49%); MS m/z 397 [C$_{18}$H$_{15}$Cl$_3$N$_2$O$_2$+H]$^+$.

The following compound was prepared by the above procedure using the appropriate phenol:

1-(3,5-Dichloro-benzyl)-2-(3-fluoro-5-trifluoromethyl-phenoxymethyl)-1H-imidazole; MS m/z 419 [C$_{18}$H$_{12}$Cl$_2$F$_4$N$_2$O+H]$^+$.

Example 12

Benzyl-[1-(3,5-dichloro-benzyl)-1H-imidazol-2-yl]-amine

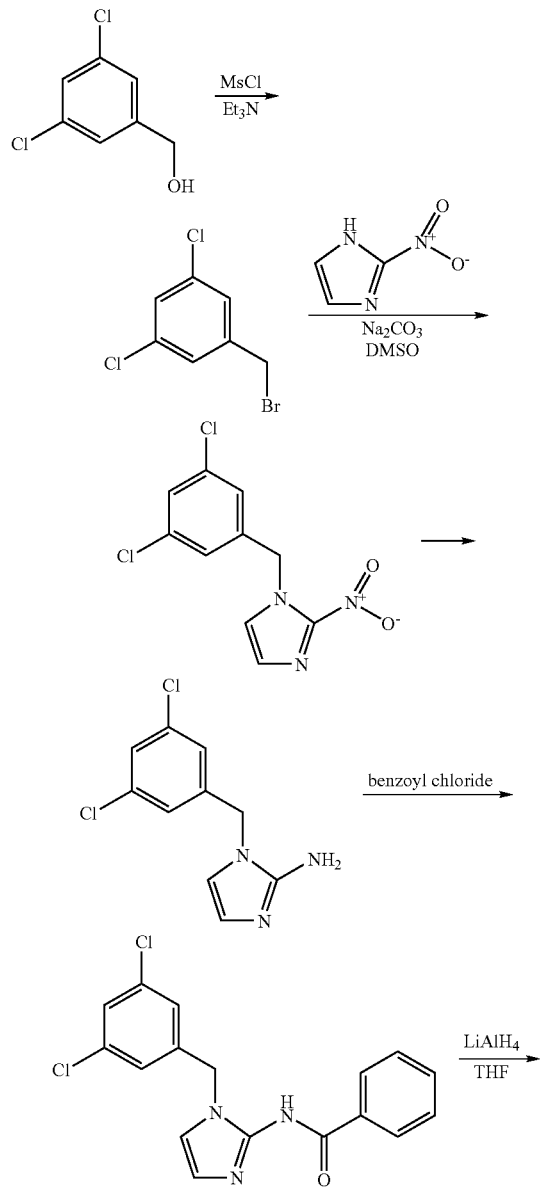

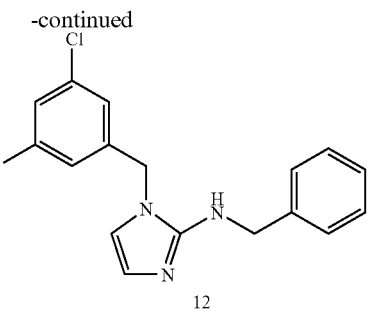

To a solution of 3,5-dichlorobenzylalcohol in anhydrous THF at −30° C. was added Et$_3$N. Mesyl chloride in THF was added to the solution dropwise. The reaction mixture was stirred at that temperature for 1 h until all the starting material was consumed. Then, LiBr was added to the reaction mixture and stirred for another 2 h. When the reaction was over, the reaction mixture was diluted with EtOAc and washed with water (×3). The organic phase was dried over Na$_2$SO$_4$ and concentrated to afford 1-bromomethyl-3,5-dichloro-benzene as a light brown solid (9.3 g, 86%).

To a solution of 2-nitroimidazole and 1-bromomethyl-3,5-dichloro-benzene in anhydrous DMSO was added Na$_2$CO$_3$. The reaction mixture was heated to 60° C. for 6 h. The reaction mixture was then diluted with EtOAc and washed with water (×4). The organic phase was dried over Na$_2$SO$_4$ and concentrated. The resulting residue was purified by silica gel prep TLC using 98:2 CH$_2$Cl$_2$:MeOH to afford 1-(3,5-dichloro-benzyl)-2-nitro-1H-imidazole (0.66 g, 91%).

1-(3,5-dichloro-benzyl)-2-nitro-1H-imidazole was dissolved in a mixture of ethanol and acetic acid, and Fe was added. The mixture was heated to 80° C. for 20 min. During this period of time, the mixture turned into reddish brown in color and then grayish white precipitate was formed. The reaction mixture was cooled to room temperature and diluted with EtOAc. The slurry was filtered through a pad of diatomaceous earth and washed with EtOAc. The filtrate was basified using 2N NaOH solution until pH ~8. The organic phase was then separated and the aqueous layer was extracted with EtOAc. The combined EtOAc layer was dried over Na$_2$SO$_4$ and concentrated to afford 1-(3,5-dichloro-benzyl)-1H-imidazol-2-ylamine as a white solid (80 mg, 90%).

1-(3,5-dichloro-benzyl)-1H-imidazol-2-ylamine was dissolved in CH$_2$Cl$_2$ and Et$_3$N was added followed by benzoyl chloride. The reaction mixture was stirred at room temperature for 2 h and washed with 1N HCl, saturated NaHCO$_3$ and water. The organic phase was dried over Na$_2$SO$_4$ and concentrated. The residue was purified by silica gel prep TLC using 95:5 CH$_2$Cl$_2$:MeOH to afford N-[1-(3,5-dichloro-benzyl)-1H-imidazol-2-yl]-benzamide (40 mg, 56%).

N-[1-(3,5-Dichloro-benzyl)-1H-imidazol-2-yl]-benzamide, was dissolved in anhydrous THF and 1M LiAlH$_4$ was added to the reaction solution at room temperature. The reaction mixture was then heated to 70° C. and stirred for 10 min. The mixture was then diluted with CH$_2$Cl$_2$ and water was slowly added until H$_2$ formation stopped. The reaction mixture was passed through a cartridge packed with anhydrous Na$_2$SO$_4$. The filtrated was concentrated and purified by silica

[1-(3,5-Dichloro-benzyl)-1H-imidazol-2-yl]-phenethyl-amine gel preparative TLC using 95:5 CH$_2$Cl$_2$:MeOH to afford the title compound (5 mg, 7%); MS m/z 332 [C$_{17}$H$_{15}$Cl$_2$N$_3$+H]$^+$.

N-[1-(3,5-Dichloro-benzyl)-1H-imidazol-2-yl]-2-phenyl-acetamide was prepared as described for N-[1-(3,5-dichloro-benzyl)-1H-imidazol-2-yl]-benzamide, using the appropriate acid chloride to afford N-[1-(3,5-Dichloro-benzyl)-1H-imidazol-2-yl]-2-phenyl-acetamide (70 mg, 47%).

[1-(3,5-Dichloro-benzyl)-1H-imidazol-2-yl]-phenethyl-amine was then prepared using the above acetamide and the procedure described for 12 (9 mg, 19%); MS m/z 346 [C$_{18}$H$_{17}$Cl$_2$N$_3$+H]$^+$.

Example 13

[1-(3,5-Dichloro-benzyl)-1H-imidazol-2-yl]-(3-methoxy-benzyl)-amine

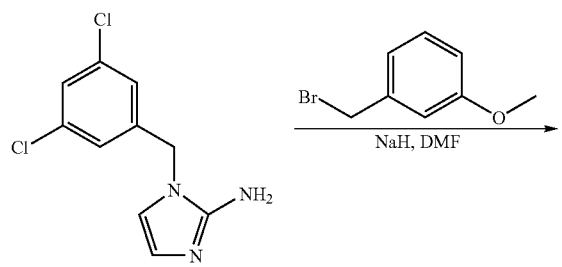

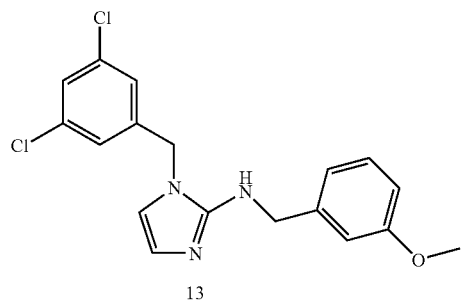

13

1-(3,5-Dichloro-benzyl)-1H-imidazol-2-ylamine (see Example 12) was dissolved in anhydrous DMF and NaH was added to the solution under H$_2$. The reaction mixture was stirred at room temperature for 10 min and 3-methoxybenzylbromide was added. The reaction mixture was stirred at 65° C. for 5 h. The reaction mixture was then diluted with EtOAc and washed with water (×5). The organic phase was dried over Na$_2$SO$_4$ and concentrated. The resulting residue was purified by silica gel preparative TLC using CH$_2$Cl$_2$:MeOH 95:5 to afford the title compound (7 mg, 5%); LCMS m/z 362 [C$_{18}$H$_{17}$Cl$_2$N$_3$O+H]$^+$.

Example 14

[1-(3,5-Dichloro-benzyl)-1H-imidazol-2-yl]-(4-fluoro-benzyl)-amine

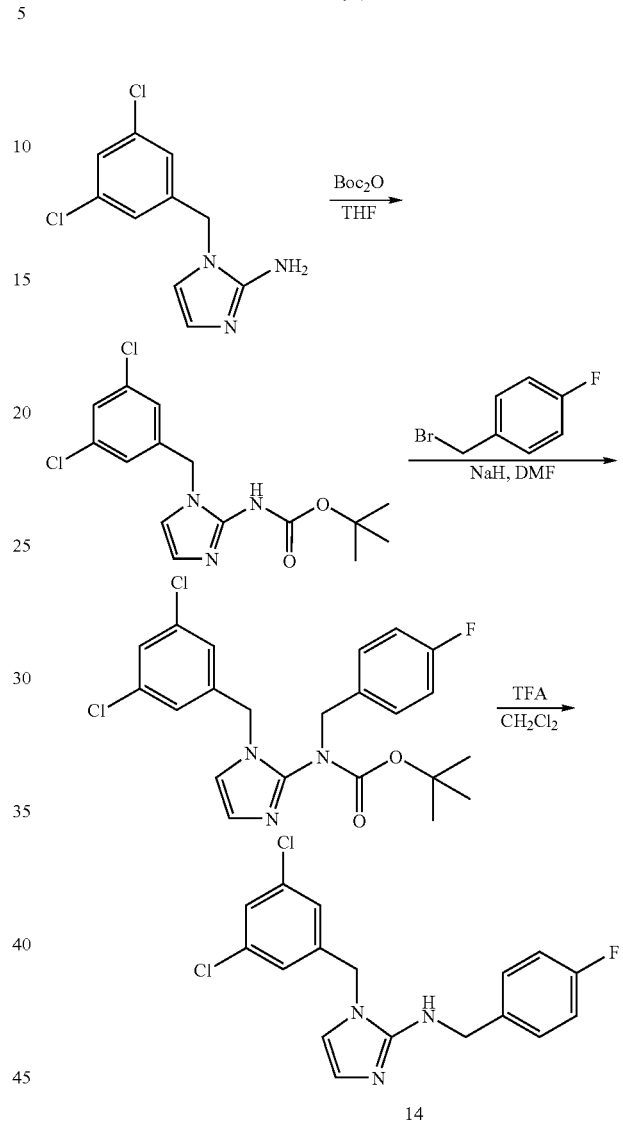

1-(3,5-Dichloro-benzyl)-1H-imidazol-2-ylamine (see Example 12) was dissolved in anhydrous THF and Boc$_2$O was added to the solution. The reaction mixture was stirred at room temperature for 3 h. The mixture was then concentrated and the resulting residue was purified by silica gel preparative TLC using CH$_2$Cl$_2$:MeOH 95:5 as an eluent to afford [1-(3,5-dichloro-benzyl)-1H-imidazol-2-yl]-carbamic acid tert-butyl ester (100 mg, 71%).

[1-(3,5-Dichloro-benzyl)-1H-imidazol-2-yl]-carbamic acid tert-butyl ester was dissolved in anhydrous DMF and NaH was added. The mixture was stirred at room temperature for 10 min and 4-fluorobenzyl bromide was added. The reaction mixture was stirred at room temperature for another 1 h. The reaction was quenched with water and extracted with EtOAc (×3). The combined organic phase was dried over Na$_2$SO$_4$ and concentrated. The resulting residue was purified by silica gel preparative TLC using CH$_2$Cl$_2$:MeOH 95:5 as an eluent to afford [1-(3,5-dichloro-benzyl)-1H-imidazol-2-yl]-(4-fluoro-benzyl)-carbamic acid tert-butyl ester (50 mg, 76%); LCMS m/z 450 $[C_{22}H_{22}Cl_2FN_3O_2+H]^+$.

To a solution of [1-(3,5-dichloro-benzyl)-1H-imidazol-2-yl]-(4-fluoro-benzyl)-carbamic acid tert-butyl ester in $CH_2Cl_2$ was added trifluoroacetic acid. The reaction solution was stirred at room temperature for 3 h. When all the starting material was consumed, the mixture was diluted with $CH_2Cl_2$ and washed with water. The organic phase was dried over $Na_2SO_4$ and concentrated. The resulting residue was purified by silica gel preparative TLC using $CH_2Cl_2$:MeOH 95:5 as an eluent to afford the title compound (24 mg, 63%); LCMS m/z 350 $[C_{17}H_{14}Cl_2FN_3+H]^+$.

Example 15

2-Benzyloxymethyl-1-(3,5-dichloro-benzyl)-1H-imidazole

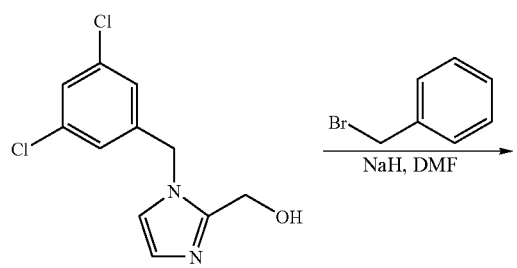

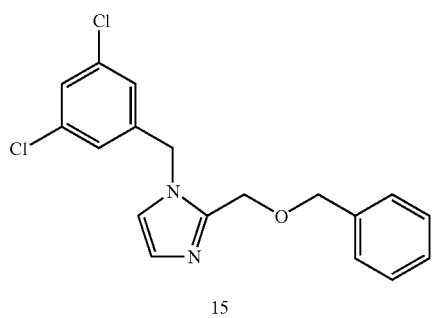

To NaH in DMF, was added [1-(3,5-dichloro-benzyl)-1H-imidazol-2-yl]-methanol (see Example 1) in DMF. The reaction mixture was stirred at 40° C. for 30 min and benzyl bromide was dropwise added. The reaction mixture was stirred at 40° C. for another 3 h. The mixture was diluted with EtOAc and washed with water, 1N HCl and saturated $NaHCO_3$. The organic phase was dried over $Na_2SO_4$ and concentrated. The resulting residue was purified by silica gel preparative TLC using $CH_2Cl_2$:MeOH 98:2 as an eluent to afford the title compound (7 mg, 5%); MS m/z 347 $[C_{18}H_{16}Cl_2N_2O+H]^+$.

Example 16

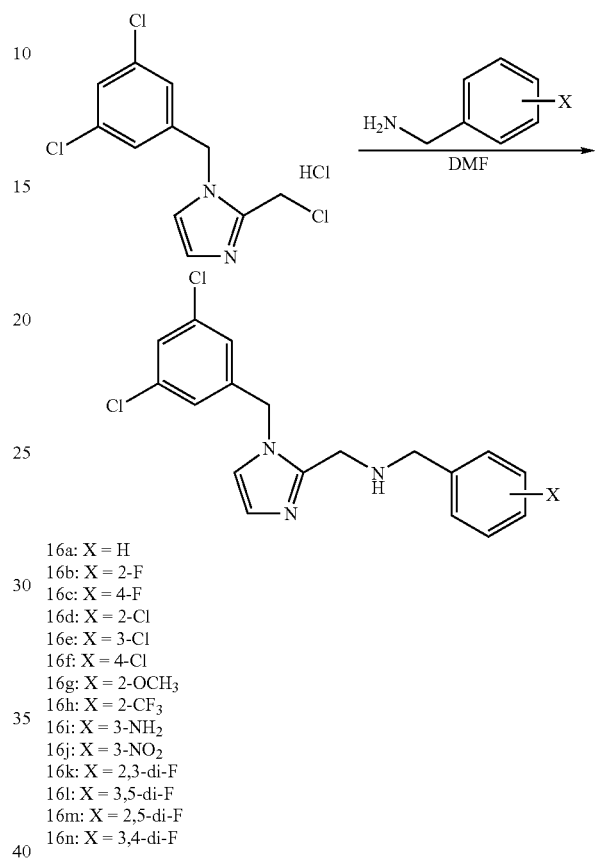

16a: X = H
16b: X = 2-F
16c: X = 4-F
16d: X = 2-Cl
16e: X = 3-Cl
16f: X = 4-Cl
16g: X = 2-OCH$_3$
16h: X = 2-CF$_3$
16i: X = 3-NH$_2$
16j: X = 3-NO$_2$
16k: X = 2,3-di-F
16l: X = 3,5-di-F
16m: X = 2,5-di-F
16n: X = 3,4-di-F

Preparation of 16a-n.

General procedure. To a solution of 2-Chloromethyl-1-(3,5-dichlorobenzyl)-1H-imidazole hydrochloride (see Example 1) in DMF was added the desired amine (3-5 eq). When an amine exists as a salt, an organic base such as N,N-diisopropylethylamine or triethylamine was added. The reaction mixture was stirred at room temperature for 2-3 h. The reaction mixture was diluted with EtOAc and washed with water (×4). The organic phase was dried over $Na_2SO_4$ and concentrated. The resulting residue was purified by silica gel preparative TLC using $CH_2Cl_2$:MeOH 95:5 as an eluent to afford the desired products.

The following compounds were prepared by the method described above:

Benzyl-[1-(3,5-dichloro-benzyl)-1H-imidazol-2-ylmethyl]-amine 16a); MS m/z 346 $[C_{18}H_{17}Cl_2N_3+H]^+$.
[1-(3,5-Dichloro-benzyl)-1H-imidazol-2-ylmethyl]-(2-fluoro-benzyl)-amine 16b); MS m/z 364 $[C_{18}H_{16}Cl_2FN_3+H]^+$.
[1-(3,5-Dichloro-benzyl)-1H-imidazol-2-ylmethyl]-(4-fluoro-benzyl)-amine (16c); MS m/z 364 $[C_{18}H_{16}Cl_2FN_3+H]^+$.
(2-Chloro-benzyl)-[1-(3,5-dichloro-benzyl)-1H-imidazol-2-ylmethyl]-amine 16d); MS m/z 380 $[C_{18}H_{16}Cl_3N_3+H]^+$.

(3-Chloro-benzyl)-[1-(3,5-dichloro-benzyl)-1H-imidazol-2-ylmethyl]-amine; MS m/z 380 [$C_{18}H_{16}Cl_3N_3$+H]$^+$.

(4-Chloro-benzyl)-[1-(3,5-dichloro-benzyl)-1H-imidazol-2-ylmethyl]-amine; MS m/z 380 [$C_{18}H_{16}Cl_3N_3$+H]$^+$.

[1-(3,5-Dichloro-benzyl)-1H-imidazol-2-ylmethyl]-(2-methoxy-benzyl)-amine; MS m/z 376 [$C_{19}H_{19}Cl_2N_3O$+H]$^+$.

[1-(3,5-Dichloro-benzyl)-1H-imidazol-2-ylmethyl]-(2-trifluoromethyl-benzyl)-amine; MS m/z 414 [$C_{19}H_{16}Cl_2F_3N_3$+H]$^+$.

3-({[1-(3,5-Dichloro-benzyl)-1H-imidazol-2-ylmethyl]-amino}-methyl)-phenylamine; MS m/z 361 [$C_{18}H_{18}Cl_2N_4$+H]$^+$.

[1-(3,5-Dichloro-benzyl)-1H-imidazol-2-ylmethyl]-(3-nitro-benzyl)-amine; MS m/z 391 [$C_{18}H_{16}Cl_2N_4O_2$+H]$^+$.

[1-(3,5-Dichloro-benzyl)-1H-imidazol-2-ylmethyl]-(2,3-difluoro-benzyl)-amine; MS m/z 382 [$C_{18}H_{15}Cl_2F_2N_3$+H]$^+$.

[1-(3,5-Dichloro-benzyl)-1H-imidazol-2-ylmethyl]-(3,5-difluoro-benzyl)-amine MS m/z 382 [$C_{18}H_{15}Cl_2F_2N_3$+H]$^+$.

[1-(3,5-Dichloro-benzyl)-1H-imidazol-2-ylmethyl]-(2,5-difluoro-benzyl)-amine; MS m/z 382 [$C_{18}H_{15}Cl_2F_2N_3$+H]$^+$.

[1-(3,5-Dichloro-benzyl)-1H-imidazol-2-ylmethyl]-(3,4-difluoro-benzyl)-amine; MS m/z 382 [$C_{18}H_{15}Cl_2F_2N_3$+H]$^+$.

Example 17

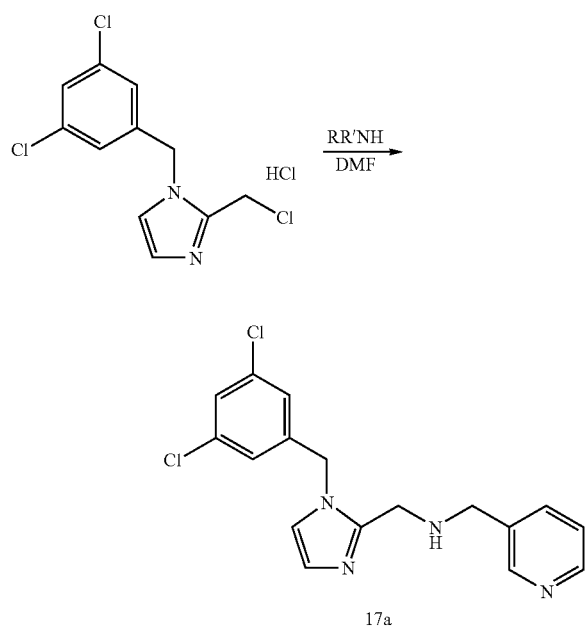

General procedure. To a solution of 2-chloromethyl-1-(3,5-dichlorobenzyl)-1H-imidazole hydrochloride (see Example 1) in DMF was added amine (3-5 eq). When an amine exists as a salt, an organic base such as N,N-Diisopropylethylamine or triethylamine was added. The reaction mixture was stirred at room temperature for 2-48 h until the starting material was consumed. The reaction mixture was diluted with EtOAc and washed with water (×2). The organic phase was dried over $Na_2SO_4$ and concentrated. The resulting residue was purified by silica gel preparative TLC using $CH_2Cl_2$:MeOH 95:5 as an eluent to afford the desired products.

[1-(3,5-Dichloro-benzyl)-1H-imidazol-2-ylmethyl]-pyridin-3-ylmethyl-amine; MS m/z 347 [$C_{17}H_{16}Cl_2N_4$+H]$^+$.

Benzyl-[1-(3,5-dichloro-benzyl)-1H-imidazol-2-ylmethyl]-methyl-amine; MS m/z 360 [$C_{19}H_{19}Cl_2N_3$+H]$^+$.

Benzyl-[1-(3,5-dichloro-benzyl)-1H-imidazol-2-ylmethyl]-ethyl-amine; MS m/z 374 [$C_{20}H_{21}Cl_2N_3$+H]$^+$.

2-{Benzyl-[1-(3,5-dichloro-benzyl)-1H-imidazol-2-ylmethyl]-amino}-ethanol; MS m/z 390 [$C_{20}H_{21}Cl_2N_3O$+H]$^+$.

Example 18

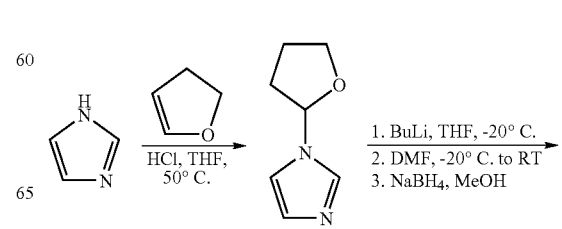

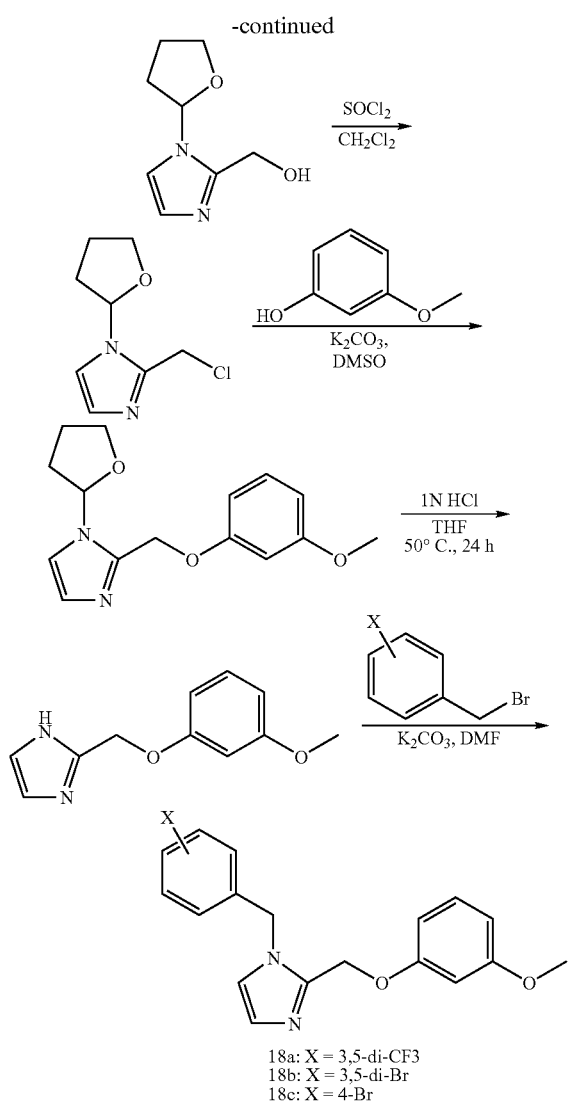

[1-(Tetrahydro-furan-2-yl)-1H-imidazol-2-yl]-methanol was prepared from imidazole and dihydrofuran according to a procedure in the literature (Song et al. *J. Org Chem.* 1999, 64, 1859-1867). To a solution of [1-(tetrahydro-furan-2-yl)-1H-imidazol-2-yl]-methanol (7.0 g, 41.7 mmol) in dry $CH_2Cl_2$ (80 mL) at 0° C. under $N_2$ was added dropwise $SOCl_2$. The resulting solution was stirred at 0° C. for 3 h and allowed to warm up gradually to ambient temperature overnight. The mixture was cooled in a dry ice-ethylene glycol bath before saturated $NaHCO_3$ (200 mL) was added carefully. The resulting mixture was extracted with $CH_2Cl_2$ (3×100 mL). The combined extracts were dried ($Na_2SO_4$) and concentrated in vacuo. The crude 2-chloromethyl-1-(tetrahydro-furan-2-yl)-1H-imidazole hydrochloride (5.7 g, 74%) was obtained as a brown oil; ESI MS m/z 187 $[C_8H_{11}ClN_2O+H]^+$. The product was used immediately in the next reaction.

To a mixture of 2-chloromethyl-1-(tetrahydro-furan-2-yl)-1H-imidazole hydrochloride, (5.7 g, 30.6 mmol), 3-methoxyphenol (7.6 g, 61.2 mmol) and DMSO (30 mL) was added $K_2CO_3$ (12.7 g, 91.8 mmol). The mixture was stirred at ambient temperature under $N_2$ overnight. Water (100 mL) was added and the mixture was extracted with $CH_2Cl_2$ (3×100 mL). The combined $CH_2Cl_2$ extracts were washed with 2N NaOH, dried over $Na_2SO_4$ and concentrated in vacuo. The residue was purified by column chromatography (silica gel, 1:2 hexane/EtOAc) to provide the desired 2-(3-methoxy-phenoxymethyl)-1-(tetrahydro-furan-2-yl)-1H-imidazole (3.49 g, 41%) as a colorless oil: ESI MS m/z 275 $[C_{15}H_{18}N_2O_3+H]^+$.

A mixture of 2-(3-methoxy-phenoxymethyl)-1-(tetrahydro-furan-2-yl)-1H-imidazole 1N HCl (20 mL) and THF (20 mL) was stirred at 50° C. for 24 h. Saturated $NaHCO_3$ was added to adjust the pH to 8. The mixture was extracted with $CH_2Cl_2$ (3×100 mL). The combined $CH_2Cl_2$ extracts were dried over $Na_2SO_4$ and concentrated in vacuo. The residue was purified by column chromatography (silica gel, 1:2 hexane/EtOAc) to provide the desired 2-(3-methoxy-phenoxymethyl)-1H-imidazole (2.40 g, 92%) as a white solid: ESI MS m/z 205 $[C_{11}H_{12}N_2O_2+H]^+$.

General Procedures.

To a solution of 2-(3-methoxy-phenoxymethyl)-1H-imidazole in DMF was added freshly ground $K_2CO_3$ followed by benzyl bromide. The reaction mixture was stirred at room temperature until most of starting material was consumed. The reaction mixture was then diluted with ethyl acetate and washed with water. The organic phase was dried over $MgSO_4$ and concentrated. The resulting residue was purified by silica gel preparative TLC using $CH_2Cl_2$:MeOH 95:5 as an eluent to afford the desired products.

1-(3,5-Bis-trifluoromethyl-benzyl)-2-(3-methoxy-phenoxymethyl)-1H-imidazole (18a); MS m/z 430 $[C_{20}H_{16}F_6N_2O_2+H]^+$.

1-(3,5-Dibromo-benzyl)-2-(3-methoxy-phenoxymethyl)-1H-imidazole (18b), MS m/z 452 $[C_{18}H_{16}Br_2N_2O_2+H]^+$.

1-(4-Bromo-benzyl)-2-(3-methoxy-phenoxymethyl)-1H-imidazole (18c); MS m/z 373 $[C_{18}H_{17}BrN_2O_2+H]^+$.

Example 19

1-(3-Chloro-5-iodo-benzyl)-2-(4-fluoro-phenoxymethyl)-1H-imidazole

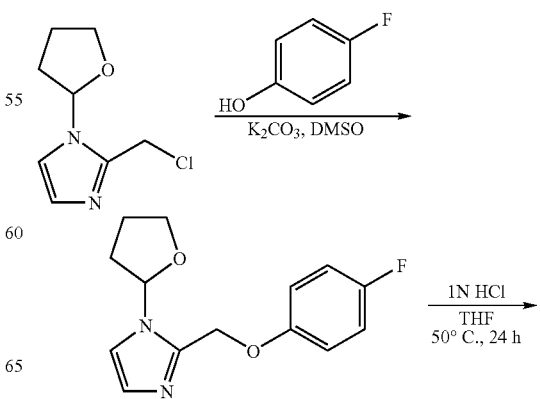

-continued

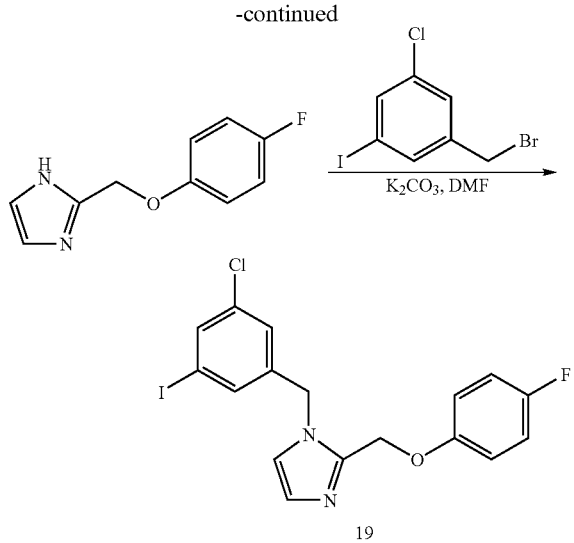

19

2-(4-Fluoro-phenoxymethyl)-1H-imidazole was prepared following a similar procedure for the preparation of 2-(3-Methoxy-phenoxymethyl)-1H-imidazole (see Example 18) using 4-fluorophenol in place of 3-methoxyphenol to provide a white solid (1.69 g, 85% for 2 steps); ESI MS m/z 193 $[C_{10}H_9FN_2O+H]^+$.

Methyl 3-chloro-5-iodobenzoate was dissolved in anhydrous THF and cooled to 0° C. 1M DIBAL in toluene (13 mL) was added slowly to the reaction solution at that temperature. The reaction mixture was stirred overnight at room temperature. Next morning, another 10 mL of 1M DIBAL in toluene was added and stirred for additional 4 h. When the reaction was complete, the reaction mixture was quenched with saturated solution of potassium sodium tartrate. The reaction mixture wad then extracted with ethyl acetate (×3). The combined organic extracts were dried over $Na_2SO_4$ and concentrated to afford the desired (3-chloro-5-iodo-phenyl)-methanol (2.7 g, 98%).

To a stirred ice-cooled solution of triphenylphosphine in 10 mL of $CH_2Cl_2$ was added dropwise a solution of bromine in 5 ml of $CH_2Cl_2$. After the reaction mixture was stirred at room temperature for 30 min and cooled at ice bath temperature, a solution of the above (3-chloro-5-iodo-phenyl)-methanol in 15 ml of $CH_2Cl_2$ was added dropwise. The reaction mixture was stirred 0° C. for another 1 h and concentrated. The residue was washed with hexane several times and the combined hexane layer was concentrated to give 1-bromomethyl-3-chloro-5-iodo-benzene (1.2 g, 97%).

To a solution of 2-(4-fluoro-phenoxymethyl)-1H-imidazole in DMF was added freshly ground $K_2CO_3$ followed by bromomethyl-3-chloro-5-iodo-benzene. The reaction mixture was stirred at room temperature until most of starting material was consumed. The reaction mixture was then diluted with ethyl acetate and washed with water. The organic phase was dried over $MgSO_4$ and concentrated. The resulting residue was purified by silica gel preparative TLC using $CH_2Cl_2$:MeOH 95:5 as an eluent to afford the title compound (275 mg, 60%); MS m/z 442 $[C_{17}H_{13}ClFIN_2O+H]^+$.

Example 20

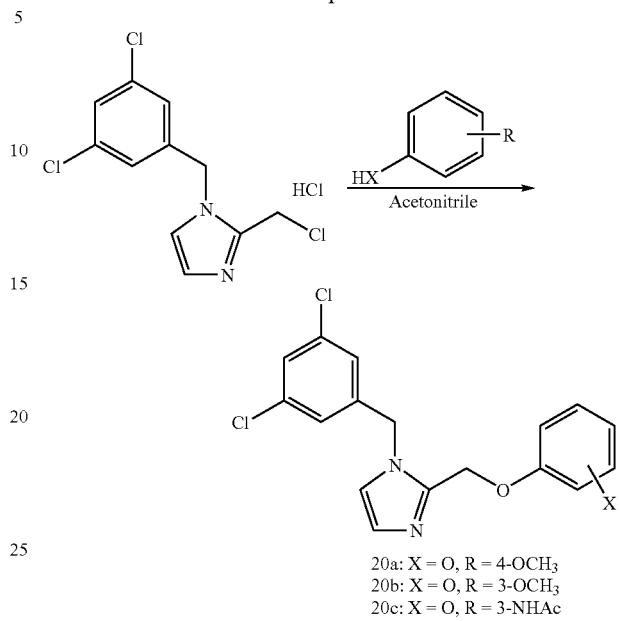

20a: X = O, R = 4-OCH$_3$
20b: X = O, R = 3-OCH$_3$
20c: X = O, R = 3-NHAc

4-Methoxyphenol (24 mg, 0.19 mmol) was dissolved in acetonitrile (2 mL). TBD-methyl polystyrene resin (296 mg, 0.8 mmol) was added and the reaction was shaken. After 15 min, 2-(chloromethyl)-1-(3,5-dichlorobenzyl)-1H-imidazole hydrochloride (see Example 1) was added and the reaction was shaken. After 48 h, the reaction was filtered. MeOH (4 mL) was added to the resin and the mixture was shaken at room temperature. After 15 minutes, the mixture was filtered, combined with the previous filtrate and concentrated in vacuo to yield 27 mg of an off-white solid. Preparative chromatography (silica, 40:1 $CH_2Cl_2$/MeOH) provided 1-(3,5-Dichloro-benzyl)-2-(4-methoxy-phenoxymethyl)-1H-imidazole (11 mg, 19%); MS m/z 363 $[C_{18}H_{16}Cl_2N_2O_2+H]^+$.

The following compounds were prepared using the above procedure and the appropriate substituted phenol:
1-(3,5-Dichloro-benzyl)-2-(3-methoxy-phenoxymethyl)-1H-imidazole; MS m/z 363 $[C_{18}H_{16}Cl_2N_2O_2+H]^+$.
N-{3-[1-(3,5-Dichloro-benzyl)-1H-imidazol-2-ylmethoxy]-phenyl}-acetamide; MS m/z 390 $[C_{19}H_{17}Cl_2N_3O_2+H]^+$.

Example 21

3-[1-(3,5-Dichloro-benzyl)-1H-imidazol-2-ylmethoxy]-phenylamine

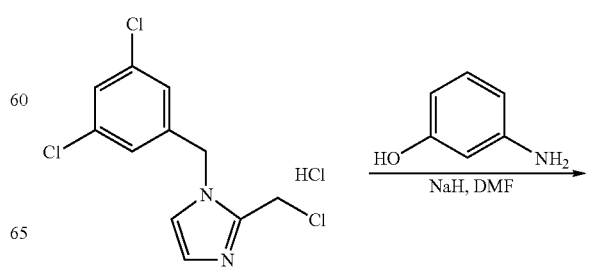

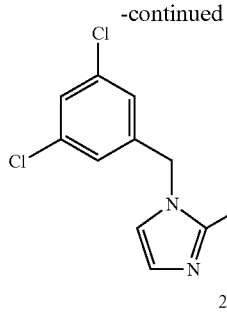

21

3-Aminophenol (87 mg, 0.8 mmol) was dissolved in DMF and NaH (33 mg, 0.83 mmol) was added. After 10 min, 2-(chloromethyl)-1-(3,5-dichlorobenzyl)-1H-imidazole hydrochloride (see Example 1) (100 mg, 0.32 mmol) was added in one portion. After 20 min, the reaction was partitioned between water (10 mL) and EtOAc (10 mL). The layers were separated and the aqueous layer was re-extracted with EtOAc (1×10 mL). The combined organic layers were washed with 1M NaOH (3×10 mL), water (10 mL) and brine, dried over MgSO$_4$, filtered and concentrated to yield the title compound as a pale yellow oil (78 mg, 70%); MS m/z 348 $[C_{17}H_{15}Cl_2N_3O+H]^+$.

Example 22

2-Cyclohexyloxymethyl-1-(3,5-dichloro-benzyl)-1H-imidazole

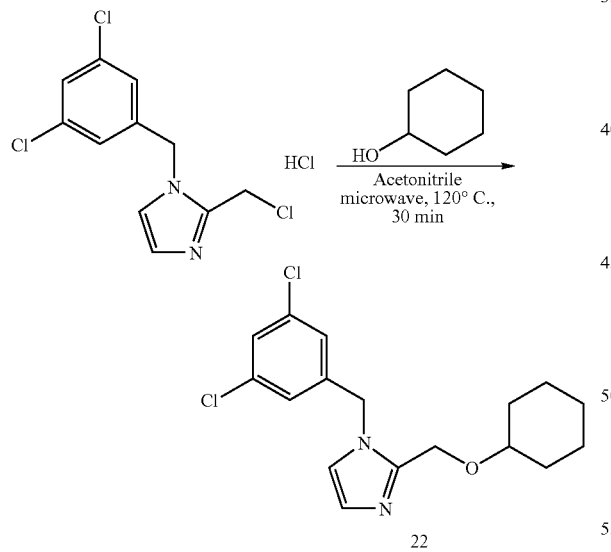

2-(Chloromethyl)-1-(3,5-dichlorobenzyl)-1H-imidazole hydrochloride (see Example 1) (100 mg, 0.32 mmol), cyclohexanol (160 mg, 1.6 mmol) and acetonitrile (1 mL) were combined in a Smith Process Vial. The reaction mixture was heated in a SmithSynthesizer™ (Personal Chemistry) microwave at 120° C. for 30 min. The heterogeneous solution was filtered and the solid was washed with acetonitrile. The filtrate was concentrated and the resulting semi-solid was partitioned between CH$_2$Cl$_2$ (10 mL) and 5% Na$_2$CO$_3$ (5 mL). The aqueous layer was extracted with CH$_2$Cl$_2$ (2×10 mL). The combined organic layers were dried over MgSO$_4$, filtered and concentrated to afford the desired product (11 mg, 10%); MS m/z 339 $[C_{17}H_{20}Cl_2N_2O+H]^+$.

Example 23

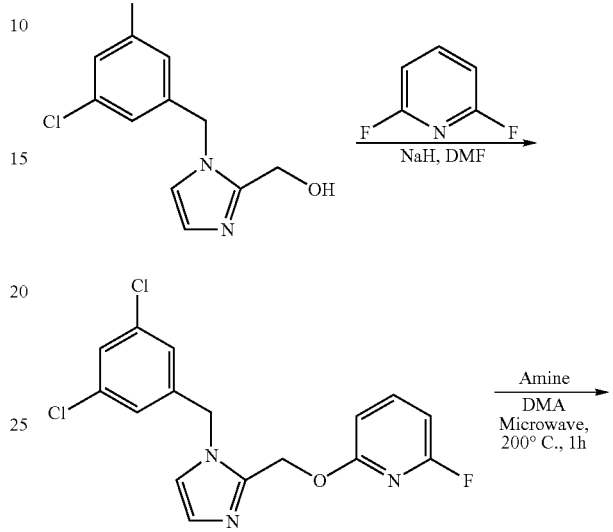

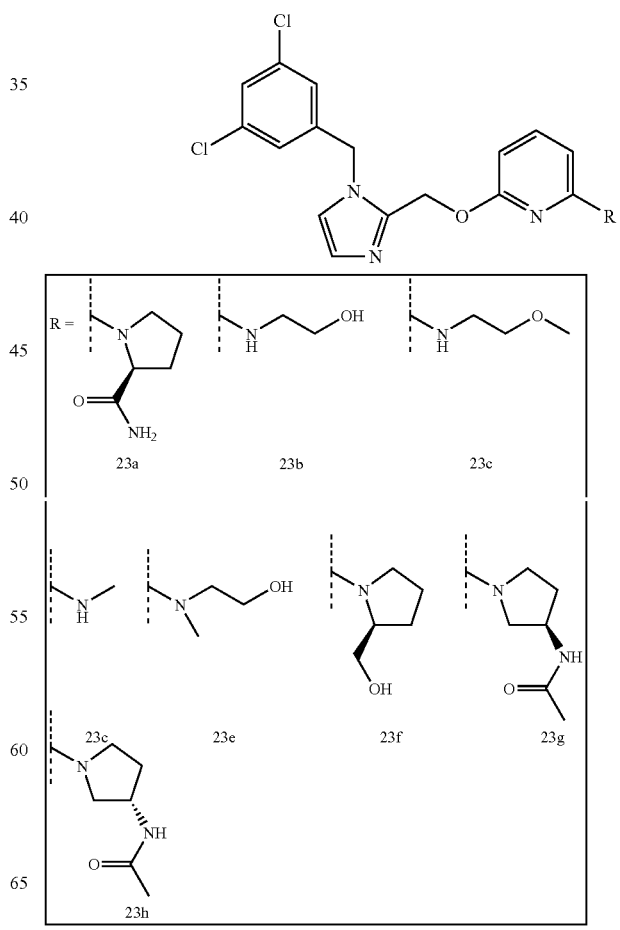

[1-(3,5-Dichloro-benzyl)-1H-imidazol-2-yl]-methanol (300 mg, 1.17 mmol) was dissolved in DMF and NaH (46 mg, 1.17 mmol) was added under $N_2$ atmosphere. After 20 minutes, 2,6-di-fluoropyridine (0.11 mL, 1.17 mmol) was added. The reaction mixture was stirred at room temperature for 1 h. The reaction was partitioned between EtOAc (50 mL) and water (50 mL). The layers were separated and the aqueous layer was extracted with EtOAc (2×75 mL). The combined organic extracts were washed with water (2×70 mL) and brine, dried over $MgSO_4$, filtered and concentrated to yield a yellow solid. Chromatography (silica, 40:1 $CH_2Cl_2$/MeOH) afforded 2-[1-(3,5-dichlorobenzyl)-1H-imidazol-2-yl-methoxy]-6-fluoro-pyridine (270 mg, 66%).

2-[1-(3,5-Dichlorobenzyl)-1H-imidazol-2-ylmethoxy]-6-fluoro-pyridine (100 mg, 0.28 mmol), L-prolineamide (900 mg, 7.88 mmol) and DMA (2 mL) were combined in a Smith reaction tube and heated in a SmithSynthesizer™ (Personal Chemistry) microwave for 60 min at 200° C. The reaction was diluted with water (10 mL) and EtOAc (10 mL). The layers were separated. The aqueous layer was extracted with EtOAc (3×5 mL). The combined organic extracts were washed with water (3×5 mL) and brine, dried over $MgSO_4$, filtered and concentrated to yield 130 mg of a yellow oil. Chromatography (silica, 20:1 $CH_2Cl_2$:MeOH) afforded 1-{6-[1-(3,5-dichloro-benzyl)-1H-imidazol-2-ylmethoxy]-pyridin-2-yl}-pyrrolidine-2-carboxylic acid amide, 23a as a colorless oil which slowly solidified (102 mg, 81%); MS m/z 446 $[C_{21}H_{21}Cl_2N_5O_2+H]^+$.

The above procedure was used with the appropriate amine in place of L-prolineamide to prepare the following compounds:

2-{6-[1-(3,5-Dichloro-benzyl)-1H-imidazol-2-ylmethoxy]-pyridin-2-ylamino}-ethanol; MS m/z 393 $[C_{18}H_{18}Cl_2N_4O_2+H]^+$.
{6-[1-(3,5-Dichloro-benzyl)-1H-imidazol-2-ylmethoxy]-pyridin-2-yl}-(2-methoxy-ethyl)-amine; MS m/z 407 $[C_{19}H_{20}Cl_2N_4O_2+H]^+$.
{6-[1-(3,5-Dichloro-benzyl)-1H-imidazol-2-ylmethoxy]-pyridin-2-yl}-methyl-amine; MS m/z 363 $[C_{17}H_{16}Cl_2N_4O+H]^+$.
2-({6-[1-(3,5-Dichloro-benzyl)-1H-imidazol-2-ylmethoxy]-pyridin-2-yl}-methyl-amino)-ethanol; MS m/z 407 $[C_{19}H_{20}Cl_2N_4O_2+H]^+$.
((S)-1-{6-[1-(3,5-Dichloro-benzyl)-1H-imidazol-2-yl-methoxy]-pyridin-2-yl}-pyrrolidin-2-yl)-methanol; MS m/z 433 $[C_{21}H_{22}Cl_2N_4O_2+H]^+$.
N-((R)-1-{6-[1-(3,5-Dichloro-benzyl)-1H-imidazol-2-yl-methoxy]-pyridin-2-yl}-pyrrolidin-3-yl)-acetamide; MS m/z 460 $[C_{22}H_{23}Cl_2N_5O_2+H]^+$.
N-((S)-1-{6-[1-(3,5-Dichloro-benzyl)-1H-imidazol-2-yl-methoxy]-pyridin-2-yl}-pyrrolidin-3-yl)-acetamide; MS m/z 460 $[C_{22}H_{23}Cl_2N_5O_2+H]^+$.

Example 24

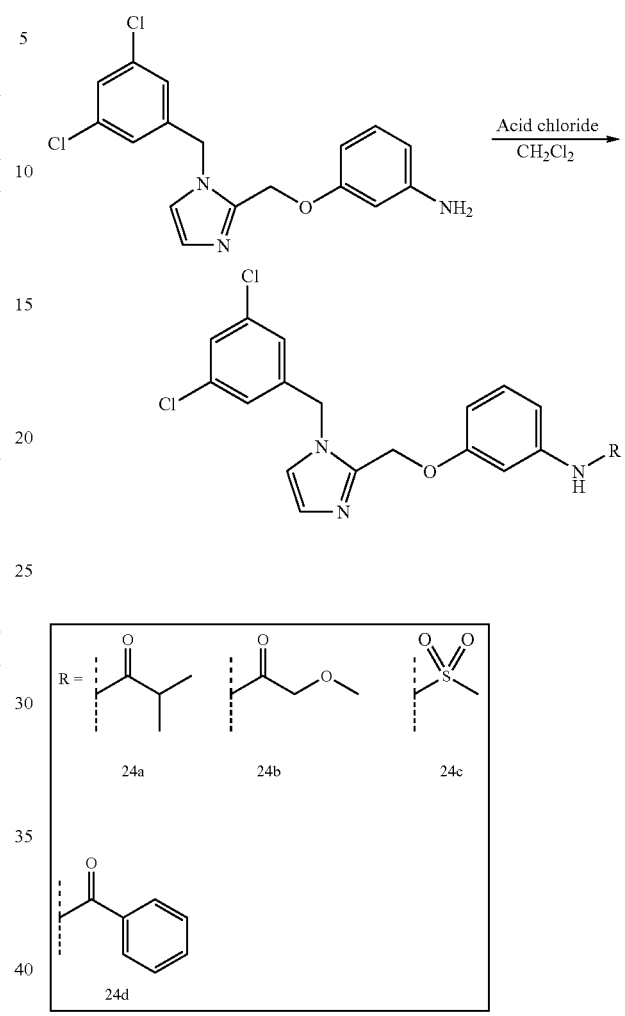

Isobutyryl chloride (11 mg, 0.1 mmol) was added to a solution of 3-[1-(3,5-dichloro-benzyl)-1H-imidazol-2-yl-methoxy]-phenylamine (see Example 21) (30 mg, 0.09 mmol) in $CH_2Cl_2$ (1 mL). The reaction was shaken at room temperature. After 72 h, trisamine resin (79 mg, 0.1 mmol) was added and the reaction was shaken for another 4 h. The reaction was filtered and the resin was washed with $CH_2Cl_2$ (2 mL). The filtrates were combined and concentrated in vacuo. Preparative TLC (silica, 20:1 $CH_2Cl_2$:MeOH, Rf=0.4) provided N-{3-[1-(3,5-dichloro-benzyl)-1H-imidazol-2-yl-methoxy]-phenyl}-isobutyramide, 24a as a white solid (15 mg, 40%); MS m/z 418 $[C_{21}H_{21}Cl_2N_3O_2+H]^+$.

The same procedure using the appropriate acid chloride was applied to afford the following compounds;

N-{3-[1-(3,5-Dichloro-benzyl)-1H-imidazol-2-ylmethoxy]-phenyl}-2-methoxy-acetamide; MS m/z 420 $[C_{20}H_{19}Cl_2N_3O_3+H]^+$.
N-{3-[1-(3,5-Dichloro-benzyl)-1H-imidazol-2-ylmethoxy]-phenyl}-methanesulfonamide; MS m/z 426 $[C_{18}H_{17}Cl_2N_3O_3S+H]^+$.

N-{3-[1-(3,5-Dichloro-benzyl)-1H-imidazol-2-ylmethoxy]-phenyl}-benzamide; MS m/z 452 $[C_{24}H_{19}Cl_2N_3O_2+H]^+$.

Example 25

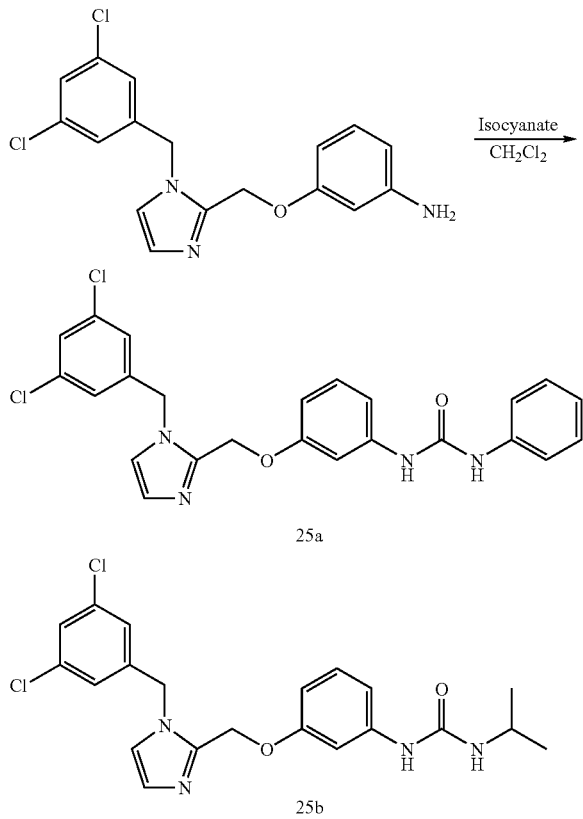

A solution of 3-[1-(3,5-Dichloro-benzyl)-1H-imidazol-2-ylmethoxy]-phenylamine (see Example 21) in $CH_2Cl_2$ and phenyl isocyanate in $CH_2Cl_2$ (0.4 mL) were combined and the reaction was shaken at room temperature. After 72 h, LC/MS showed the reaction had progressed to completion. Trisamine resin was added and the reaction was shaken at room temperature. After 4 h, the reaction was filtered and the resin was washed with $CH_2Cl_2$ (2 mL). The filtrates were combined and concentrated in vacuo. Preparatory TLC (silica, 20:1 $CH_2Cl_2$: MeOH; Rf=0.5) yielded 1-{3-[1-(3,5-dichloro-benzyl)-1H-imidazol-2-ylmethoxy]-phenyl}-3-phenyl-urea (25a) as a white solid (22 mg, 52%); MS m/z 467 $[C_{24}H_{20}Cl_2N_4O_2+H]^+$.

The same procedure using isopropyl isocyanate was applied to afford the following compound;

1-{3-[1-(3,5-Dichloro-benzyl)-1H-imidazol-2-ylmethoxy]-phenyl}-3-isopropyl-urea; MS m/z 433 $[C_{21}H_{22}Cl_2N_4O_2+H]^+$.

Description of Biological Properties

The biological properties of representative compounds of the formula I were investigated by way of the experimental protocol described below.

Assay to Determine Inhibition of LFA-1 Binding to ICAM-1

Purpose of Assay:

This assay protocol is designed to study the direct antagonism, by a test compound, of the interaction of the CAM, ICAM-1 with the Leukointegrin CD18/CD11a (LFA-1).

Description of Assay Protocol:

LFA-1 is immunopurified using the TS2/4 antibody from a 20 g pellet of human JY or SKW3 cells, utilizing a protocol previously described (Dustin, M. J.; et al., *J. Immunol.* 1992, 148, 2654-2660). The LFA-1 is purified from SKW3 lysates by immunoaffinity chromatography on TS2/4 LFA-1 mAb Sepharose and eluted at pH 11.5 in the presence of 2 mM $MgCl_2$ and 1% octylglucoside. After collection and neutralization of fractions from the TS2/4 column, samples are pooled and precleared with Protein G agarose.

A soluble form of ICAM-1 is constructed, expressed, purified and characterized as previously described (Marlin, S.; et al., *Nature,* 1990, 344, 70-72 and see Arruda, A.; et al., *Antimicrob. Agents Chemother.* 1992, 36, 1186-1192). Briefly, isoleucine 454 which is located at the putative boundary between domain 5 of the ectodomain and the transmembrane domain, is changed to a stop codon using standard oligonucleotide-directed mutagenesis. This construction yields a molecule identical with the first 453 amino acids of membrane bound ICAM-1. An expression vector is created with a hamster dihydrofolate reductase gene, a neomycin-resistance marker, and the coding region of the sICAM-1 construct described above, along with the promoter, splice signals, and polyadenylation signal of the SV40 early region. The recombinant plasmid is transfected into CHO DUX cells using standard calcium phosphate methods. Cells are passaged in selective media (G418) and colonies secreting sICAM-1 are amplified using methotrexate. sICAM-1 is purified from serum-free media using traditional non-affinity chromatographic techniques, including ion exchange and size exclusion chromatography.

LFA-1 binding to ICAM-1 is monitored by first incubating sICAM-1 at 40 μg/mL in Dulbecco's phosphate buffered saline with calcium and magnesium, additional 2 mM $MgCl_2$ and 0.1 mM PMSF (Diluting Buffer) in a 96-well plate for 30 min at room temperature. Plates are then blocked by the addition of 2% (w/v) bovine serum albumin in Diluting Buffer for 37° C. for 1 h. Blocking solution is removed from wells, and test compounds are diluted and then added followed by the addition of approximately 25 ng of immunoaffinity purified LFA-1. The LFA-1 is incubated in the presence of test compound and ICAM-1 at 37° C. for 1 h. Wells are washed 3 times with Diluting Buffer. The bound LFA-1 is detected by the addition of a polyclonal antibody directed against a peptide corresponding to the CD18 cytoplasmic tail in a 1:100 dilution with Diluting Buffer and 1% BSA and allowed to incubate for 45 min at 37° C. Wells are washed 3 times with Diluting Buffer and the bound polyclonal antibody is detected by the addition of a 1:4000 dilution of horse radish peroxidase conjugated to goat immunoglobulin directed against rabbit immunoglobulin. This reagent is allowed to incubate for 20 min at 37° C., wells are washed as above and the substrate for the horse radish peroxidase is added to each well to develop a quantitative colorimetric signal proportional to the amount of LFA-1 bound to sICAM-1. Soluble ICAM-1 (60 µg/mL) is used as a positive control for inhibition of the LFA-1/ICAM-1 interaction. The lack of the addition of LFA-1 to the binding assay is used as a background control for all samples. A dose-response curve is obtained for all test compounds.

All compounds made in the above examples were tested in this assay and each found to have a $K_d$<10 µM.

Description of Therapeutic Use

The novel small molecules of formula I provided by the invention inhibit the ICAM-1/LFA-1 dependent homotypic aggregation of human lymphocytes and human lymphocyte adherence to ICAM-1. These compounds have therapeutic utility in the modulation of immune cell activation/proliferation, e.g. as competitive inhibitors of intercellular ligand/receptor binding reactions involving CAMs and Leukointegrins. To be more specific, the compounds of the invention may be used to treat certain inflammatory conditions, including conditions resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The compounds of the invention may also be used in treating asthma or as an adjunct to minimize toxicity with cytokine therapy in the treatment of cancers. In general these compounds may be employed in the treatment of those diseases currently treatable through steroid therapy.

Thus, another aspect of the invention is the provision of a method for the treatment or prophylaxis of the above-described conditions through the adminstration of therapeutic or prophylactic amounts of one or more compounds of the formula I.

In accordance with the method provided by the invention, the novel compounds of formula I may be administered for either a prophylactic or therapeutic purpose either alone or with other immunosuppressive or antiinflammatory agents. When provided prophylactically, the immunosuppressive compound(s) are provided in advance of any inflammatory response or symptom (for example, prior to, at, or shortly after the time of an organ or tissue transplant but in advance of any symptoms of organ rejection). The prophylactic administration of a compound of the formula I serves to prevent or attenuate any subsequent inflammatory response (such as, for example, rejection of a transplanted organ or tissue, etc.). The therapeutic administration of a compound of the formula I serves to attenuate any actual inflammation (such as, for example, the rejection of a transplanted organ or tissue).

Thus, in accordance with the invention, a compound of the formula I can be administered either prior to the onset of inflammation (so as to suppress an anticipated inflammation) or after the initiation of inflammation.

The novel compounds of the formula I may, in accordance with the invention, be administered in single or divided doses by the oral, parenteral or topical routes. A suitable oral dosage for a compound of formula I would be in the range of about 0.1 mg to 10 g per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical compositions which contain them in association with one or more compatible pharmaceutical carrier materials. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical compositions can be prepared in a conventional manner and finished dosage forms can be solid dosage forms, for example, tablets, dragees, capsules, and the like, or liquid dosage forms, for example solutions, suspensions, emulsions and the like. The pharmaceutical compositions may be subjected to conventional pharmaceutical operations such as sterilization. Further, the pharmaceutical compositions may contain one or more conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered topically or by suppository.

Formulations

Compounds of the formula I can be formulated for therapeutic administration in a number of ways. Descriptions of several exemplary formulations are given below.

Example A

Capsules or Tablets

| Example A-1 | | Example A-2 | |
|---|---|---|---|
| Ingredients | Quantity | Ingredients | Quantity |
| Compound of formula I | 250 mg | Compound of formula I | 50 mg |
| Starch | 160 mg | Dicalcium Phosphate | 160 mg |
| Microcrys. Cellulose | 90 mg | Microcrys. Cellulose | 90 mg |
| Sodium Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of formula I is blended into a powder mixture with the premixed excipient materials as identified above with the exception of the lubricant. The lubricant is then blended in and the resulting blend compressed into tablets or filled into hard gelatin capsules.

Example B

Parenteral Solutions

| Ingredients | Quantity |
|---|---|
| Compound of formula I | 500 mg |
| PEG 400 | 40% by volume |
| Ethyl Alcohol | 5% by volume |
| Saline | 55% by volume |

The excipient materials are mixed and then added to one of the compounds of formula I in such volume as is necessary for dissolution. Mixing is continued until the solution is clear. The solution then filtered into the appropriate vials or ampoules and sterilized by autoclaving.

Example C

Suspension

| Ingredients | Quantity |
|---|---|
| Compound of formula I | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 mL |

The excipient materials are mixed with the water and thereafter one of the compounds of formula I is added and mixing is continued until the suspension is homogeneous. The suspension is then transferred into the appropriate vials or ampoules.

Example D

Topical Formulation

| Ingredients | Quantity |
|---|---|
| Compound of formula I | 5% by weight |
| Tefose 63 | 13% by weight |
| Labrafil M 1944 CS | 3% by weight |
| Paraffin Oil | 8% by weight |
| Methylparaben (MP) | 0.15% by weight |
| Propylparaben (PP) | 0.05% by weight |
| Deionized water | q.s. to 100 |

The proper amounts of Tefose 63, Labrafil M 1944 CS, Paraffin oil and water are mixed and heated at 75° C. until all components have melted. The mixture is then cooled to 50° C. with continuous stirring. Methylparaben and propylparaben are added with mixing and the mixture is cooled to ambient temperature. The compound of formula I is added to the mixture and blended well.

We claim:

1. A compound of formula I

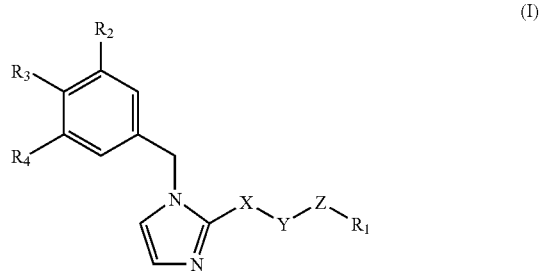

(I)

wherein:
X is —CH$_2$—,
Y is a group of the formula —NR$_7$—, wherein R$_7$ is
  (A) hydrogen atom or
  (B) C$_{1-3}$alkyl group optionally substituted with:
    (i) oxo, or
    (ii) a group of the formula —NR$_9$R$_{10}$, wherein R$_9$ and R$_{10}$ are each independently:
      (a) a hydrogen atom,
      (b) a C$_{1-2}$alkylcarbonyl group, or
      (c) a C$_{1-2}$alkyloxycarbonyl,
Z is —CH$_2$—,
R$_1$ is phenyl optionally substituted with one to two fluorine atoms,
R$_2$ is a chlorine atom,
R$_3$ is a hydrogen atom, and
R$_4$ is a chlorine atom;
or a pharmaceutically acceptable salt or ester thereof.

2. A compound of formula I

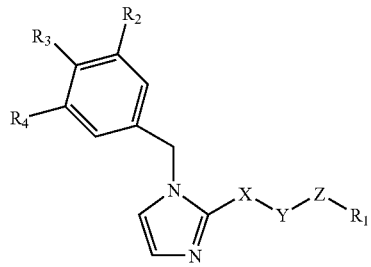

(I)

wherein:
X is —CH$_2$—,
Y is an oxygen atom,
Z is a bond,
R$_1$ is phenyl or pyridyl, optionally independently substituted with one to two of:
  (A) a fluorine or chlorine atom,
  (B) —OCH$_3$, or
  (C) a group of the formula —NR$_{12}$R$_{13}$, wherein R$_{12}$ and R$_{13}$ are each independently
    (i) hydrogen
    (ii) C$_{1-3}$alkyl optionally and independently substituted with
      (a) —N(CH$_3$)$_2$
      (b) —NHCOCH$_3$,
      (c) pyrrolidine, which is optionally substituted with C$_{1-2}$alkyl,
      (d) imidazole, or
      (e) pyridine, or
    (iii) cyclohexyl optionally substituted with —NH$_2$ or wherein R$_{12}$ and R$_{13}$ together constitute a saturated hydrocarbon bridge of 4 methylene groups which together with the nitrogen atom between them form a heterocyclic ring, wherein said heterocyclic ring is optionally substituted with —CONH$_2$ or —N(CH$_3$)COCH$_3$;
R$_2$ is a chlorine atom,
R$_3$ is a hydrogen atom, and
R$_4$ is a chlorine atom;
or a pharmaceutically acceptable salt or ester thereof.

3. A compound which is:
1-(3,5-Dichloro-benzyl)-2-(4-methoxy-phenoxymethyl)-1H-imidazole;
1-(3,5-Dichloro-benzyl)-2-(3-methoxy-phenoxymethyl)-1H-imidazole;
N-{3-[1-(3,5-Dichloro-benzyl)-1H-imidazol-2-ylmethoxy]-phenyl}-acetamide;
3-[1-(3,5-Dichloro-benzyl)-1H-imidazol-2-ylmethoxy]-phenylamine;
Benzyl-[1-(3,5-dichloro-benzyl)-1H-imidazol-2-ylmethyl]-amine;
2-Cyclohexyloxymethyl-1-(3,5-dichloro-benzyl)-1H-imidazole;
3-[1-(3,5-Dichloro-benzyl)-1H-imidazol-2-ylmethoxy]-phenol;
1-{3-[1-(3,5-Dichloro-benzyl)-1H-imidazol-2-ylmethoxy]-phenyl}-3-phenyl-urea;
N-{3-[1-(3,5-Dichloro-benzyl)-1H-imidazol-2-ylmethoxy]-phenyl}-isobutyramide;
1-(3,5-Bis-trifluoromethyl-benzyl)-2-(3-methoxy-phenoxymethyl)-1 H-imidazole;
1-(3,5-Dibromo-benzyl)-2-(3-methoxy-phenoxymethyl)-1H-imidazole;
[1-(3,5-Dichloro-benzyl)-1H-imidazol-2-ylmethyl]-(2-fluoro-benzyl)-amine;
N-{3-[1-(3,5-Dichloro-benzyl)-1H-imidazol-2-ylmethoxy]-phenyl}-2-methoxy-acetamide;
1-{3-[1-(3,5-Dichloro-benzyl)-1H-imidazol-2-ylmethoxy]-phenyl}-3-isopropyl-urea;
N-{3-[1-(3,5-Dichloro-benzyl)-1H-imidazol-2-ylmethoxy]-phenyl}-methanesulfonamide;
2-{6-[1-(3,5-Dichloro-benzyl)-1H-imidazol-2-ylmethoxy]-pyridin-2-ylamino}-ethanol;
1-(4-Bromo-benzyl)-2-(3-methoxy-phenoxymethyl)-1H-imidazole;
{6-[1-(3,5-Dichloro-benzyl)-1H-imidazol-2-ylmethoxy]-pyridin-2-yl}-(2-methoxy-ethyl)amine;
N-{3-[1-(3,5-Dichloro-benzyl)-1H-imidazol-2-ylmethoxy]-phenyl}-benzamide;
1-[1-(3,5-Dichloro-benzyl)-1H-imidazol-2-yl]-2-(3-methoxy-phenyl)-ethanone;
2-(3-Chloro-5-methoxy-phenoxymethyl)-1-(3,5-dichloro-benzyl)-1H-imidazole;
[1-(3,5-Dichloro-benzyl)-1H-imidazol-2-ylmethyl]-(3-fluoro-benzyl)-amine;
[1-(3,5-Dichloro-benzyl)-1H-imidazol-2-ylmethyl]-(4-fluoro-benzyl)-amine;
(2-Chloro-benzyl)-[1-(3,5-dichloro-benzyl)-1H-imidazol-2-ylmethyl]-amine;
(3-Chloro-benzyl)-[1-(3,5-dichloro-benzyl)-1H-imidazol-2-ylmethyl]-amine;
(4-Chloro-benzyl)-[1-(3,5-dichloro-benzyl)-1H-imidazol-2-ylmethyl]-amine;
[1-(3,5-Dichloro-benzyl)-1H-imidazol-2-ylmethyl]-(2-methoxy-benzyl)-amine;
{6-[1-(3,5-Dichloro-benzyl)-1H-imidazol-2-ylmethoxy]-pyridin-2-yl}-methyl-amine;
Benzyl-[1-(3,5-dichloro-benzyl)-1H-imidazol-2-ylmethyl]-methyl-amine;
[1-(3,5-Dichloro-benzyl)-1H-imidazol-2-ylmethyl]-(2,3-difluoro-benzyl)-amine;
[1-(3,5-Dichloro-benzyl)-1H-imidazol-2-ylmethyl]-(3,5-difluoro-benzyl)-amine;
Benzyl-[1-(3,5-dichloro-benzyl)-1H-imidazol-2-ylmethyl]-ethyl-amine;
2-{Benzyl-[1-(3,5-dichloro-benzyl)-1H-imidazol-2-ylmethyl]-amino}-ethanol;
[1-(3,5-Dichloro-benzyl)-1H-imidazol-2-ylmethyl]-(2-trifluoromethyl-benzyl)-amine;

2-(4-Chloro-3-methoxy-phenoxymethyl)-1-(3,5-dichloro-benzyl)-1H-imidazole;
[1-(3,5-Dichloro-benzyl)-1H-imidazol-2-ylmethyl]-(2,5-difluoro-benzyl)-amine;
[1-(3,5-Dichloro-benzyl)-1H-imidazol-2-ylmethyl]-pyridin-3-ylmethyl-amine;
[1-(3,5-Dichloro-benzyl)-1H-imidazol-2-yl]-(3-methoxybenzyl)-amine;
1-(3,5-Dichloro-benzyl)-2-(3-fluoro-5-trifluoromethyl-phenoxymethyl)-1H-imidazole;
[1-(3,5-Dichloro-benzyl)-1H-imidazol-2-ylmethyl]-(3,4-difluoro-benzyl)-amine;
2-({6-[1-(3,5-Dichloro-benzyl)-1H-imidazol-2-yl-methoxy]-pyridin-2-yl}-methyl-amino)ethanol;
Benzyl-[1-(3,5-dichloro-benzyl)-1H-imidazol-2-yl]-amine;
[1-(3,5-Dichloro-benzyl)-1H-imidazol-2-yl]-phenethyl-amine;
Benzyl-{1-[1-(3,5-dichloro-benzyl)-1H-imidazol-2-yl]ethyl}-amine;
[1-(3,5-Dichloro-benzyl)-1H-imidazol-2-ylmethyl]-(3-nitro-benzyl)-amine;
[1-(3,5-Dichloro-benzyl)-1H-imidazol-2-yl]-(4-fluoro-benzyl)-amine;
3-({[1-(3,5-Dichloro-benzyl)-1H-imidazol-2-ylmethyl]-amino}-methyl)-phenylamine;
[1-(3,5-Dichloro-benzyl)-1H-imidazol-2-ylmethyl]-indan-1-yl-amine;
[1-(3,5-Dichloro-benzyl)-1H-imidazol-2-ylmethyl]-(1,2,3,4-tetrahydro-naphthalen-1-yl)amine;
(S)-1-{6-[-1(3,5-Dichloro-benzyl)-1H-imidazol-2-yl-methoxy]-pyridin-2-yl}-pyrrolidine-2carboxylic acid amide;
1-(3-Chloro-5-iodo-benzyl)-2-(4-fluoro-phenoxymethyl)-1H-imidazole;
((S)-1-{6-[1-(3,5-Dichloro-benzyl)-1H-imidazol-2-yl-methoxy]-pyridin-2-yl}-pyrrolidin-2yl)-methanol;
N-((R)-1-{6-[1-(3,5-Dichloro-benzyl)-1H!-imidazol-2-ylmethoxy]-pyridin-2-yl}-pyrrolidin3-yl)-acetamide;
N-((S)-1-{6-[1-(3,5-Dichloro-benzyl)-1H-imidazol-2-yl-methoxy]-pyridin-2-yl}-pyrrolidin-3yl)-acetamide;
[1-(3,5-Dichloro-benzyl)-1H-imidazol-2-ylmethyl]-(3-fluoro-benzyl)-isopropyl-amine;
[1-(3,5-Dichloro-benzyl)-1H-imidazol-2-ylmethyl]-(3-fluoro-benzyl)-isobutyl-amine;
Cyclohexylmethyl-[1-(3,5-dichloro-benzyl)-1H-imidazol-2-ylmethyl]-(3-fluoro-benzyl)-amine;
[1-(3,5-Dichloro-benzyl)-1H-imidazol-2-ylmethyl]-(3-fluoro-benzyl)-(2-morpholin-4-ylethyl)-amine;
2-[[1-(3,5-Dichloro-benzyl)-1H-imidazol-2-ylmethyl]-(3-fluoro-benzyl)-amino]-acetamide;
{2-[[1-(3,5-Dichloro-benzyl)-1H-imidazol-2-ylmethyl]-(3-fluoro-benzyl)-amino]-ethyl}-carbamic acid tert-butyl ester;
N-[1-(3,5-Dichloro-benzyl)-1H-imidazol-2-ylmethyl]-N-(3-fluoro-benzyl)-N',N'-dimethylethane-1,2-diamine;
2-Benzyl-3-[1-(3,5-dichloro-benzyl)-1H-imidazol-2-yl]-propionic acid;
1-{3-[[1-(3,5-Dichloro-benzyl)-1H-imidazol-2-ylmethyl]-(3-fluoro-benzyl)-amino]propionyl}-piperidine-4-carboxylic acid amide;
3-[[1-(3,5-Dichloro-benzyl)-1H-imidazol-2-ylmethyl]-(3-fluoro-benzyl)-amino]propionamide;
N-{2-[[1-(3,5-Dichloro-benzyl)-1H-imidazol-2-ylmethyl]-(3-fluoro-benzyl)-amino]-ethyl}-acetamide;
N-{2-[[1-(3,5-Dichloro-benzyl)-1H-imidazol-2-ylmethyl]-(3-fluoro-benzyl)-amino]-ethyl}-benzamide;
[[1-(3,5-Dichloro-benzyl)-1H-imidazol-2-ylmethyl]-(3-fluoro-benzyl)-amino]-acetic acid methyl ester;
1-{2-[[-(3,5-Dichloro-benzyl)-1H-imidazol-2-ylmethyl]-(3-fluoro-benzyl)-amino]-ethyl}-3methyl-urea;
2-Benzyl-3-[1-(3,5-dichloro-benzyl)-1H-imidazol-2-yl]-propionamide;
N$^1$-[1-(3,5-Dichloro-benzyl)-1H-imidazol-2-ylmethyl] N$^1$-(3-fluoro-benzyl)-ethane-1,2-diamine;
2-Benzyl-3-[1-(3,5-dichloro-benzyl)-1H-imidazol-2-yl]-propionic acid ethyl ester;
1-(4-{2-[[1-(3,5-Dichloro-benzyl)-1H-imidazol-2-ylmethyl]-(3-fluoro-benzyl)-amino]-ethyl}-piperazin-1-yl)-ethanone;
[1-(3,5-Dichloro-benzyl)-1H-imidazol-2-ylmethyl]-(3-fluoro-benzyl)-(2-piperazin-1-ylethyl)-amine;
2-(2-Chloro-phenylsulfanylmethyl)-1-(3,5-dichloro-benzyl)-1H-imidazole;
2-(3-Chloro-phenylsulfanylmethyl)-1-(3,5-dichloro-benzyl)-1H-imidazole;
1-(3,5-Dichloro-benzyl)-2-(4-fluoro-phenoxymethyl)-1H-imidazole;
1-(3,5-Dichloro-benzyl)-2-(3-fluoro-phenylsulfanylmethyl)-1H-imidazole;
1-(3,5-Dichloro-benzyl)-2-(3,5-difluoro-phenoxymethyl)-1H-imidazole;
1-(3,5-Dichloro-benzyl)-2-(2,4-difluoro-phenoxymethyl)-1H-imidazole;
1-(3,5-Dichloro-benzyl)-2-(3-trifluoromethyl-phenoxymethyl)-1H-imidazole;
1-(3,5-Dichloro-benzyl)-2-phenoxymethyl-1H-imidazole;
1-(3,5-Dichloro-benzyl)-2-(3-fluoro-phenoxymethyl)-1H-imidazole;
1-{3-[1-(3,5-Dichloro-benzyl)-1H-imidazol-2-yl-methoxy]-phenyl}-ethanone;
1-(3,5-Dichloro-benzyl)-2-(2,3-difluoro-phenoxymethyl)-1H-imidazole;
1-(3,5-Dichloro-benzyl)-2-(3,4-difluoro-phenoxymethyl)-1H-imidazole;
N-{3-[1-(3,5-Dichloro-benzyl)-1H-imidazol-2-yl-methoxy]-phenyl}-acetamide;
1-(3,5-Dichloro-benzyl)-2-(3,4-dimethoxy-phenoxymethyl)-1H-imidazole;
1-(3,5-Dichloro-benzyl)-2-(5,6,7,8-tetrahydro-naphthalen-1-yloxymethyl)-1H-imidazole;
{3-[1-(3,5-Dichloro-benzyl)-1H-imidazol-2-ylmethoxy]-phenyl}-urea;
1-(3,5-Dichloro-benzyl)-2-[2-(4-methoxy-naphthalen-1-yloxy)-methyl]-1H-imidazole;
2-{6-[1-(3,5-Dichloro-benzyl)-1H-imidazol-2-yl-methoxy]-pyridin-2-ylamino}-propan-1-ol;
(S)-2-{6-[1-(3,5-Dichloro-benzyl)-1H-imidazol-2-yl-methoxy]-pyridin-2-ylamino}-4-methylpentan-1-ol;
3-{6-[1-(3,5-Dichloro-benzyl)-1H-imidazol-2-yl-methoxy]-pyridin-2-ylamino}-propane-1,2diol;
3-{6-[1-(3,5-Dichloro-benzyl)-1H-imidazol-2-yl-methoxy]-pyridin-2-ylamino}-propan-1-ol;
trans-4-{6-[1-(3,5-Dichloro-benzyl)-1H-imidazol-2-yl-methoxy]-pyridin-2-ylamino}cyclohexanol;
{6-[1-(3,5-Dichloro-benzyl)-1H-imidazol-2-ylmethoxy]-pyridin-2-yl}-(2-pyridin-3-yl-ethyl)amine;
N-(2-{6-[1-(3,5-Dichloro-benzyl)-1H-imidazol-2-yl-methoxy]-pyridin-2-ylamino}-ethyl)-acetamide;
6-[1-(3,5-Dichloro-benzyl)-1H-imidazol-2-ylmethoxy]-3',4',5',6',1",2",3",4",5",6"-decahydro-2'H-[2,1';4',4"]terpyridine;

{6-[1-(3,5-Dichloro-benzyl)-1H-imidazol-2-ylmethoxy]-pyridin-2-yl}-(S)-1-pyrrolidin-2-ylmethyl-amine;
{6-[1-(3,5-Dichloro-benzyl)-1H-imidazol-2-ylmethoxy]-pyridin-2-yl}-[2-(1H-imidazol-4-yl)ethyl]-amine;
1-{6-[1-(3,5-Dichloro-benzyl)-1H-imidazol-2-yl-methoxy]-pyridin-2-yl}-piperazine;
N1-{6-[1-(3,5-Dichloro-benzyl)-1H-imidazol-2-yl-methoxy]-pyridin-2-yl}-ethane-1,2diamine;
N'-{6-[1-(3,5-Dichloro-benzyl)-1H-imidazol-2-yl-methoxy]-pyridin-2-yl}-N,N-dimethylethane-1,2-diamine;
N-{6-[1-(3,5-Dichloro-benzyl)-1H-imidazol-2-yl-methoxy]-pyridin-2-yl}-cyclohexane-1,4diamine;
N-{6-[1-(3,5-Dichloro-benzyl)-1H-imidazol-2-yl-methoxy]-pyridin-2-yl}-cyclohexane-1,2-diamine;
N-{6-[1-(3,5-Dichloro-benzyl)-1H-imidazol-2-yl-methoxy]-pyridin-2-yl}-N',N',N'-trimethylethane-1,2-diamine;
{6-[1-(3,5-Dichloro-benzyl)-1H-imidazol-2-ylmethoxy]-pyridin-2-yl}-[2-(1-methylpyrrolidin-2-yl)-ethyl]-amine;
2-[1-(3,5-Dichloro-benzyl)-1H-imidazol-2-ylmethoxy]-6-pyrrolidin-1-yl-pyridine;
{6-[1-(3,5-Dichloro-benzyl)-1H-imidazol-2-ylmethoxy]-pyridin-2-yl}-(2-morpholin-4-ylethyl)-amine;
{6-[1-(3,5-Dichloro-benzyl)-1H-imidazol-2-ylmethoxy]-pyridin-2-yl}-pyridin-4-ylmethylamine;
N'-{6-[1-(3,5-Dichloro-benzyl)-1H-imidazol-2-yl-methoxy]-pyridin-2-yl}-N,N-dimethylpropane-1,3-diamine;
{6-[1-(3,5-Dichloro-benzyl)-1H-imidazol-2-ylmethoxy]-pyridin-2-yl}-(3-imidazol-1-ylpropyl)-amine;
{6-[1-(3,5-Dichloro-benzyl)-1H-imidazol-2-ylmethoxy]-pyridin-2-yl}-(1-ethyl-pyffolidin-2ylmethyl)-amine;
6'-[1-(3,5-Dichloro-benzyl)-1H-imidazol-2-ylmethoxy]-3,4,5,6-tetrahydro-2H[1,2']bipyridinyl; or
N-(1-{6-[1-(3,5-Dichloro-benzyl)-1H-imidazol-2-yl-methoxy]-pyridin-2-yl}-pyrrolidin-3-yl)-N-methyl-acetamide.

4. A compound which is:
2-(3-Chloro-5-methoxy-phenoxymethyl)-1-(3,5-dichloro-benzyl)-1H-imidazole;
[1-(3,5-Dichloro-benzyl)-1H-imidazol-2-ylmethyl]-(3-fluoro-benzyl)-amine;
[1-(3,5-Dichloro-benzyl)-1H-imidazol-2-ylmethyl]-(3,5-difluoro-benzyl)-amine;
{2-[[1-(3,5-Dichloro-benzyl)-1H-imidazol-2-ylmethyl]-(3-fluoro-benzyl)-amino]-ethyl}-carbamic acid tert-butyl ester;
3-[[1-(3,5-Dichloro-benzyl)-1H-imidazol-2-ylmethyl]-(3-fluoro-benzyl)-amino]-propionamide;
N-{2-[[1-(3,5-Dichloro-benzyl)-1H-imidazol-2-ylmethyl]-(3-fluoro-benzyl)-amino]-ethyl}-acetamide;
$N^1$-[1-(3,5-Dichloro-benzyl)-1H-imidazol-2-ylmethyl] $N^1$-(3-fluoro-benzyl)-ethane-1,2diamine;
(S)-1-{6-[1-(3,5-Dichloro-benzyl)-1H-imidazol-2-yl-methoxy]-pyridin-2-yl}-pyrrolidine-2-carboxylic acid amide;
{6-[1-(3,5-Dichloro-benzyl)-1H-imidazol-2-ylmethoxy]-pyridin-2-yl}-pyridin-4-ylmethylamine;
N-(1-{6-[1-(3,5-Dichloro-benzyl)-1H-imidazol-2-yl-methoxy]-pyridin-2-yl}-pyrrolidin-3-yl)N-methyl-acetamide,
N-(2-{6-[1-(3,5-Dichloro-benzyl)-1H-imidazol-2-yl-methoxy]-pyridin-2-ylamino}-ethyl)-acetamide;
N-{6-[1-(3,5-Dichloro-benzyl)-1H-imidazol-2-yl-methoxy]-pyridin-2-yl}-cyclohexane-1,2diamine;
{6-[1-(3,5-Dichloro-benzyl)-1H-imidazol-2-ylmethoxy]-pyridin-2-yl }-[2-(1-methylpyrrolidin-2-yl)-ethyl]-amine;
{6-[1-(3,5-Dichloro-benzyl)-1H-imidazol-2-ylmethoxy]-pyridin-2-yl}-(1-ethyl-pyrrolidin-2ylmethyl)-amine;
{6-[1-(3,5-Dichloro-benzyl)-1H-imidazol-2-ylmethoxy]-pyridin-2-yl }-(3-imidazol-1-ylpropyl)-amine; or
N-{6-[1-(3,5-Dichloro-benzyl)-1H-imidazol-2-yl-methoxy]-pyridin-2-yl}-N',N',N'-trimethylethane-1,2-diamine.

5. A pharmaceutical composition comprising a compound in accordance with claim 1 and at least one pharmaceutically acceptable carrier.

6. A pharmaceutical composition comprising a compound in accordance with claim 2 and at least one pharmaceutically acceptable carrier.

* * * * *